(12) United States Patent
Carter et al.

(10) Patent No.: US 11,241,335 B2
(45) Date of Patent: Feb. 8, 2022

(54) OPHTHALMIC CUTTING INSTRUMENTS HAVING INTEGRATED ASPIRATION PUMP

(71) Applicant: Carl Zeiss Meditec Cataract Technology Inc., Reno, NV (US)

(72) Inventors: Brett Carter, Reno, NV (US); Scott Chamness, Reno, NV (US); Luke W. Clauson, Reno, NV (US); Nicholas G. Lewis, Reno, NV (US); Matthew Newell, Reno, NV (US); Michael Raye, Reno, NV (US); Thomas M. Rector, Reno, NV (US); Michael P. Schaller, Reno, NV (US)

(73) Assignee: Carl Zeiss Meditec Cataract Technology Inc., Reno, NV (US)

( * ) Notice: Subject to any disclaimer, the term of this patent is extended or adjusted under 35 U.S.C. 154(b) by 41 days.

(21) Appl. No.: 16/778,755

(22) Filed: Jan. 31, 2020

(65) Prior Publication Data

US 2020/0289319 A1 Sep. 17, 2020

Related U.S. Application Data

(60) Provisional application No. 62/868,688, filed on Jun. 28, 2019, provisional application No. 62/815,673, (Continued)

(51) Int. Cl.
*A61F 9/007* (2006.01)
*A61M 1/00* (2006.01)
*A61B 17/00* (2006.01)

(52) U.S. Cl.
CPC ...... *A61F 9/00763* (2013.01); *A61F 9/00745* (2013.01); *A61M 1/80* (2021.05);
(Continued)

(58) Field of Classification Search
CPC .............. A61F 9/00763; A61F 9/00745; A61F 9/00736; A61M 1/80; A61B 2017/0023;
(Continued)

(56) References Cited

U.S. PATENT DOCUMENTS 2,947,470 A 8/1960 Ruben et al.
3,589,363 A 6/1971 Banko et al.
(Continued)

FOREIGN PATENT DOCUMENTS

DE 10 2007 031722 A1 1/2009
DE 10 2007 040290 B4 7/2019
(Continued)

OTHER PUBLICATIONS

U.S. Appl. No. 15/970,439, filed May 3, 2018, US 2018-0318132.
(Continued)

*Primary Examiner* — Melanie R Tyson
*Assistant Examiner* — Andrew P. Restaino
(74) *Attorney, Agent, or Firm* — Mintz Levin Cohn Ferris Glovsky and Popeo, P.C.

(57) ABSTRACT

A device for extracting lens material from an eye including a distal, disposable portion releasably coupleable to a proximal, reusable portion. The disposable portion includes a cutting tube having a distal cutting tip and an inner lumen having an open distal end. The disposable portion includes an aspiration pump fluidly coupled to the inner lumen of the cutting tube and a cutting tube drive mechanism configured to oscillate the cutting tube. The reusable portion includes an aspiration pump motor configured to drive the aspiration pump and a coupler for releasably operatively coupling the pump motor to the aspiration pump. Related devices, systems, and methods are disclosed.

39 Claims, 58 Drawing Sheets

Related U.S. Application Data filed on Mar. 8, 2019, provisional application No. 62/800,198, filed on Feb. 1, 2019.

(52) U.S. Cl.
CPC .............. *A61B 2017/0023* (2013.01); *A61B 2017/00402* (2013.01); *A61B 2217/005* (2013.01); *A61B 2217/007* (2013.01)

(58) Field of Classification Search
CPC .... A61B 2017/00402; A61B 2217/005; A61B 2217/007; A61B 17/32; A61B 17/320016; A61B 17/320068; A61B 2017/320024; A61B 2017/320028
See application file for complete search history.

(56) References Cited

U.S. PATENT DOCUMENTS

| | | |
|---|---|---|
| 3,957,052 A | 5/1976 | Topham |
| 4,368,734 A | 1/1983 | Banko |
| 4,493,706 A | 1/1985 | Borsanyi et al. |
| 4,705,500 A | 11/1987 | Reimels et al. |
| 4,764,165 A | 8/1988 | Reimels et al. |
| 4,854,825 A | 8/1989 | Bez et al. |
| 4,891,044 A | 1/1990 | Mitchell |
| 4,908,015 A | 3/1990 | Anis |
| 4,921,477 A | 5/1990 | Davis |
| 5,146,921 A | 9/1992 | Terwilliger et al. |
| 5,222,959 A | 6/1993 | Anis |
| 5,275,607 A | 1/1994 | Lo et al. |
| 5,279,547 A | 1/1994 | Costin |
| 5,437,678 A | 8/1995 | Sorensen |
| 5,651,783 A | 7/1997 | Reynard |
| 5,676,649 A | 10/1997 | Boukhny et al. |
| 5,693,062 A | 12/1997 | Stegmann et al. |
| 5,788,679 A | 8/1998 | Gravlee, Jr. |
| 5,807,401 A | 9/1998 | Grieshaber et al. |
| 5,843,071 A | 12/1998 | Bath |
| 5,891,153 A | 4/1999 | Peterson |
| 5,911,699 A | 6/1999 | Anis et al. |
| 5,938,677 A | 8/1999 | Boukhny et al. |
| 6,013,049 A | 1/2000 | Rockley et al. |
| 6,059,765 A | 5/2000 | Cole et al. |
| 6,074,396 A | 6/2000 | Geuder |
| 6,117,149 A | 9/2000 | Sorensen et al. |
| 6,132,436 A | 10/2000 | Portney |
| 6,165,190 A | 12/2000 | Nguyen |
| 6,183,433 B1 | 2/2001 | Bays |
| 6,241,700 B1 | 6/2001 | Leukanech |
| 6,254,587 B1 | 7/2001 | Christ et al. |
| 6,299,591 B1 | 10/2001 | Banko |
| 6,319,222 B1 | 11/2001 | Andrew et al. |
| 6,322,557 B1 | 11/2001 | Nikolaevich et al. |
| 6,328,747 B1 | 12/2001 | Nun |
| 6,398,754 B1 | 6/2002 | Sutton et al. |
| 6,428,508 B1 | 8/2002 | Ross |
| 6,485,499 B1 | 11/2002 | Oberkamp et al. |
| 6,506,176 B1 | 1/2003 | Mittelstein et al. |
| 6,520,929 B2 | 2/2003 | Zaleski |
| 6,520,955 B2 | 2/2003 | Reynard |
| 6,527,766 B1 | 3/2003 | Bair |
| 6,544,254 B1 | 4/2003 | Bath |
| 6,589,201 B1 | 7/2003 | Sussman et al. |
| 6,592,541 B1 | 7/2003 | Kurwa |
| 6,605,054 B2 | 8/2003 | Rockley |
| 6,623,477 B1 | 9/2003 | Elbrecht et al. |
| 6,852,092 B2 | 2/2005 | Kadziauskas et al. |
| 6,860,868 B1 | 3/2005 | Sussman et al. |
| 6,939,317 B2 | 9/2005 | Zacharias |
| 6,939,341 B2 | 9/2005 | Vijfvinkel |
| 7,041,078 B1 | 5/2006 | Peyman |
| 7,083,589 B2 | 8/2006 | Banko et al. |
| 7,141,047 B2 | 11/2006 | John |
| 7,172,601 B2 | 2/2007 | Ben-Nun |
| 7,182,759 B2 | 2/2007 | Kadziauskas et al. |
| 7,204,820 B2 | 4/2007 | Akahoshi |
| 7,285,107 B1 | 10/2007 | Charles |
| 7,303,566 B2 | 12/2007 | Kishimoto et al. |
| 7,544,178 B2 | 6/2009 | Kadziauskas et al. |
| 7,549,972 B2 | 6/2009 | Luloh et al. |
| 7,588,553 B2 | 9/2009 | Dewey |
| 7,845,235 B2 | 12/2010 | Sandu et al. |
| 7,846,126 B2 | 12/2010 | Steen et al. |
| 7,857,794 B2 | 12/2010 | Dimalanta et al. |
| 7,876,025 B2 | 1/2011 | Ma et al. |
| 7,955,060 B2 | 6/2011 | Gottschalk |
| 7,967,775 B2 | 6/2011 | Hong |
| 8,070,711 B2 | 12/2011 | Bassinger et al. |
| 8,080,029 B2 | 12/2011 | Charles |
| 8,142,388 B2 | 3/2012 | Gomez |
| 8,187,293 B2 | 5/2012 | Kirchhevel |
| 8,216,246 B2 | 7/2012 | Luloh et al. |
| 8,246,644 B2 | 8/2012 | Rockley et al. |
| 8,287,484 B2 | 10/2012 | Rockley |
| 8,298,253 B2 | 10/2012 | Charles |
| 8,308,735 B2 | 11/2012 | Dimalanta |
| 8,317,739 B2 | 11/2012 | Kuebler |
| 8,376,983 B2 | 2/2013 | Ross et al. |
| 8,423,126 B2 | 4/2013 | Mackool |
| 8,475,480 B2 | 7/2013 | Mackool |
| 8,545,462 B2 | 10/2013 | Ghannoum |
| 8,771,301 B2 | 7/2014 | Boukhny et al. |
| 8,784,361 B2 | 7/2014 | Lane |
| 8,801,653 B2 | 8/2014 | Maaskamp et al. |
| 8,852,139 B2 | 10/2014 | King et al. |
| 8,876,745 B2 | 11/2014 | Escaf |
| 8,876,747 B2 | 11/2014 | Kadziauskas et al. |
| 8,939,927 B2 | 1/2015 | Sorensen et al. |
| 8,986,290 B2 | 3/2015 | Patton |
| 9,050,171 B2 | 6/2015 | Foster |
| 9,144,517 B2 | 9/2015 | Kuebler et al. |
| 9,259,597 B2 | 2/2016 | Romano et al. |
| 9,351,871 B2 | 5/2016 | Ghannoum et al. |
| 9,370,611 B2 | 6/2016 | Ross et al. |
| 9,387,122 B2 | 7/2016 | Mackool |
| 9,402,766 B2 | 8/2016 | Akahoshi et al. |
| 9,433,725 B2 | 9/2016 | Schaller et al. |
| 9,439,807 B2 | 9/2016 | Koplin |
| 9,445,943 B2 | 9/2016 | Wilson et al. |
| 9,486,359 B2 | 11/2016 | Hauger et al. |
| 9,486,360 B2 | 11/2016 | Chon |
| 9,498,377 B2 | 11/2016 | McCary et al. |
| 9,498,378 B2 | 11/2016 | McDonell |
| 9,504,604 B2 | 11/2016 | Alvarez |
| 9,561,129 B2 | 2/2017 | Ross et al. |
| 9,566,188 B2 | 2/2017 | Raney et al. |
| 9,592,156 B2 | 3/2017 | Huang |
| 9,629,747 B2 | 4/2017 | Clauson et al. |
| 9,693,896 B2 | 7/2017 | Sussman |
| 9,724,238 B2 | 8/2017 | Heitel |
| 9,731,065 B2 | 8/2017 | Bourne et al. |
| 9,750,639 B2 | 9/2017 | Barnes et al. |
| 9,775,743 B2 | 10/2017 | Clauson et al. |
| 9,827,142 B2 | 11/2017 | Sasazaki et al. |
| 9,839,738 B2 | 12/2017 | Beauvais et al. |
| 9,861,522 B2 | 1/2018 | Sorensen et al. |
| 9,867,635 B2 | 1/2018 | Alvarez et al. |
| 9,878,075 B2 | 1/2018 | Sussman et al. |
| 9,889,247 B2 | 2/2018 | Akahoshi |
| 9,913,752 B2 | 3/2018 | Hauger |
| 10,251,782 B2 | 4/2019 | Farley |
| 10,278,861 B2 | 5/2019 | Bourne |
| 10,294,934 B2 | 5/2019 | Bourne et al. |
| 2002/0052617 A1 | 5/2002 | Anis et al. |
| 2002/0099400 A1 | 7/2002 | Wolf et al. |
| 2002/0151835 A1 | 10/2002 | Ross |
| 2003/0004455 A1 | 1/2003 | Kadziauskas et al. |
| 2003/0055387 A1 | 3/2003 | Sutton et al. |
| 2003/0109867 A1 | 6/2003 | Gluche et al. |
| 2004/0010284 A1 | 1/2004 | Maloof et al. |
| 2004/0049217 A1 | 3/2004 | Ross et al. |
| 2004/0082902 A1 | 4/2004 | Kadziauskas et al. |
| 2004/0092800 A1 | 5/2004 | MacKool |

(56) References Cited

U.S. PATENT DOCUMENTS

| | | |
|---|---|---|
| 2004/0153093 A1 | 8/2004 | Donovan |
| 2005/0113741 A1 | 5/2005 | Huang et al. |
| 2005/0234441 A1 | 10/2005 | Bisch et al. |
| 2005/0234473 A1 | 10/2005 | Zacharias |
| 2006/0135974 A1 | 6/2006 | Perkins |
| 2006/0253056 A1 | 11/2006 | Kadziauskas et al. |
| 2007/0260173 A1 | 11/2007 | Boukhny et al. |
| 2008/0188792 A1 | 8/2008 | Barrett |
| 2008/0300531 A1 | 12/2008 | Gills, Jr. |
| 2009/0048607 A1 | 2/2009 | Rockley |
| 2009/0054904 A1 | 2/2009 | Holmen |
| 2009/0137993 A1 | 5/2009 | Kurtz |
| 2009/0149840 A1 | 6/2009 | Kurtz |
| 2009/0156985 A1 | 6/2009 | Hottmann et al. |
| 2009/0171242 A1 | 7/2009 | Hibner |
| 2010/0030134 A1 | 2/2010 | Fitzgerald et al. |
| 2010/0191178 A1 | 7/2010 | Ross et al. |
| 2010/0292631 A1 | 11/2010 | Holden |
| 2010/0312170 A1 | 12/2010 | Maaskamp et al. |
| 2010/0331911 A1 | 12/2010 | Kovalcheck et al. |
| 2011/0015562 A1 | 1/2011 | Akahoshi |
| 2011/0054384 A1 | 3/2011 | Brown |
| 2011/0112466 A1 | 5/2011 | Dimalanta |
| 2011/0137231 A1 | 6/2011 | Sorensen et al. |
| 2011/0144638 A1 | 6/2011 | Heeren et al. |
| 2011/0295192 A1 | 12/2011 | Geuder |
| 2012/0004595 A1 | 1/2012 | Dubois et al. |
| 2012/0022434 A1 | 1/2012 | Lue et al. |
| 2012/0041358 A1 | 2/2012 | Mann et al. |
| 2012/0072197 A1 | 3/2012 | Ovchinnikov |
| 2012/0089080 A1 | 4/2012 | Ross et al. |
| 2012/0158030 A1 | 6/2012 | Underwood et al. |
| 2012/0184892 A1 | 7/2012 | Bigler et al. |
| 2012/0259320 A1 | 10/2012 | Loesel et al. |
| 2013/0060210 A1 | 3/2013 | Ross et al. |
| 2013/0231605 A1 | 9/2013 | Walter |
| 2013/0282020 A1 | 10/2013 | Hunter |
| 2014/0005681 A1 | 1/2014 | Gee et al. |
| 2014/0052113 A1 | 2/2014 | Kuehnert et al. |
| 2014/0074013 A1 | 3/2014 | McCary et al. |
| 2014/0081151 A1 | 3/2014 | Saimovici |
| 2014/0081266 A1 | 3/2014 | Dubois et al. |
| 2014/0114335 A1 | 4/2014 | Banko |
| 2014/0163455 A1 | 6/2014 | Wilson et al. |
| 2014/0194860 A1 | 7/2014 | Dick et al. |
| 2014/0236163 A1 | 8/2014 | Olson et al. |
| 2014/0257258 A1 | 9/2014 | Kurtz |
| 2014/0271251 A1 | 9/2014 | Bourne et al. |
| 2014/0276364 A1* | 9/2014 | Sussman ............ A61F 9/00745 604/22 |
| 2014/0309649 A1 | 10/2014 | Alvarez et al. |
| 2014/0358155 A1 | 12/2014 | DeBoer et al. |
| 2014/0364885 A1 | 12/2014 | Wells et al. |
| 2015/0005753 A1 | 1/2015 | Walter |
| 2015/0025450 A1 | 1/2015 | King et al. |
| 2015/0038894 A1 | 2/2015 | Urich et al. |
| 2015/0045806 A1 | 2/2015 | Urich et al. |
| 2015/0105791 A1 | 4/2015 | Truckai |
| 2015/0141801 A1 | 5/2015 | Jean et al. |
| 2015/0144514 A1 | 5/2015 | Brennen |
| 2015/0196426 A1 | 7/2015 | Kuebler et al. |
| 2015/0202081 A1 | 7/2015 | Eichler |
| 2015/0216728 A1 | 8/2015 | Keller |
| 2015/0257927 A1 | 9/2015 | Olson |
| 2015/0297407 A1 | 10/2015 | Saimovici |
| 2015/0306286 A1* | 10/2015 | Ross .................... A61M 1/743 604/22 |
| 2015/0328047 A1 | 11/2015 | Falck, Jr. |
| 2015/0359672 A1 | 12/2015 | Van Valen et al. |
| 2016/0022489 A1 | 1/2016 | Hartstra |
| 2016/0058614 A1 | 3/2016 | Ross et al. |
| 2016/0067091 A1 | 3/2016 | Wells et al. |
| 2016/0089268 A1 | 3/2016 | Chon et al. |
| 2016/0095749 A1 | 4/2016 | Raney et al. |
| 2016/0095750 A1 | 4/2016 | Raney et al. |
| 2016/0106580 A1 | 4/2016 | Banko |
| 2016/0106893 A1 | 4/2016 | Zacharias |
| 2016/0128869 A1 | 5/2016 | Zacharias |
| 2016/0143780 A1 | 5/2016 | Gunn |
| 2016/0166432 A1 | 6/2016 | Kahook et al. |
| 2016/0175578 A1 | 6/2016 | Roholt |
| 2017/0007451 A1 | 1/2017 | Depenbusch |
| 2017/0007452 A1 | 1/2017 | Depenbusch |
| 2017/0020728 A1 | 1/2017 | McDonell |
| 2017/0027750 A1 | 2/2017 | Wiley |
| 2017/0087013 A1 | 3/2017 | Prats et al. |
| 2017/0151091 A1 | 6/2017 | Bourne et al. |
| 2017/0151378 A1 | 6/2017 | Raney et al. |
| 2017/0211959 A1 | 7/2017 | Adler et al. |
| 2017/0312125 A1 | 11/2017 | Clauson et al. |
| 2017/0333252 A1 | 11/2017 | Biancalana et al. |
| 2017/0360607 A1 | 12/2017 | Price et al. |
| 2017/0367885 A1 | 12/2017 | Bourne |
| 2018/0028360 A1 | 2/2018 | Kozawa |
| 2018/0036171 A1 | 2/2018 | Clauson et al. |
| 2018/0049920 A1 | 2/2018 | Charles |
| 2018/0049921 A1 | 2/2018 | Sorensen et al. |
| 2018/0058438 A1 | 3/2018 | Ochoa |
| 2018/0064578 A1 | 3/2018 | Clauson et al. |
| 2018/0318132 A1 | 11/2018 | Clauson et al. |
| 2018/0318133 A1 | 11/2018 | Clauson et al. |
| 2019/0015252 A1 | 1/2019 | Lake et al. |
| 2019/0041665 A1 | 2/2019 | Widman et al. |
| 2019/0099292 A1 | 4/2019 | Strayer et al. |
| 2019/0133825 A1 | 5/2019 | Clauson et al. |
| 2019/0151149 A1 | 5/2019 | Clauson et al. |
| 2019/0183679 A1 | 6/2019 | Sawicz |
| 2019/0183681 A1 | 6/2019 | Schaller et al. |
| 2019/0254872 A1 | 8/2019 | Clauson et al. |
| 2019/0269557 A1 | 9/2019 | Clauson et al. |
| 2019/0282402 A1 | 9/2019 | Clauson et al. |
| 2019/0321223 A1 | 10/2019 | Chamness et al. |
| 2019/0365567 A1 | 12/2019 | Balkenbush et al. |
| 2019/0388272 A1 | 12/2019 | Clauson et al. |
| 2020/0016001 A1 | 1/2020 | McDonell et al. |
| 2020/0022841 A1 | 1/2020 | Chamness et al. |
| 2020/0060875 A1 | 2/2020 | Clauson et al. |
| 2020/0360185 A1 | 11/2020 | Carter et al. |
| 2020/0383833 A1 | 12/2020 | Schaller et al. |

FOREIGN PATENT DOCUMENTS

| | | |
|---|---|---|
| EP | 1832259 B1 | 6/2009 |
| EP | 1556099 B1 | 7/2013 |
| EP | 2168540 B1 | 4/2015 |
| EP | 2 094 173 B1 | 3/2016 |
| EP | 1735030 B1 | 8/2016 |
| EP | 2 892 438 B1 | 10/2018 |
| GB | 1304324 A | 1/1973 |
| GB | 2018601 A | 10/1979 |
| JP | H0779826 B2 | 8/1995 |
| JP | 6654763 B2 | 2/2020 |
| WO | WO-2013/039742 A2 | 3/2013 |
| WO | WO-2015/161149 A1 | 10/2015 |
| WO | WO-2018/081295 A1 | 5/2018 |
| WO | WO-2018/217579 A1 | 11/2018 |

OTHER PUBLICATIONS

U.S. Appl. No. 16/221,239, filed Dec. 14, 2018, US 2019-0183681.
U.S. Appl. No. 16/257,533, filed Jan. 25, 2019, US 2019-0151149.
U.S. Appl. No. 16/345,182, filed Apr. 25, 2019, US 2019-0282402.
U.S. Appl. No. 16/404,252, filed May 6, 2019, US 2019-0254872.
U.S. Appl. No. 16/431,560, filed Jun. 4, 2019, US 2019-0365567.
U.S. Appl. No. 16/436,648, filed Jun. 10, 2019, US 2019-0321223.
U.S. Appl. No. 16/577,418, filed Sep. 20, 2019, US 2020-0022841.
U.S. Appl. No. 16/667,030, filed Oct. 29, 2019, US 2020-0060875.
PCT/US2018/65800, Dec. 14, 2018, WO 2019/118901.
PCT/US2019/35442, Jun. 4, 2019, WO 2019/236615.
U.S. Appl. No. 16/690,881, filed Nov. 21, 2019, US 2020-0197222.
U.S. Appl. No. 16/811,786, filed Mar. 6, 2020, US 2020-0306083.
U.S. Appl. No. 16/875,421, filed May 15, 2020, US 2020-0383833.

(56) References Cited

OTHER PUBLICATIONS

U.S. Appl. No. 16/875,426, filed May 15, 2020, US 2020-0360185.
U.S. Appl. No. 17/177,017, filed Feb. 16, 2021, US 2021-0161712.
PCT/US/2020/33141, May 15, 2020, WO 2020/236593.
PCT/US/2020/33142, May 15, 2020, WO 2020/247165.

* cited by examiner

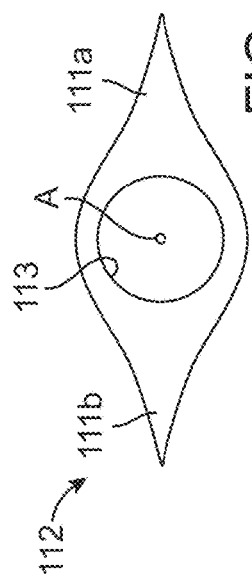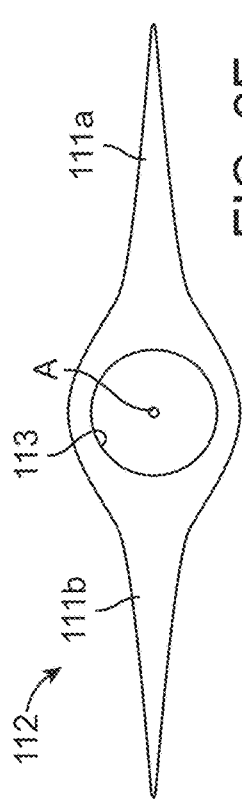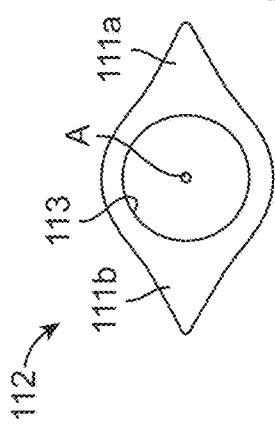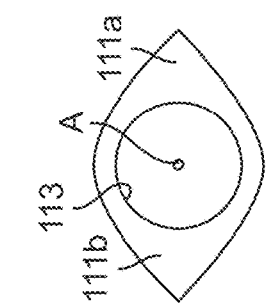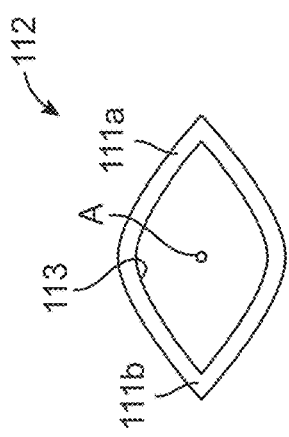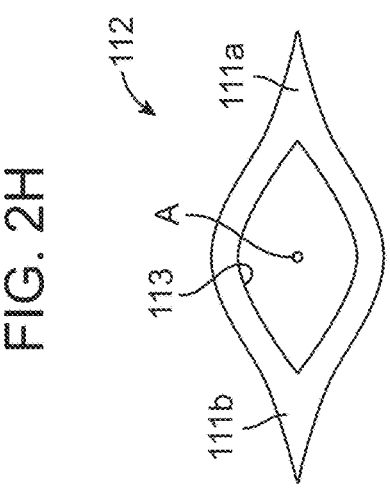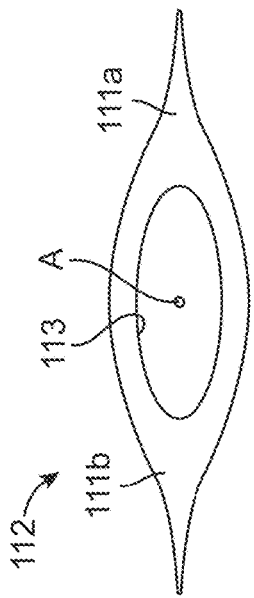

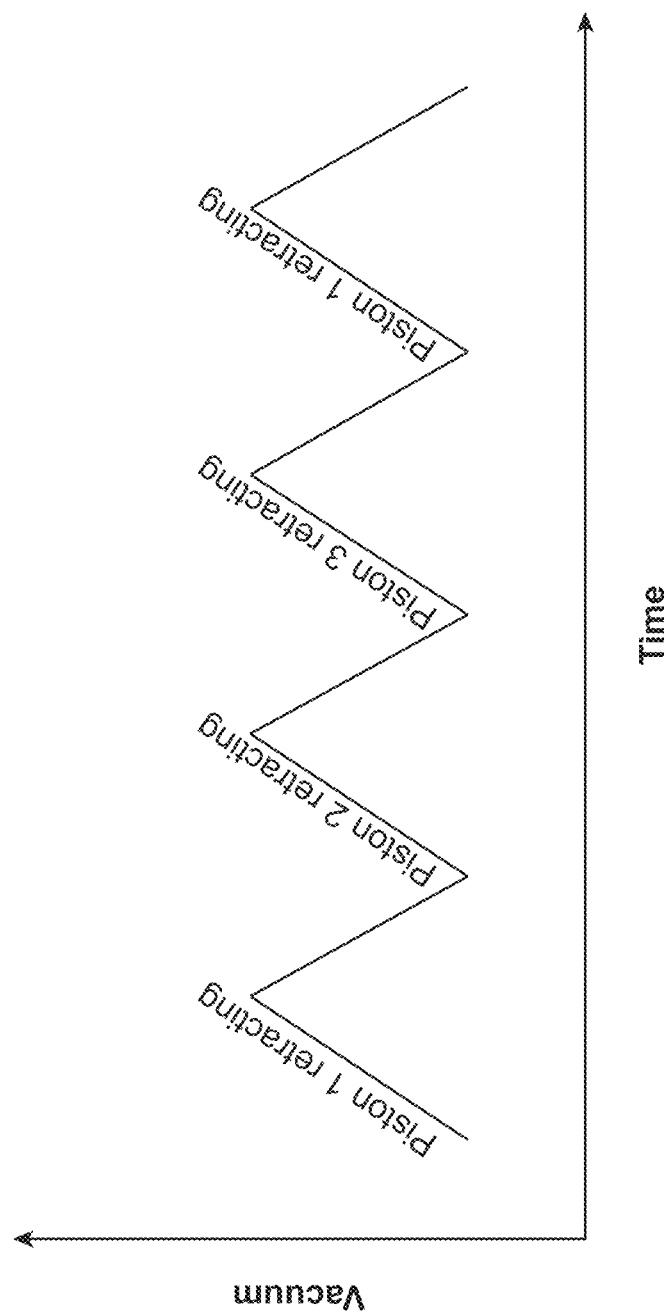

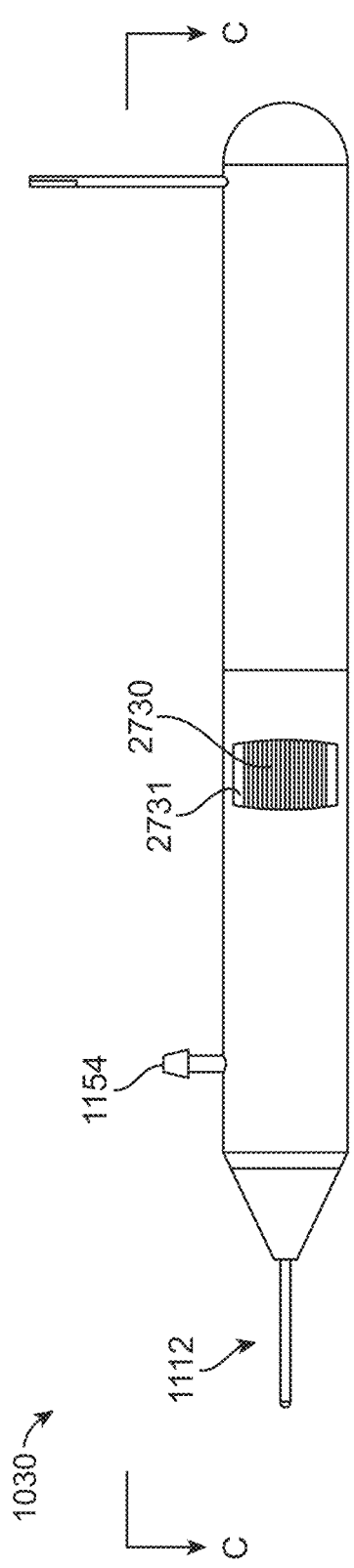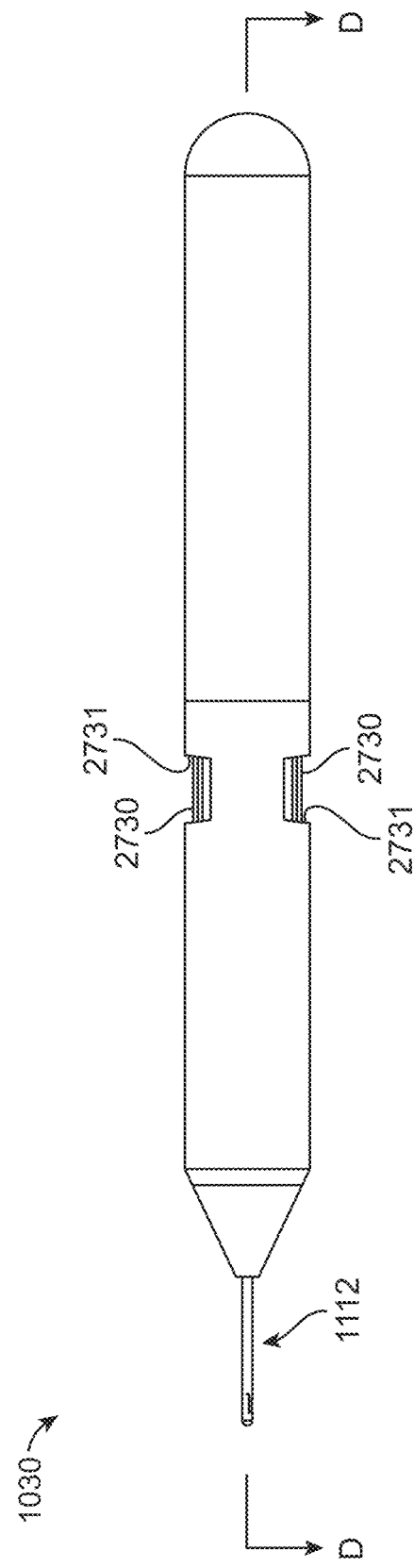

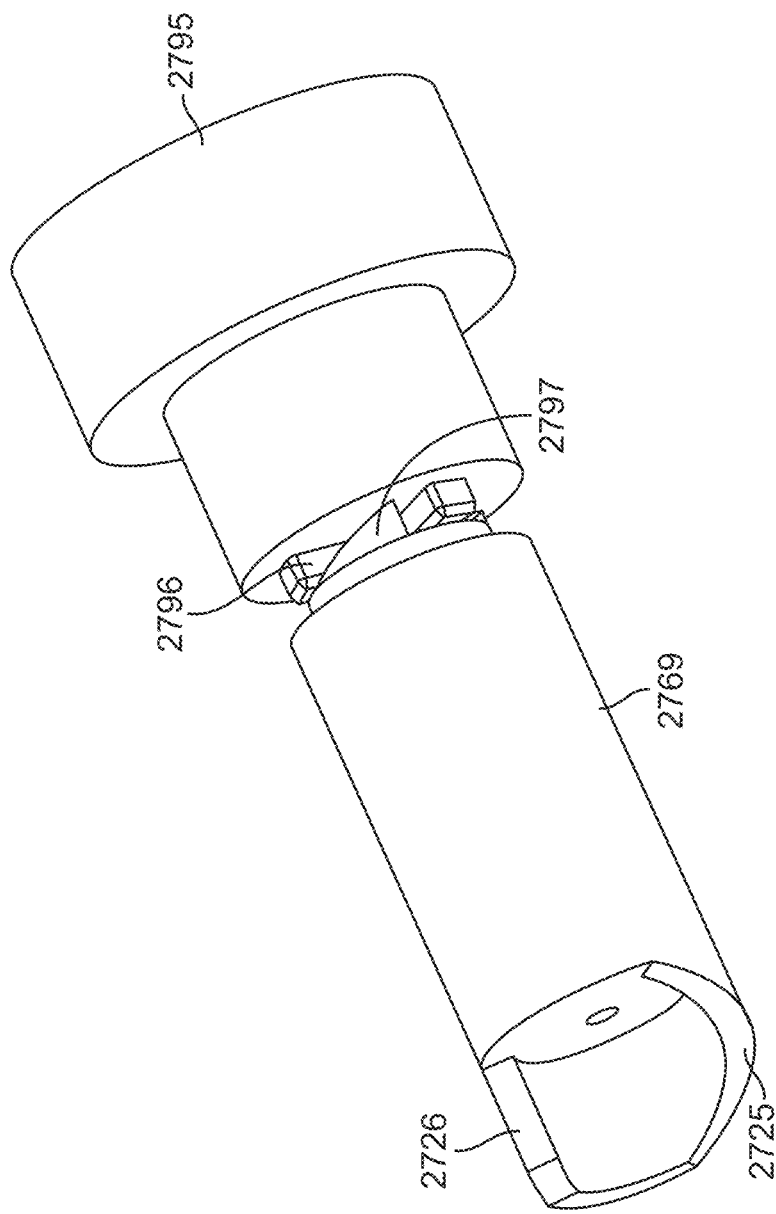

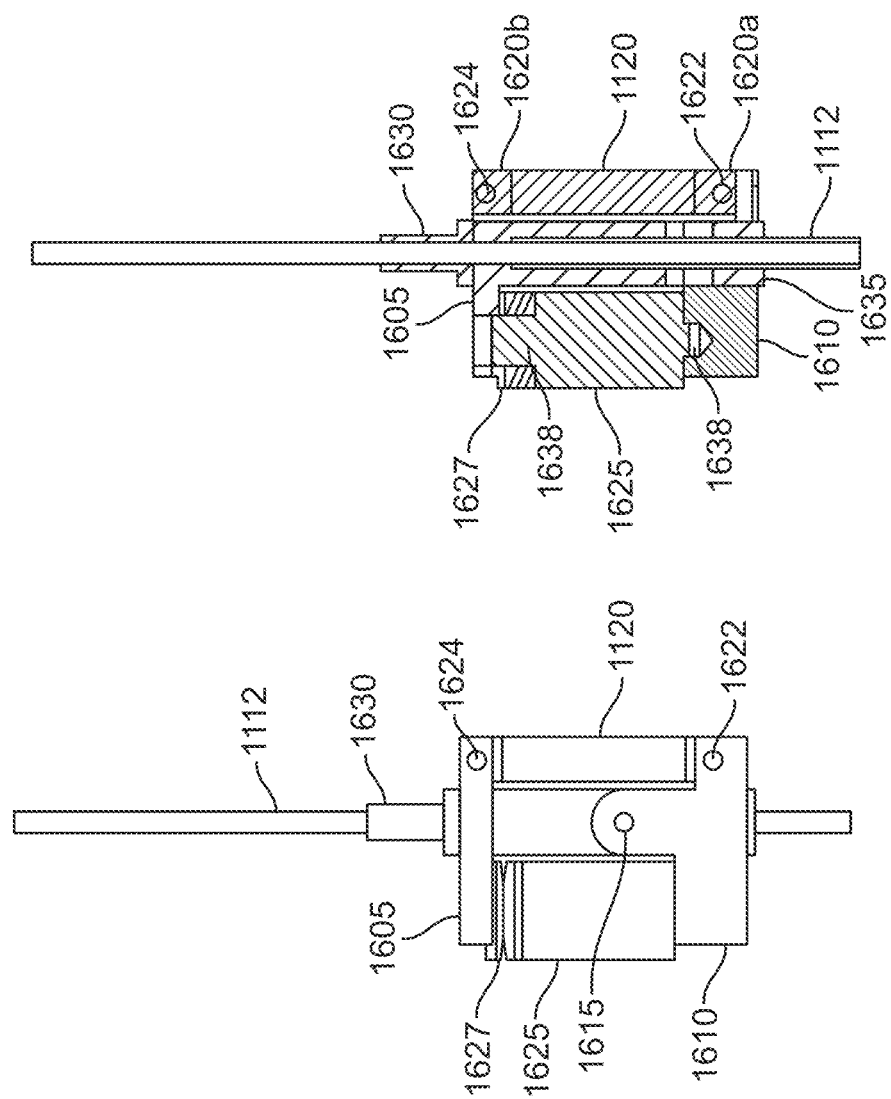
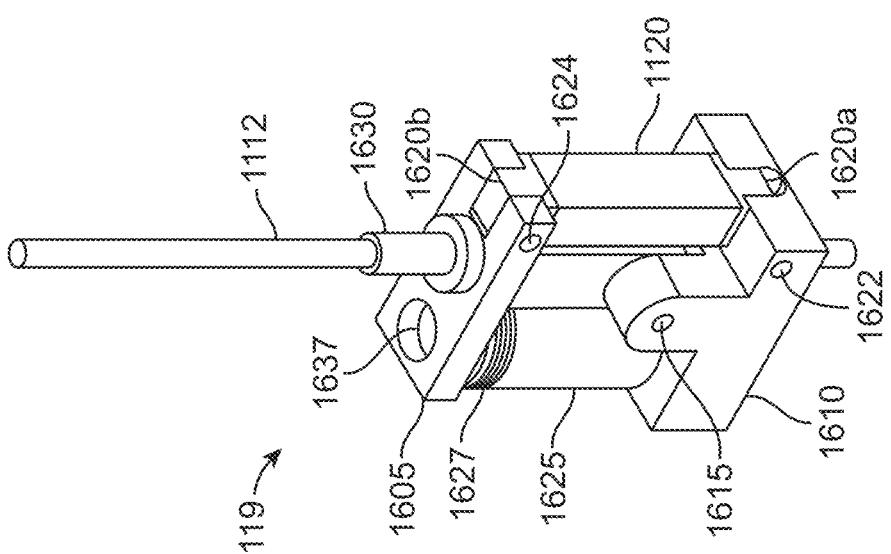
FIG. 16A   FIG. 16B   FIG. 16C

OPHTHALMIC CUTTING INSTRUMENTS HAVING INTEGRATED ASPIRATION PUMP

CROSS-REFERENCE TO RELATED APPLICATIONS

This application claims the benefit of priority under 35 U.S.C. § 119(e) to U.S. Provisional Patent Application Ser. Nos. 62/800,198, filed Feb. 1, 2019, 62/815,673, filed Mar. 8, 2019, and 62/868,688, filed Jun. 28, 2019. The disclosures of the provisional applications are hereby incorporated by reference in their entireties.

FIELD

The present technology relates generally to ophthalmic microsurgical tools and systems, in particular, ophthalmic microsurgical tools and systems having integrated pumping.

BACKGROUND

Certain types of conventional ophthalmic surgery require breaking up lenticular tissue and solid intraocular objects, such as the intraocular lens or vitreous into pieces so that it can be extracted from the eye. For example, extraction of lenses for cataract surgery is one of the most common outpatient surgical fields with more than 3 million cases performed annually in the United States alone. During cataract surgery a commonly used method for lens extraction is phacoemulsification, which incorporates using ultrasonic energy to break up the lens and then aspiration to remove the lens fragments through the instrument. Other methods of lens fragmentation and extraction may include the use of instruments such as hooks, knives, or laser to break up the lens into fragments and then extract through an incision in the cornea in an ab interno approach. Intraocular, ab interno fragmentation of the lenticular tissue is extremely important in cataract surgery in order to allow removal of cataracts from ocular incisions that are typically not exceeding 2.8-3.0 mm.

Typical phacoemulsification systems include a console in operative communication with a phacoemulsification hand piece. The console typically includes a cabinet, including a power supply, a pump, electronic and associated hardware. The console provides the control of the electronics of the hand piece, aspiration, and irrigation. The hand piece includes a resonating bar directly attached to a set of piezoelectric crystals on a first end and a needle-like cutting tube on the second end. The crystals supply ultrasonic vibration needed to drive the resonating bar and attached cutting tube during phacoemulsification.

During typical phacoemulsification procedures, the tip of the cutting tube extending past the distal end of the irrigation sleeve is inserted into the anterior segment of the eye through a small incision in the outer tissue of the eye. The tip of the cutting tube is brought into contact with the lens of the eye so that the vibrating tip fragments the lens. The fragments are aspirated out of the eye through the inner lumen of the cutting tube, along with any irrigation fluid provided to the eye during the procedure through the irrigation sleeve and directed toward a waste container. During cutting, irrigation fluid is delivered to the eye (i.e. passively or actively) through the irrigation sleeve positioned over the cutting tube. The irrigation fluid is intended to maintain the pressure balance within the eye and prevent collapse of the anterior chamber during the removal of the emulsified lens.

A challenge associated with conventional phaco devices and other devices using a remote vacuum source is that the suction lines are quite long and flexible contributing to the fluidic system compliance. Lastly, the system often contains compressible gas or other material that further adds to the compliance of the system. Long, compliant suction lines containing compressible material affects the responsive times at the tip when suction is turned on and off. Yet another problem with some systems, such as venturi-based systems, is that the waste fluid disposal enclosure is also exposed to vacuum pressure and, as such, the container and gas or other compressible material therein, also responds to changes in pressure and further contributing to the delay in initiation and termination of suction at the tip and contributing to the low responsiveness of some systems.

Conventional methods and devices for delivery of irrigation to an eye, for example during cataract surgery, may also use a substantial amount of circulated irrigation balanced saline solution (BSS). For example, bottles and bags of BSS may be in the range of 250 cc to 500 cc. Corneal endothelial cells can be damaged in multiple ways including the amount of ultrasonic energy delivered to the eye as well the amount of irrigation fluid that circulates through the anterior chamber. Additionally, when larger amounts of irrigation fluid are used, flow rates through the eye are higher and therefore additional turbulence of the irrigating fluid may exist and further cause corneal endothelial cell damage.

SUMMARY

According to a first aspect, disclosed is a device for extracting lens material from an eye. The device includes a distal, disposable portion releasably coupleable to a proximal, reusable portion. The distal, disposable portion includes a cutting tube having a distal cutting tip and an inner lumen having an open distal end. The cutting tube is sized and configured to extend through an anterior chamber of the eye and to a capsular bag. The distal, disposable portion includes an aspiration pump housed within the disposable portion and fluidly coupled to the inner lumen of the cutting tube and a cutting tube drive mechanism configured to oscillate the cutting tube. When in use, the device is configured to aspirate lens material from the capsular bag into the inner lumen. The proximal, reusable portion is configured to remain outside of the eye. The proximal, reusable portion includes an aspiration pump motor configured to drive the aspiration pump; and a coupler for releasably operatively coupling the pump motor to the aspiration pump.

The aspiration pump can be a peristaltic pump. The peristaltic pump can be a linear peristaltic pump having a central camshaft extending longitudinally through a symmetrical double chamber pumping manifold. The central camshaft can have a rotational axis that is coaxially aligned with a longitudinal axis of the distal, disposable portion. The aspiration pump motor rotates the central camshaft. The linear peristaltic pump can further include two tubes extending through the pumping manifold, each of the two tubes having a longitudinal axis that is positioned parallel with the rotational axis of the central camshaft. A first tube of the two tubes is positioned on one side of the camshaft and a second tube of the two tubes is positioned on a second, opposite side of the camshaft. The linear peristaltic pump can further include a proximal flow path and a distal flow path. The proximal flow path can split into two flow paths connected on a proximal end with the two tubes within the pumping manifold. The two tubes can combine distal to the pumping manifold into the distal flow path. The camshaft can further include a plurality of lobed cams that work in time to drive a plurality of cam followers towards and away from the two tubes to create sequential, progressive compression of the two tubes to push a fluid volume toward the distal flow path. Motion of the plurality of cam followers can be in a plane perpendicular to the rotational axis of the camshaft and to the longitudinal axis of the two tubes. The plurality of cam followers can sequentially compress the two tubes in a wave-like fashion. The plurality of cam followers can apply no force in a direction of the longitudinal axis of the two tube and generate little to no friction on the two tubes.

The device can further include an external vacuum source operatively releasably coupleable to at least one of the proximal, reusable portion and the distal, disposable portion. The external vacuum source can be configured to provide a level of continuous negative pressure within the inner lumen. The level of continuous negative pressure can be less than a level of the negative pressure generated by the aspiration pump of the distal, disposable portion.

The cutting tube drive mechanism can cause oscillatory motion of the cutting tube via a mechanical hinge. The cutting tube drive mechanism can incorporate less than 2 nodal inflection points between a point of application of a drive force and the distal cutting tip of the cutting tube. The cutting tube drive mechanism can include a base, a rocker, and a pivot pin, the rocker being movably coupled to the base by the pivot pin and configured to rotate relative to the base around a rotational axis of the pivot pin. The cutting tube can extend through a center of the rocker and the pivot pin is substantially aligned along the longitudinal axis of the cutting tube creating a fulcrum for the rocker.

The drive mechanism can further a piezoelectric stack and a spring stack, the piezoelectric stack and the spring stack being positioned on opposite sides of the cutting tube. The spring stack can create an upward force against a first end of rocker urging a second, opposite end of the rocker downward against the piezoelectric stack. The piezoelectric stack can expand under varying voltage rotating the rocker about the rotational axis of the pivot pin causing the cutting tube to move in at least one direction. Retraction of the piezoelectric stack can allow the upward force of the spring stack against the first end of the rocker to urge the second, opposite end of the rocker downward maintaining contact with the retracting piezoelectric stack. The drive mechanism can further include a motor-driven cam and cam follower coupled to the rocker. The drive mechanism can further include a motor and a motor shaft, the motor shaft having an offset weight configured to cause motion of the rocker as the motor shaft spins. The rocker can be a straight rocker and the pivot pin is aligned with the rocker along the longitudinal axis of the cutter tube. The rocker can be an offset rocker and the pivot pin is positioned proximal to the rocker along the longitudinal axis of the cutter tube.

The cutting tube drive mechanism can create a drive force applied to generate longitudinal oscillatory motion and/or torsional oscillatory motion. The oscillatory motion can be in an ultrasonic frequency range or in a frequency range that is less than ultrasonic. A frequency of oscillation of the distal cutting tip can be between about 0.5 Hz to 5000 Hz.

The cutting tube can incorporate a non-circular cross-sectional geometry along at least a portion of its length. The non-circular cross-sectional geometry can include oval, elliptical, lentoid, tear-drop, or diamond shape. The cutting tube can incorporate at least a first tapered profile extending laterally from a central axis of the cutting tube. The cutting tube can have an asymmetric cross-section forming a single tapered profile extending from one side of the cutting tube and a circular profile on an opposite side of the cutting tube. The cutting tube can have a cross-sectional shape that varies along its length. The cutting tube can incorporate a non-circular geometry in only a distal-most length of the cutting tube. The distal-most length can be approximately 1 mm.

The proximal, reusable portion can further include a throttle mechanism for varying a speed of the aspiration pump motor, the throttle mechanism operatively coupled to an actuator. The device can further include an irrigation lumen coupleable to a source of irrigation fluid. The irrigation lumen can include an annular space at least in part surrounding the cutting tube.

In an interrelated aspect, provided is a device for extracting lens material from an eye including a cutting tube having a distal cutting tip and an inner lumen, the cutting tube sized and configured to extend through an anterior chamber of the eye and to a capsular bag; and a cutting tube drive mechanism configured to oscillate the cutting tube via a mechanical hinge. The cutting tube drive mechanism incorporates less than 2 nodal inflection points between a point of application of a drive force and the distal cutting tube of the cutting tube.

The cutting tube drive mechanism can include a base, a rocker, and a pivot pin, the rocker being movably coupled to the base by the pivot pin and configured to rotate relative to the base around a rotational axis of the pivot pin. The cutting tube can extend through a center of the rocker and the pivot pin is substantially aligned along the longitudinal axis of the cutting tube creating a fulcrum for the rocker. The drive mechanism can further include a piezoelectric stack and a spring stack, the piezoelectric stack and the spring stack being positioned on opposite sides of the cutting tube. The spring stack can create an upward force against a first end of rocker urging a second, opposite end of the rocker downward against the piezoelectric stack. The piezoelectric stack can expand under varying voltage rotating the rocker about the rotational axis of the pivot pin causing the cutting tube to move in at least one direction. Retraction of the piezoelectric stack can allow the upward force of the spring stack against the first end of the rocker to urge the second, opposite end of the rocker downward maintaining contact with the retracting piezoelectric stack. The drive mechanism can further include a motor-driven cam and cam follower coupled to the rocker. The drive mechanism can further include a motor and a motor shaft, the motor shaft having an offset weight configured to cause motion of the rocker as the motor shaft spins. The rocker can be a straight rocker and the pivot pin aligned with the rocker along the longitudinal axis of the cutter tube. The rocker can be an offset rocker and the pivot pin positioned proximal to the rocker along the longitudinal axis of the cutter tube. The cutting tube drive mechanism can create a drive force applied to generate longitudinal oscillatory motion and/or torsional oscillatory motion. The oscillatory motion can be in an ultrasonic frequency range or in a frequency range that is less than ultrasonic. The frequency of oscillation of the distal cutting tip can be between about 0.5 Hz to 5000 Hz.

The device can further include an aspiration pump fluidly coupled to the inner lumen of the cutting tube, wherein, in use, the device is configured to aspirate lens material from the capsular bag into the inner lumen. The aspiration pump can be a peristaltic pump. The peristaltic pump can be a linear peristaltic pump having a central camshaft extending longitudinally through a symmetrical double chamber pumping manifold, the central camshaft having a rotational axis that is coaxially aligned with a longitudinal axis of the distal, disposable portion. The camshaft can include a plurality of lobed cams that work in time to drive a plurality of cam followers towards and away from two tubes extending through the pumping manifold to create sequential, progressive compression of the two tubes to push a fluid volume toward the distal flow path. Each of the two tubes can include a longitudinal axis that is positioned parallel with the rotational axis of the central camshaft. A first of the two tubes can be positioned on one side of the camshaft and a second tube of the two tubes is positioned on a second, opposite side of the camshaft. Motion of the plurality of cam followers can be in a plane perpendicular to the rotational axis of the camshaft and to the longitudinal axis of the two tubes. The plurality of cam followers can sequentially compress the two tubes in a wave-like fashion. The plurality of cam followers can apply no force in a direction of the longitudinal axis of the two tubes and generate little to no friction on the two tubes.

In an interrelated aspect, provided is a device for extracting lens material from an eye including a cutting tube having a distal cutting tip and an inner lumen having an open distal end, the cutting tube sized and configured to extend through an anterior chamber of the eye and to a capsular bag, wherein, in use, the device is configured to aspirate lens material from the capsular bag into the inner lumen. The device includes a cutting tube drive mechanism configured to oscillate the cutting tube torsionally. The cutting tube incorporates a non-circular cross-sectional geometry along at least a portion of its length.

The oscillatory motion can be in an ultrasonic frequency range or in a frequency range that is less than ultrasonic. The non-circular cross-sectional geometry can include oval, elliptical, lentoid, tear-drop, or diamond shape. The non-circular cross-sectional geometry can incorporate at least a first tapered profile extending laterally from a central axis of the cutting tube. The non-circular cross-sectional geometry can be asymmetric and incorporate a single tapered profile extending from one side of the cutting tube and a circular profile on an opposite side of the cutting tube. The cutting tube can incorporate the non-circular cross-sectional geometry in only a distal-most length of the cutting tube. The distal-most length can be approximately 1 mm.

In some variations, one or more of the following can optionally be included in any feasible combination in the above methods, apparatus, devices, and systems. More details of the devices, systems, apparatus, and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking, the figures are not to scale in absolute terms or comparatively, but are intended to be illustrative. Also, relative placement of features and elements may be modified for the purpose of illustrative clarity.

FIGS. 2D-2G are cross-sectional views of implementations of cutting tubes incorporating tapered profiles of varying geometry;
FIGS. 2H-2J are cross-sectional views of implementations of cutting tubes incorporating tapered profiles of varying external and internal (luminal) geometry;
FIG. 11A shows an implementation of a vacuum profile for a piston pump of the hand piece.

FIGS. 13A-13B show side views of an implementation of a hand piece for cutting and aspirating material from an eye configured to be used with a microsurgical control system;

FIGS. 13C-13E show various view of a rotating cam of the hand piece of FIGS. 13A-13B.

FIG. 16A illustrates an implementation of a cutter tube drive mechanism incorporating an off-set rocker;

FIGS. 16B-16C are side and cross-sectional views, respectively, of the cutter tube drive mechanism of FIG. 16A;

It should be appreciated that the drawings are for example only and are not meant to be to scale. It is to be understood that devices described herein may include features not necessarily depicted in each figure.

DETAILED DESCRIPTION

Described herein are systems, devices, and methods for ophthalmic microsurgical tools useful for intraocular fragmentation and removal of the lens, vitreous, and other tissues during intraocular surgery. The various systems, devices, and methods are configured to perform one or more functions useful in ophthalmic procedures including, but not limited to, cutting, fragmentation, emulsification, aspiration, and/or irrigation of material present at a target location during a procedure in the eye.

"Material" as used herein can include fluids (from the eye or provided to the eye), tissues, or fragments of tissues such as lenticular tissue, vitreous tissue, cells, and any other fluid or tissue or other material that may be present during a procedure in the eye (e.g. cataract procedure, vitrectomy procedures, and the like).

The systems, devices, and methods described herein are configured to apply vacuum and deliver fluids to maintain a pressure balance within the eye. The systems, devices, and methods described herein that apply vacuum and/or deliver fluids may also be configured to cut, fragment, emulsify, or otherwise make smaller material in and near the surgical site. The systems, devices, and methods described herein that allow for vacuum to be applied can provide that vacuum using pulsed vacuum with or without interspersed pulsed positive pressure to provide momentary retrograde flow.

The various features and functions of the devices described herein may be applied to one or more devices described herein even though they may not be expressly described in combination. It should also be appreciated that various features and functions of the devices described herein can be applied to conventional devices and systems known in the art also useful for cutting, fragmenting, emulsifying, or otherwise impacting tissues at or near a surgical site, including, but not limited to phacoemulsification systems, vitrectomy systems, bag polishing systems, and other tools useful in performing cataract surgeries or vitrectomy surgery, and the like.

Figure 1:
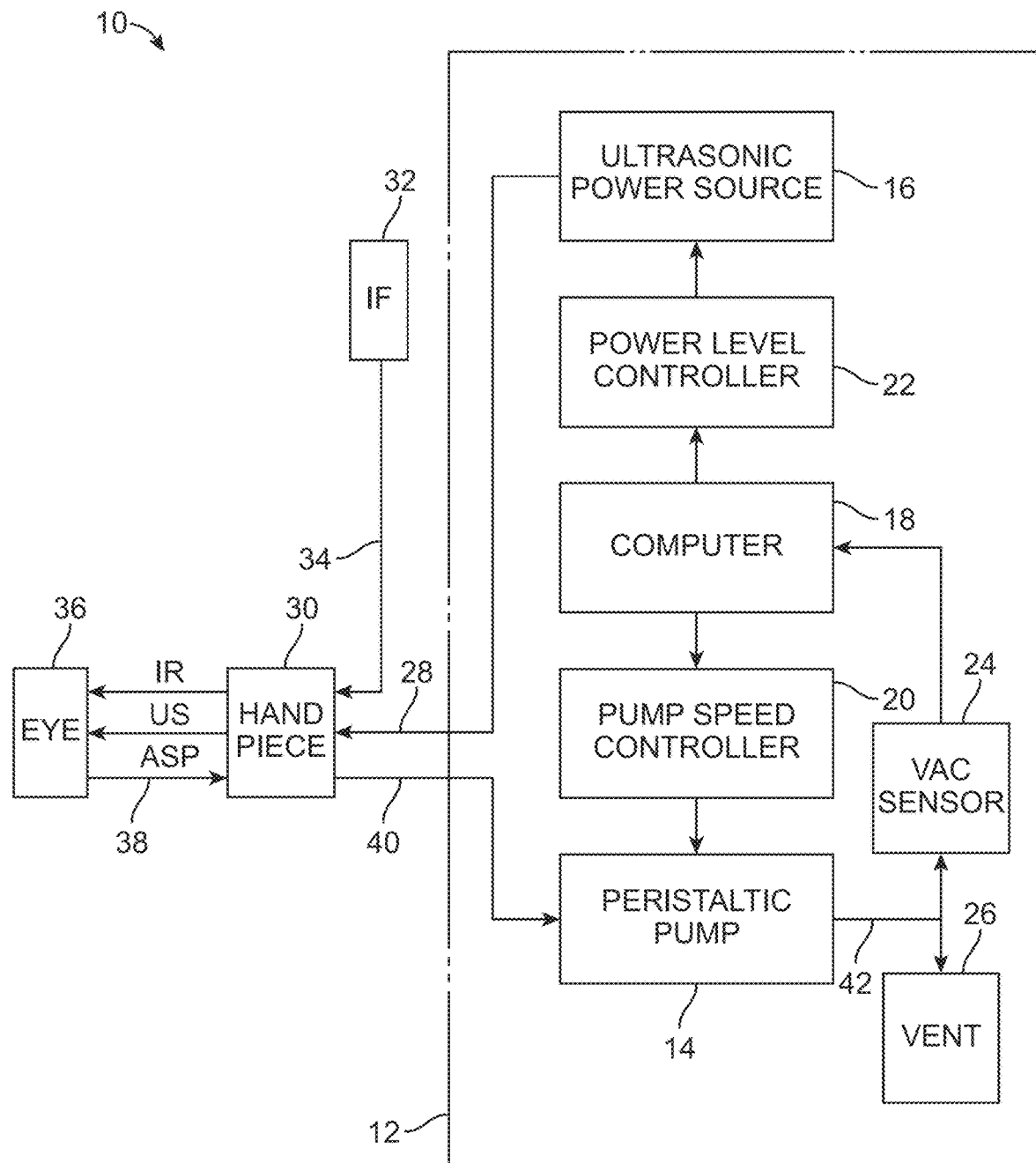
FIG. 1 is a block diagram of a phacoemulsification system.

FIG. 1 is a functional block diagram of a phacoemulsification system 10. The system 10 has a control unit 12, which can include a variable speed peristaltic pump 14, which provides a source of vacuum for aspiration, an ultrasonic power source 16, and a microprocessor computer 18 that provides control outputs to pump speed controller 20 and ultrasonic power level controller 22. A vacuum sensor 24 provides an input to computer 18 representing the vacuum level on the output side of the peristaltic pump 14. The vacuum sensor 24 may also be within the hand piece 30. Suitable venting is provided by vent 26. The control unit 12 supplies ultrasonic power on line 28 to a phacoemulsification hand piece 30. An irrigation fluid source 32 is fluidly coupled to hand piece 30 through line 34. The irrigation fluid and ultrasonic power are applied by hand piece 30 to a patient's eye 36. Aspiration of the eye 36 is achieved by peristaltic pump 14 through lines 38 and 40. Delivery of irrigation fluid from irrigation fluid source 32 can be provided via gravity or using an irrigation fluid pump additionally incorporated within the control unit 12. The computer 18 responds to preset vacuum levels in output line 42 from peristaltic pump 14 via signals from the vacuum sensor 24.

Figure 2A:
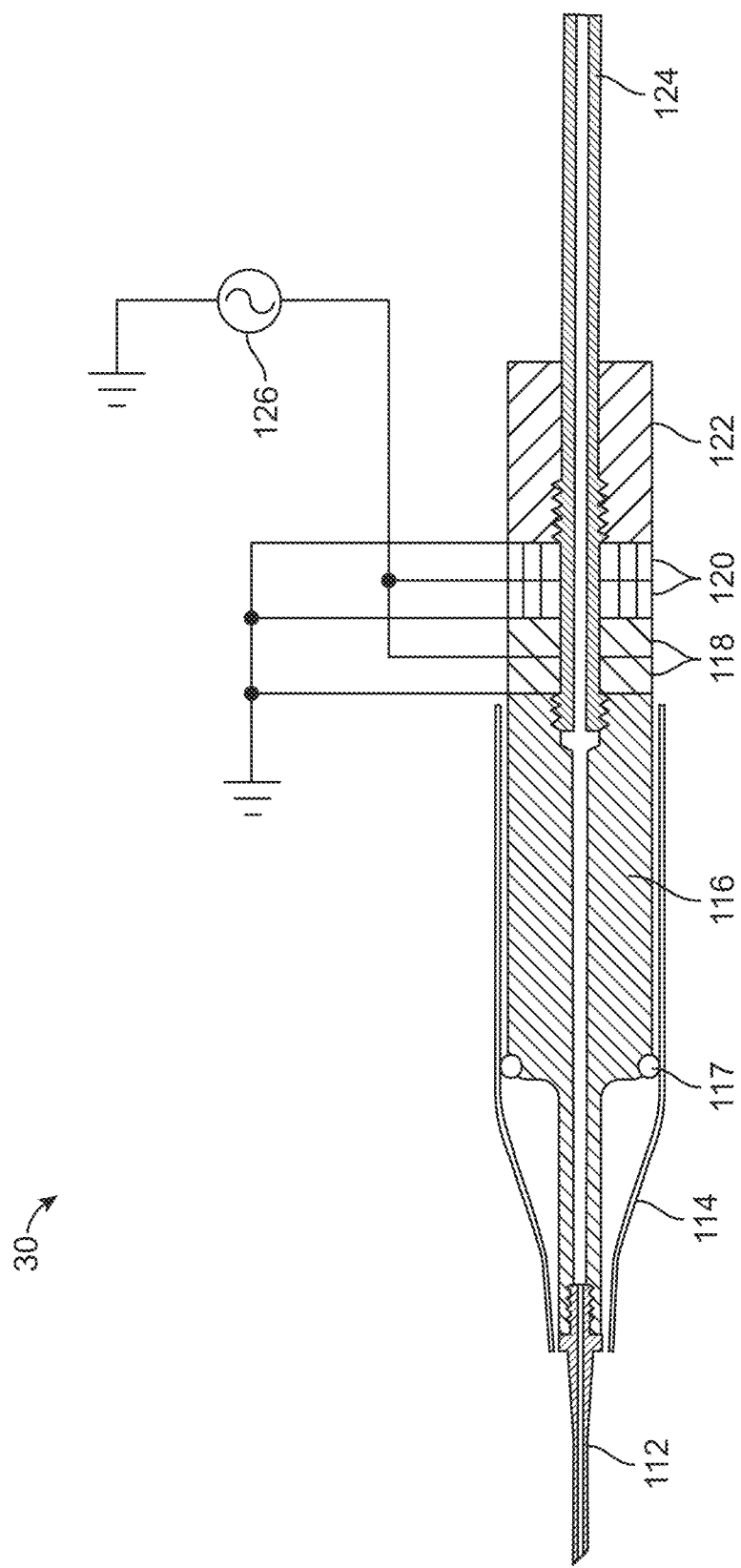
FIG. 2A is a cross-sectional view of a phacoemulsification hand piece.

FIG. 2A is a cross-sectional view of a phacoemulsification hand piece 30. The hand piece 30 has a cutting tip 112, which can be a tube having a lumen 110, hand piece shell 114, ultrasound horn 116, and a multi-stack of ultrasound crystals. The hand piece 30 can include a first set of ultrasound crystals 118 and a second set of ultrasound crystals 120. The first set of ultrasound crystals 118 may be arranged perpendicular to the longitudinal axis of the cutting tube 112 such that they produce what is conventionally referred to as "torsional" motion. The second set of ultrasound crystals 120 may be arranged coaxial with the longitudinal axis of the cutting tube 112 such that they produce what is conventionally referred to as "longitudinal" or "axial" motion. Crystals 118 are polarized to produce torsional motion. Torsional motion can include any of a variety of motions relative to the longitudinal axis of the cutting tube 112, but includes substantial side-to-side motion over axial motion. Crystals 120 are polarized to produce longitudinal motion. Longitudinal motion can also include any of a variety of motions of the cutting tube 112 relative to its longitudinal axis, but includes substantial axial motion over side-to-side. Crystals 118, 120 also may be configured to produce both longitudinal and torsional motion.

The ultrasound crystals need not be arranged perpendicular to the longitudinal axis of the cutting tube 112 in order to produce torsional motion, which will be described in detail below.

The horn 116 is held within the shell 114 by isolator 117. Crystals 118 and 120 are held within shell 114 and in contact with horn 116 by back cylinder 122 and bolt 124. Crystals 118 and 120 vibrate ultrasonically in response to a signal generated by an ultrasound generator 126. The ultrasound generator 126 provides the drive signal to power the ultrasonic hand piece 30.

Piezoelectric crystals generally have a resonant frequency where the input voltage corresponds to a maximum current and a maximum amplitude. This often occurs when the voltage and the current are in phase with one another. Ultrasonic drive systems that are described herein and also commonly used in ultrasonic welders, ultrasonic cutter, ultrasonic cleaners, etc., use the horn 116 to amplify the movement of the cutting tube 112. The horn length may be constructed to be a multiple of a half wavelength of the sound wave traveling through the horn material. Therefore the ends of the horn 116 are nodes that move at a maximum amplitude. The horn 116 is often stepped or constructed in a way to amplify the movement of the tube 112 by tapering such that the distal end of the horn 116 moves a greater distance than the proximal end of the horn 116, which is rigidly connected to the piezoelectric crystals 118, 120. The horn 116 is often designed to match the resonance of the piezoelectric crystal 118, 120 such that the most efficient energy transfer is achieved.

The cutting tube 112 of conventional phacoemulsification hand pieces are circular in cross-section. Torsional or transverse motion (i.e. substantially side-to-side motion relative to the longitudinal axis of the cutting tube 112) can create microscopic cavitation bubbles on the low pressure side (i.e. trailing side) of the circular cutting tube 112 that then implode when the direction of travel is reversed. The cutting tubes 112 described herein can incorporate a non-circular geometry configured to mitigate the creation of cavitation bubbles on one or both sides of the cutting tube 112 during the substantially side-to-side motion of the cutting tube 112 during torsional or transverse cutting motion. The non-circular geometry can include oval, elliptical, lentoid, teardrop, diamond, or other non-circular geometry. The geometry can include one or more airfoils or hydrofoils extending from a central axis of the cutting tube 112.

Figure 2C:
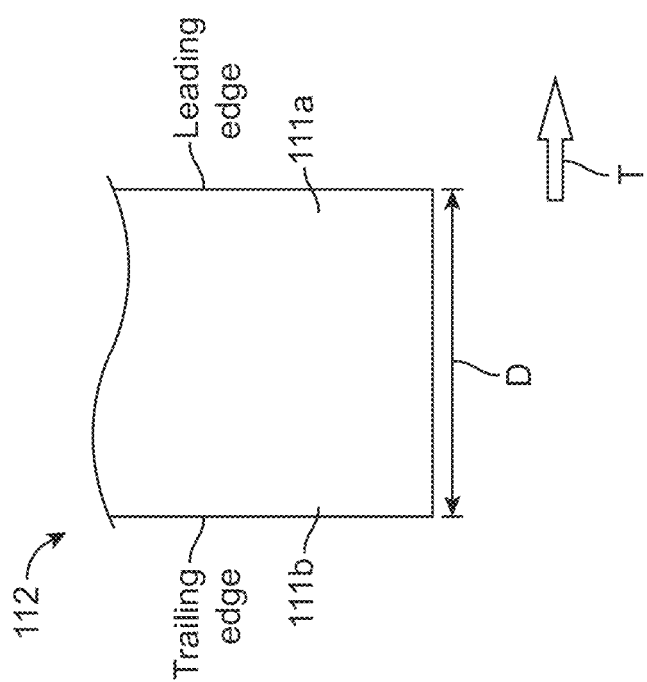
FIG. 2C is a planform view of the cutting tube of FIG. 2B.
Figure 2B:
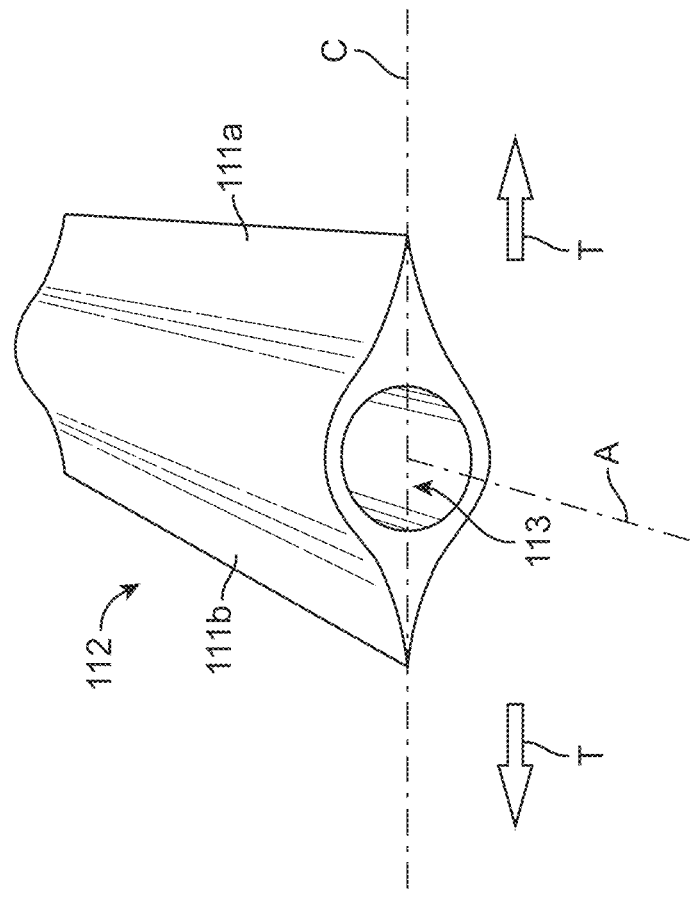
FIG. 2B is a distal-end perspective view of a cutting tube incorporating tapered profile geometry.

FIGS. 2B-2C show the cutting tube 112 of the hand piece 30 may include first and second tapers or tapered profiles 111*a*, 111*b* extending laterally from a central axis A of the tube 112. FIG. 2C shows the planform of the cutting tube 112 can be substantially rectangular along at least a portion of its length. The geometry of the cutting tube 112 can mitigate creation of these cavitation bubbles on the trailing, low pressure sides as the cutting tube 112 moves side-to-side. FIG. 2B shows a distal-end view of a substantially straight cutting tube 112. FIG. 2C is a planform view of the cutting tube 112 illustrating that when undergoing torsional motion toward right (arrow T) tapered profile 111*a* forms the leading edge and tapered profile 111*b* forms the trailing edge. The tapered profiles 111*a*, 111*b* extend outward from the lumen 113 on opposing sides of the longitudinal axis A of the cutting tube 112. The distance between the longitudinal axis A and the wing tip of the tapered profile 111 can vary between about 0.25 mm and about 1.5 mm or between about 0.5 mm and about 1.0 mm. As such, the distance D end-to-end between the tapered profiles 111*a*, 111*b* (i.e. wing span) can be between about 0.5 mm and about 3 mm or between about 1 mm and 2 mm. The aspect ratio of the winged cutting tube 112 can be relatively high (see FIG. 2E) or relatively low (see FIG. 2F). The aspect ratio of the winged cutting tube 112 can between 1.1 and 4. The cross-sectional geometry of the winged cutting tube 112 can incorporate substantially symmetrical tapered profiles 111*a*, 111*b* relative to the chord line C. Alternatively, the winged cutting tube 112 can incorporate a camber or have a curvature relative to the chord line C. The wing tip of each tapered profile 111 can be curved as shown in FIG. 2F or more angular as shown in FIG. 2G. The lumen 113 of the cutting tube 112 may be substantially cylindrical as shown in FIGS. 2B, 2D-2G or can have a non-circular geometry as shown in FIGS. 2H-2J such as elliptical, lentoid, oval, or other geometrical shape.

In some implementations, the tapered profile of the cutting tubes described herein can reduce or eliminate the amount of turbulent flow over the profile of the cutting tube, thereby increasing the amount of laminar flow as the tube moves as compared to a cutting tube having a circular profile. The cutting tubes described herein can incorporate surface treatments and/or coatings on an outer surface to further reduce the likelihood of or mitigate turbulent flow. For example, the cutting tube may be mechanically polished or buffed, electro-polished, plasma treated, coated with substances like PTFE, or any number of other suitable coatings or methods. Treatments and/or coatings may decrease the roughness of the cutting tube and/or reduce the friction of the fluid over the cutting tube such that portions of the cutting tube create laminar flow as the cutting tube travels through the fluid and decreased turbulent flow.

Figure 2K:
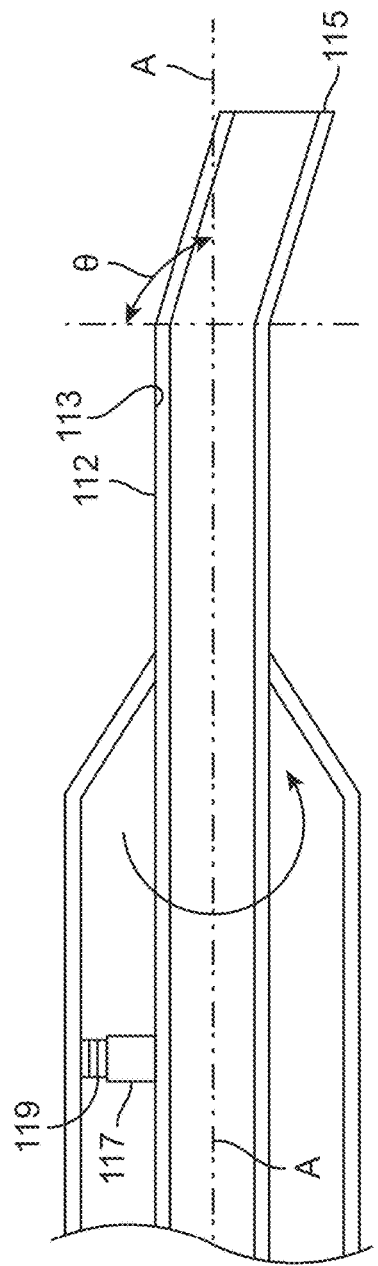
FIG. 2K is a cross-sectional schematic view of a Kelman style cutting tube.
Figure 2L:
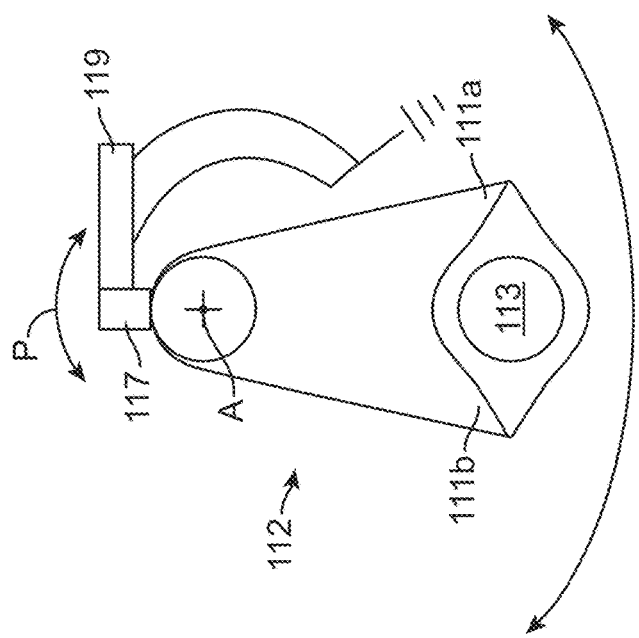
FIG. 2L is a distal-end view of the cutting tube of FIG. 2K incorporating tapered profile geometry.
Figure 2M:
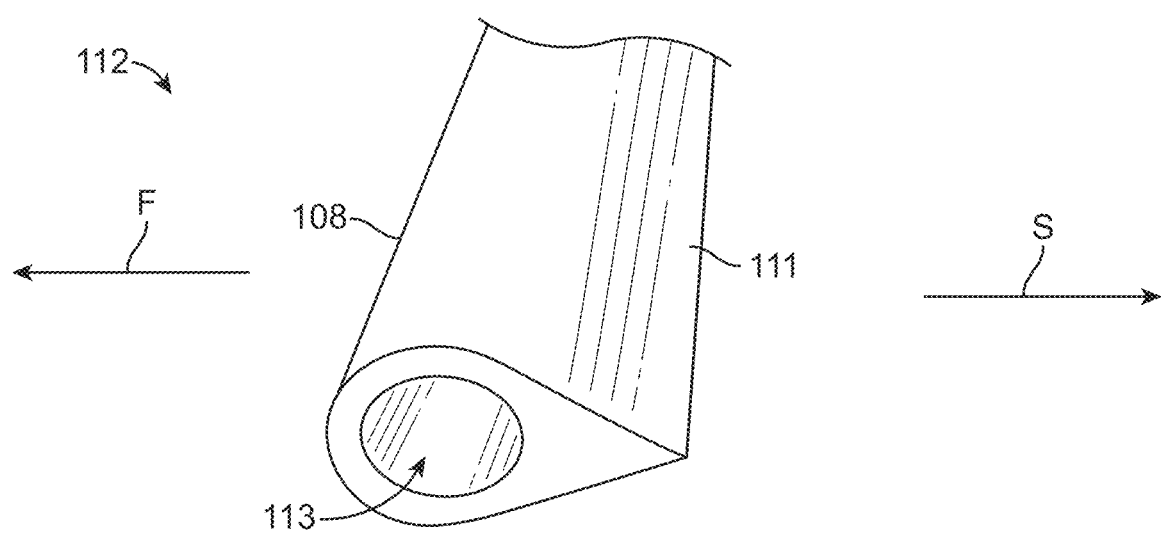
FIG. 2M is a distal-end perspective view of a cutting tube incorporating an asymmetric tapered profile geometry.

In some implementations, the cutting tube 112 can be asymmetric in cross-section (see FIG. 2M). The cutting tube 112 can have a single tapered profile 111 extending from only one side of the cutting tube 112 and the other side of the cutting tube 112 may have any of a variety of other geometries or profiles, including a circular profile 108. As will be described in more detail herein, motion of the cutting tube 112 may be asymmetric (e.g. speed or velocity of movement in a first direction can be different from speed or velocity of movement in a second, different direction). Torsional or side-to-side motion of the cutting tube 112 may be asymmetric such that the movement is optimize for the geometry of the cutting tube 112 (or the geometry of the cutting tube 112 is optimized for the movement). For example, as shown in FIG. 2M, one side of the cutting tube 112 has the tapered profile 111 and the other side does not and has instead a circular profile 108. The movement of the cutting tube 112 may be faster along direction arrow F when the circular profile 108 is the leading edge and the tapered profile 111 is the trailing edge compared to movement of the cutting tube 112 along direction arrow S when the tapered profile 111 is the leading edge and the circular profile 108 is the trailing edge. In this way, the trailing edge of the cutting tube 112 can be similar to a smooth hydrofoil having a tapered profile geometry when the cutting tube 112 is moving fast and the trailing edge of the cutting tube 112 can be circular in profile when cutting tube 112 is moving slowly. Thus, the geometry of the trailing edge together with the motion of the cutting tube 112 can be optimized to break up the lens tissue while still mitigating cavitation. The striking edge or leading edge profile of the cutting tube 112 may be a circular profile or any profile that optimizes striking and breaking apart lens pieces while the trailing edge can be optimized for reducing cavitation such as by incorporating a hydrofoil or tapered profile 111. Asymmetric motion of the cutting tube 112 allows each edge to be optimized for its respective purpose.

The winged geometry can be present from the distal-most end of the cutting tube 112 to a proximal-most end of the cutting tube 112. In some implementations, only a distal portion of the cutting tube 112 has the winged geometry. For example, only the distal-most 1 mm of the cutting tube 112 may be winged. The irrigation sleeve may be shaped at its distal end to conform to the shape of the tapered profile 111. Alternatively, the irrigation sleeve may be a standard circular shape, but may be positioned just proximal to the region of the tapered profile 111 at the distal end of the cutting tube 112.

The cutting tube 112 having the winged geometry can be straight along its longitudinal axis A as shown in FIGS. 2A-2B or may be bent or curved along at least a portion of its length. In some implementations, the cutting tube 112 may incorporate a Kelman-style tip (see FIGS. 2K-2L) having a bend forming an angle θ relative to the longitudinal axis A. The effect of a bent or curved tip is that the rotational displacement or side-to-side cutting motion at the distal-most tip 115 is larger compared to the relatively small rotational displacement of more proximal regions of the cutting tube 112 where the cutting tube 112 extends through the incision. When the cutting tube 112 is rotated about its longitudinal axis A, the distal-most tip of the cutting tube 112 sweeps back and forth along a greater distance. The sweeping distal tip of the cutting tube 112 can incorporate the tapered profiles 111a, 111b as best shown in FIG. 2L.

In some implementations, a tab 117 or other surface feature can be coupled to an outer surface of the cutting tube 112 a distance away from the distal-most tip 115. The tab 117 and the cutting tube 112 can be constrained such that it only moves in a rotational manner. A cutter tube drive mechanism 119, which can be piezoelectric, motor, electromagnetic, voice coil, or other drive mechanism configured to apply a force to tab 117 causing small rotational motions of the tab 117 and thus, the cutting tube 112. The cutting tube 112 can be constrained to move only torsionally. As an example, the cutter tube drive mechanism 119 can incorporate a piezoelectric crystal stack that pushes against the tab 117 urging it away from the stack. The crystal stack can be energized to push the tab 117 in a first direction and reverse energy moves the tab 117 back in the opposite direction (arrow P of FIG. 2L). In this configuration the piezoelectric crystal stack and the tab 117 may be fixed to one another. Other cutter tube drive mechanisms will be described in more detail below. The cutting tube 112 shown in FIG. 2L and incorporating the tab 117 is shown having a winged geometry. The geometry of the tube 112 need not incorporate these tapered profiles 111a, 111b and can be cylindrical.

It should be appreciated that any of the cutting tubes described herein can incorporate tapered profiles 111 such that the winged geometry may mitigate cavitation regardless the drive mechanism used to drive the torsional motion (i.e. piezo, voice coil, motor-driven cam, or other drive mechanism). Similarly, the winged cutting tube may be incorporated with any of a variety of hand pieces described herein including those hand pieces having an integrated aspiration pump and/or a trigger or finger-pedal on at least a portion of the hand piece.

Figure 3:
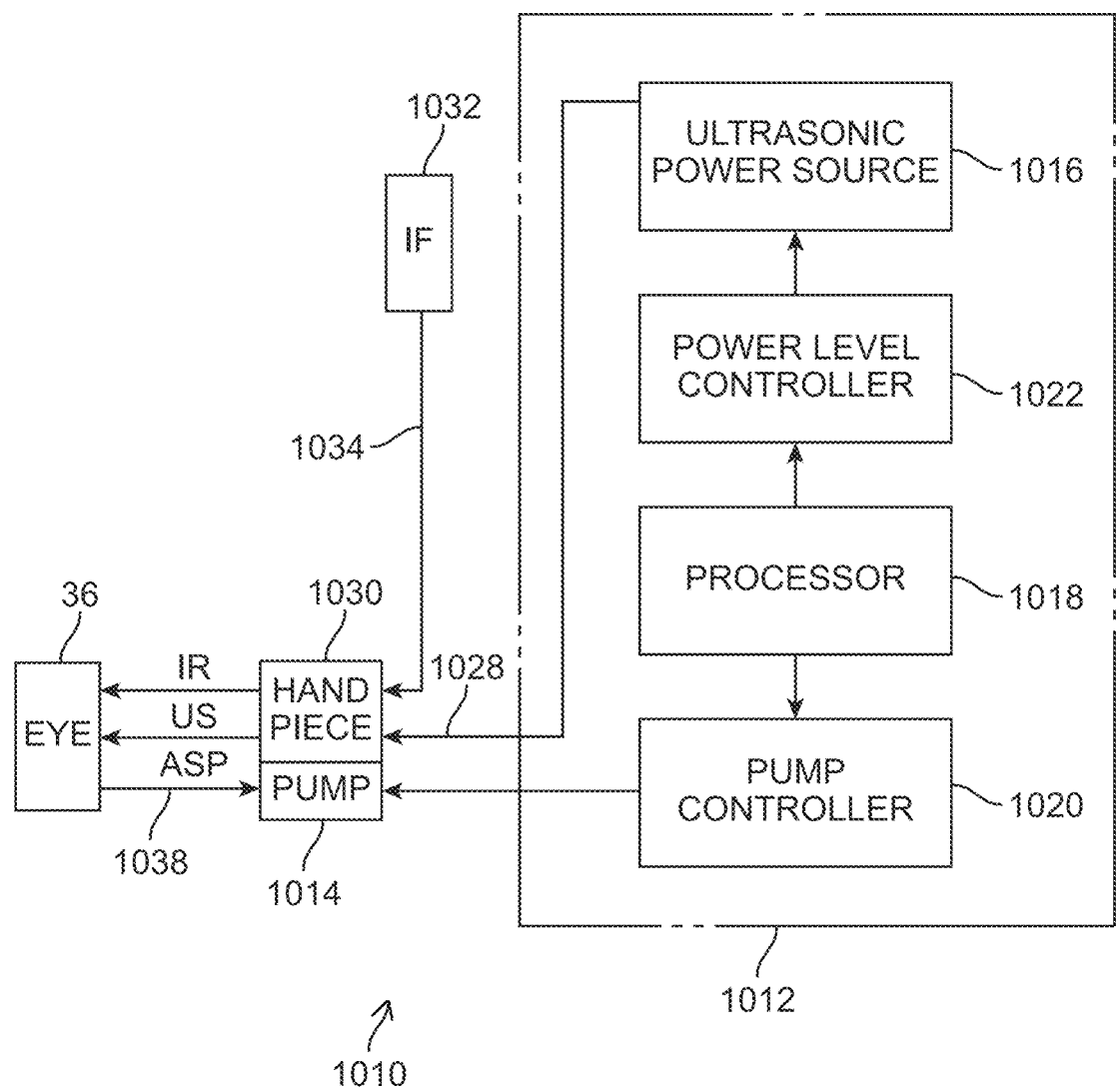
FIG. 3 is a block diagram of a phacoemulsification system according to an implementation including a hand piece with an integrated aspiration pump.

FIG. 3 is a functional block diagram of a phacoemulsification system 1010 according to an implementation. The system 1010 can include a control unit 1012, which can include an ultrasonic power source 1016 and a processor 1018 that provides control outputs to a pump controller 1020 and ultrasonic power level controller 1022. The control unit 1012 can supply ultrasonic power on line 1028 to a hand piece 1030 (e.g. 400V for driving piezoelectric crystals). The hand piece 1030 can include an integrated aspiration pump 1014 powered by the control unit 1012. The control unit 1012 can supply power to the aspiration pump 1014 of the hand piece 1030 via a line, which can be the same or a different line as line 1028 (e.g. lower voltage than for piezo, 5-12 V for driving a motor). It should appreciated that the hand piece 1030 can incorporate electronics such that the hand piece 1030 can be used independently of the control unit 1012. An irrigation fluid source 1032 can be fluidly coupled to the hand piece 1030 through irrigation line 1034. The irrigation fluid and ultrasonic power may be applied by the hand piece 1030 to a patient's eye 36. Aspiration of the eye 36 may be achieved by the aspiration pump 1014 in the hand piece 1030 through an aspiration line 1038. Delivery of irrigation fluid from irrigation fluid source 1032 can be provided via gravity and/or using an irrigation fluid pump within the control unit 1012.

Figure 4:
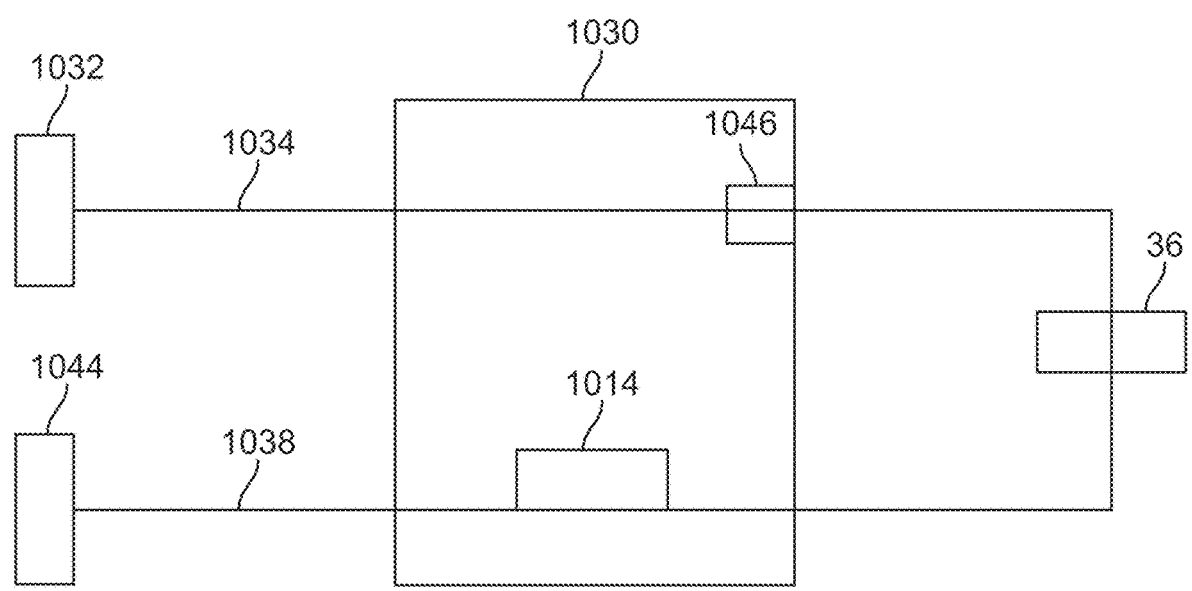
FIG. 4 is a block diagram of the phacoemulsification system of FIG. 3 illustrating the fluidics components.

FIG. 4 is a functional block diagram of the phacoemulsification system 1010 illustrating the fluidics of the system 1010. The fluidics of the system 1010 can include the irrigation fluid source 1032, the irrigation fluid line 1034, the aspiration pump 1014 within the hand piece 1030, a waste line 1038 (sometimes referred to herein as the aspiration line), and a waste container 1044. The system 1010 may optionally include an irrigation fluid pump configured to deliver irrigation fluid from the irrigation fluid source 1032. The irrigation fluid source 1032, which can optionally include one or more pressure sensors and/or valves for controlling flow through the irrigation line 1034, is fluidly coupled to the hand piece 1030, either directly or through the irrigation port 1044. Irrigation fluid may exit the irrigation fluid source 1032 and travel toward the hand piece 1030 through irrigation fluid line 1034 during a phacoemulsification procedure. An optional irrigation fluid reservoir 1046 may be incorporated within the distal end of the hand piece 1030, as will be described in more detail below. The hand piece 1030 and/or the irrigation line 1034 may optionally include one or more valves and/or sensors configured to provide additional control of fluid flow to the hand piece 1030. The hand piece 1030 and/or the waste line 1038 may optionally include one or more valves and/or sensors configured to provide additional control of fluid flow from the hand piece 1030. The pump 1014 may draw fluid and other materials from the eye 36 through waste line 1038 directing the material toward the waste container 1044.

The system 1010 can also include a remote aspiration pump within a region of the control unit 1012 in addition to the aspiration pump 1014 within the hand piece 1030. The aspiration pump in the control unit 1012 can be configured to apply continuous, semi-continuous, and/or discontinuous pulsatile aspiration. The aspiration pump in the control unit 1012 can be configured to apply a continuous low-level flow rate. The aspiration pump in the control unit 1012 can be any of a variety of different aspiration pumps including volumetric flow or positive displacement pumps (e.g. peristaltic, linear peristaltic, piston, scroll pump) or vacuum-based pumps (e.g. venturi, pneumatic, diaphragm, or rotary-vane). In an implementation, the aspiration pump in the control unit 1012 can include a low pressure, peristaltic pump integrated within the control unit 1012 to support the aspiration provided by the integrated aspiration pump 1014 within the hand piece 1030. For example, during a first portion of use, aspiration through the hand piece 1030 may be provided by the remote aspiration pump within the control unit 1012 and during a second portion of use, aspiration through the hand piece 1030 may be provided by the integrated aspiration pump 1014 within the hand piece 1030. Additional implementations of the aspiration support are described in more detail below.

Figure 5A:
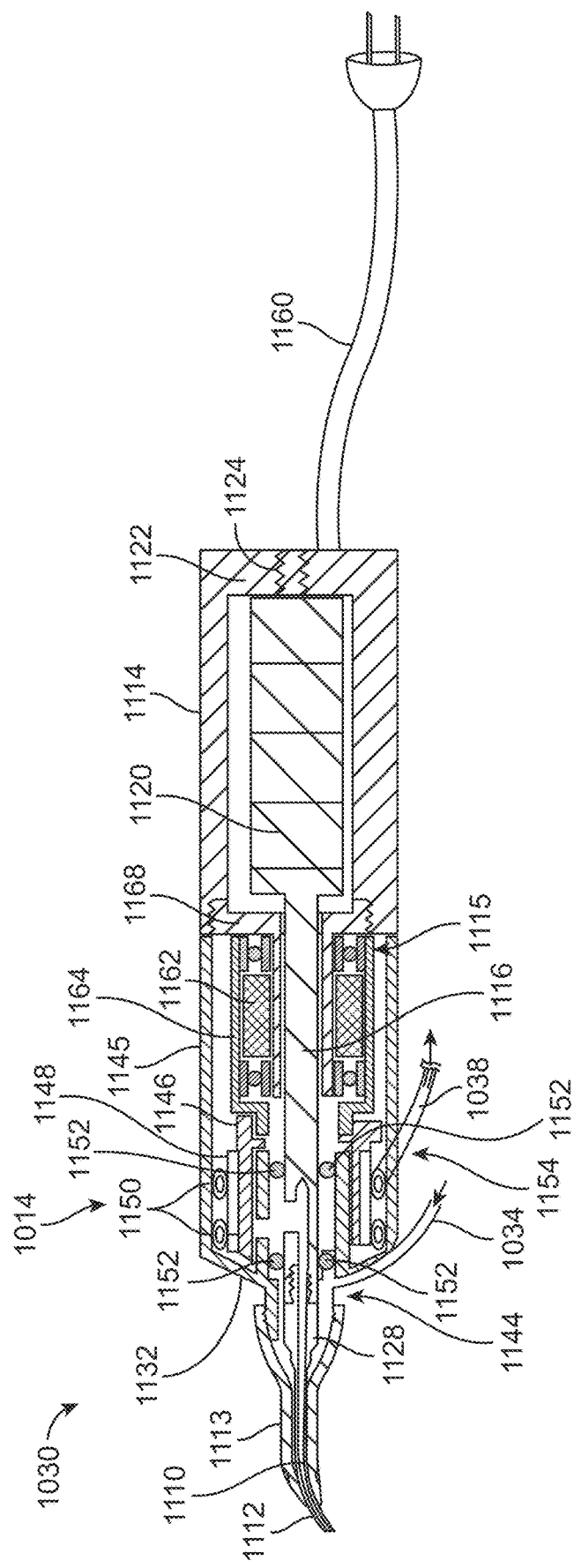
FIG. 5A shows an implementation of a hand piece of FIG. 3.
Figure 5B:
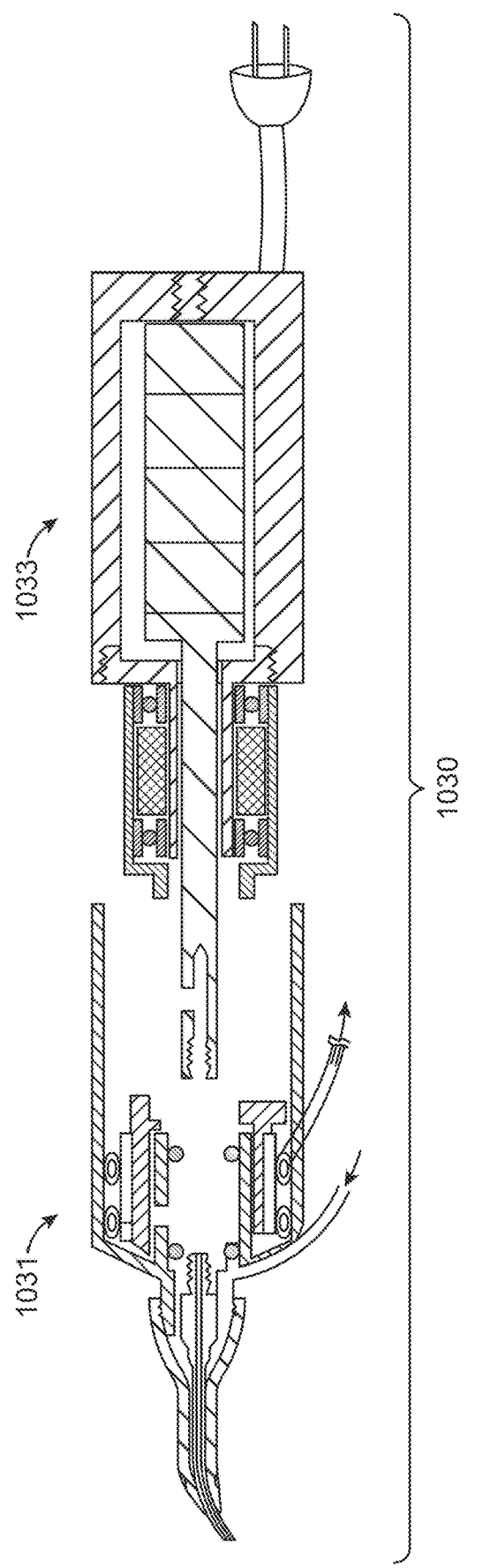
FIG. 5B shows the hand piece of FIG. 5A with the durable portion removed from the disposable portion.

FIGS. 5A-5B are cross-sectional views of an implementation of the hand piece 1030 of FIG. 3 having the aspiration pump 1014 driven by pump motor 1115. The hand piece 1030 is configured for surgeries (such as cataract surgeries) that are performed in a minimally-invasive, ab interno approach through clear corneal incisions. The hand piece 1030 requires less energy, time, and fluid to remove the tissues from the eye than conventional phaco.

The hand piece 1030 includes a hollow cutting tip or cutting tube 1112 reciprocated by a cutter tube drive mechanism. The cutting tube 1112 can be oscillated by any of a variety of drive mechanisms including the piezoelectric drive mechanisms described above as well as electric, magnetostrictive, electromagnetic, hydraulic, pneumatic, mechanic, voice coil, or other type of drive mechanism known in the art. Where the cutting tube 1112 is described as being oscillated by a piezoelectric drive mechanism is should be appreciated that other cutter tube drive mechanisms are considered as well. In some implementations, the cutting tube 1112 is reciprocated by a drive mechanism including a motor contained within an interior of the hand piece 1030. The configuration of the motor can vary including, any of a variety of rotation motors, stepper motor, AC motor, DC motor, a piezoelectric motor, a voice coil motor, or other motor. The motor may be coupled to a gear reduction system such as a harmonic drive to produce the desired output speed.

In an implementation, the cutting tube 1112 is oscillated by a piezoelectric drive mechanism. The cutting tube 1112 may be coupled to a horn 1116 driven by piezoelectric crystals 1120. The crystals 1120 may be held within the housing 1114 in contact with the horn 1116 by a back cylinder 1122 and bolt 1124. The crystals 1120 may be polarized to produce longitudinal and/or torsional motion when a drive signal is provided to power the hand piece 1030 by the control unit 1012. The piezoelectric crystals 1120 may be natural piezoelectric substrates, such as quartz single crystals, piezoelectric ceramics, such as lithium niobate, gallium arsenide, zinc oxide, aluminum nitride, or lead zirconate-titanate (PZT). In some implementations, the piezoelectric crystals 1120 are formed of polymer-film piezoelectrics, such as polyvinylidene fluoride. Such plastic-based crystal stacks may be lower cost and potentially disposable.

Conventional ultrasound horns are configured to augment the oscillation displacement amplitude provided by the piezoelectric crystals. Conventionally, the horn is rigidly connected to the ultrasonic transducer using a threaded stud at a proximal end and tapers distally. Conventional ultrasound horns are resonant. "Horn" as used herein can, but need not function as a conventional ultrasound horn does. Meaning, the horn can, but need not, be in resonance during use. The horn described herein can be used in a non-resonant, direct drive manner as will be described in more detail herein. Use of the term "horn" herein is not intended to be limiting to the conventional use of the term ultrasound horn.

The cutter tube drive mechanisms described herein can incorporate a piezoelectric stack. Piezos can suffer damage and cracking when misaligned with other components. Stacks of disc-shaped piezos are less prone to damage because they can be arranged fully parallel to one another. However, the piezoelectric stacks described herein can be arranged in non-concentric manner relative to the cutting tube and can directly drive motion of various components that are not necessarily arranged completely parallel. Meaning, if any angularity exists at the interface with the piezoelectric stack, the point loads can lead to cracking.

The piezoelectric stack can be a multilayer of thin piezoelectric/electrostrictive ceramic sheets stacked together. These multilayers have a relatively low driving voltage (100 V), quick response, high generative force, and high electromechanical coupling. The displacement though is usually on the order of 10 microns and is generally not sufficient alone for cutting tube displacement. As mentioned above, the motion of the cutting tip can be what is known as "torsional" or primarily side-to-side motion over longitudinal, forward-backward motion. This tip motions is considered to be more efficient lens removal motion, particularly for dense and hard lens nuclei. Regardless the direction or orientation of the motion of the cutting tip, a primary goal in piezoelectric drive mechanisms is amplification of the tiny motion of the piezoelectric material into sufficient physical displacement or stroke of the cutting tip.

Described herein are various interrelated implementations of cutter tube drive mechanisms configured to achieve a minimum tip speed of 3 meters/second and within a frequency range that is less than ultrasonic (i.e., less than 20,000 Hz), including less than 10,000 Hz, less than 5,000 Hz, less than 4,000 Hz, less than 3,000 Hz down to sub-sonic frequency ranges that are less than 20 Hz, less than 15 Hz, less than 10 Hz, less than 5 Hz, down to about 0.5 Hz. In some implementations, the tip speed target is approximately 5 meters/second to ensure cutting of denser material. The cutter tube drive mechanisms are capable of amplifying motion of the cutting tube while mitigating the likelihood of damage due to the incorporation of movable components. The cutter tube drive mechanism can incorporate a piezoelectric stack or motor driven cam or vibrating motor that directly drives the cutting tube via a conventional hinge to generate oscillatory motion. The oscillatory motion achieved can be in the frequency range that is less than ultrasonic. The drive mechanism can incorporate less than 2 nodal inflection points between a point of drive force application and the distal tip of the cutting tube. The drive force can be applied to generate longitudinal motion as well as side-to-side ("torsional") motion. It should be appreciated that the torsional motion need not be constrained to a single plane. The drive mechanism can also drive the cutting tube via a "living" hinge to generate the oscillatory motion.

FIGS. 16A-16D illustrate an implementation of a cutter tube drive mechanism 119 incorporating a conventional or mechanical hinge coupled to a rocker arm or rocker plate. The rocker 1605 can be an off-set rocker 1605. The cutter tube drive mechanism 119 can include a base 1610 configured to couple to or be integrated with an interior of the hand piece (not shown). The rocker 1605 can be movably attached to the base 1610 via a rocker pivot pin 1615, which allows the rocker 1605 to freely rotate relative to the base 1610 about the rotational axis of the pivot pin 1615. A piezoelectric stack 1120 can be coupled to the base 1610 on a lower end and the rocker 1605 on an upper end. The cutting tube 1112 can extend through generally central regions of the base 1610 and the rocker 1605. The piezoelectric stack 1120 can be positioned off-set or on one side of the base 1610. The piezoelectric stack 1120 can be coupled to the base 1610 and the rocker 1605 via movable couplings. For example, the cutter tube drive mechanism can incorporate a pair of toggles 1620a, 1620b. The lower toggle 1620a can be attached to the base 1610 via a lower toggle pin 1622 and the upper toggle 1620b can be attached to the rocker 1605 via an upper toggle pin 1624. The toggles 1620a, 1620b can freely rotate relative to the base 1610 and the rocker 1605. This motion allows for some degree of non-paralellism to exist between the proximal end of the piezoelectric stack 1120 where it contacts the base 1610 and the distal end of the piezoelectric stack 1120 where it contacts the rocker 1605 thereby mitigating damage at the edges of the piezoelectric stack 1120. The pivot of the toggles 1620a, 1620b allow for misalignment and cancels out any inaccuracies in the parallel to non-parallel motion transfer. Additionally, a dome 1621 may be positioned near the interface with the piezoelectric stack 1120 to eliminate any point loads (see FIG. 16D).

The cutter tube drive mechanism 119 can include a spring post 1625 and a spring stack 1627. As mentioned above, the cutting tube 1112 can extend through the central region of the base 1610 and rocker 1605. The piezoelectric stack 1120 can be positioned off-set or on one side of the base 1610. The spring post 1625 and spring stack 1627 can be positioned opposite the piezoelectric stack 1120 such that the cutting tube 1112 is positioned between the piezoelectric stack 1120 positioned on one side of and the springs on the opposite side.

The spring stack 1627 can be one or more Belleville springs encircling a boss 1638 on an upper end region of the spring post 1625 (see FIG. 16C). The boss 1638 of the spring post 1625 can extend at least partially into a hole 1637 through the rocker 1605. The spring post 1625 can also include a lower boss 1638 configured to mate with a corresponding hole on the base 1610. The bosses 1638 on the spring post 1625 can freely slide axially within the holes 1637 on the rocker 1605 and the base 1610. The bosses 1638 can keep the spring stack 1627 contained in the desired position on the spring post 1625.

An upper surface of the spring stack 1627 engages with a lower surface of the rocker 1605 and a lower surface of the spring stack 1627 abuts against a ledge of the spring post 1625. The spring stack 1627 can apply a upwardly-directed force against the lower surface of the rocker 1605. The force on the rocker 1605 can be transmitted as a pre-load onto the upper end of the piezoelectric stack 1120 via the toggles 1620a, 1620b. Pre-load ensures constant contact is maintained between the piezoelectric stack 1120 and other components parts so no motion of the piezoelectric stack 1120 is lost.

The cutting tube 1112 can extend through a bore in the rocker 1605 and through a bore in the base 1610. The cutting tube 1112 can be fixed to each via glue, welding, or other method of fixation. A support bushing 1630 can be incorporated that aids in preventing the tube from cracking after prolonged use. The support bushing 1630 can be coupled to an upper surface of the rocker 1605 aligned with the bore through the rocker 1605. FIG. 16C shows a side section view of the off-set rocker 1605. The tube 1112 is shown attached to the base 1610 via a stiffener bushing 1635. The stiffener bushing 1635 can ensure that the tube 1112 is forced to bend relative to the base 1610 when the piezoelectric stack 1120 is activated.

The piezoelectric stack can change with varying voltage including alternating current or DC variable voltage. In an implementation, an alternating current (e.g., 100 Hz to 20 Khz) applied to the piezoelectric stack 1120 causes the piezoelectric stack 1120 to expand and contract. As the piezoelectric stack 1120 expands, the rocker 1605 and therefore the tube 1112 attached to the rocker 1605 can bend about the base 1610. As the piezoelectric stack 1120 contracts, the spring stack 1627 can assist the piezoelectric stack 1120 in quickly returning to its starting length and ensure there is constant contact between the piezoelectric stack 1120 and the two toggles 1620a, 1620b. The cutting tube 1112 can undergo bending where it extends through the rocker 1605. There also can be some bending of the tube 1112 below the rocker 1605 and additional motion due to the "whipping". The cutting tip motion is generally much larger than what is predicted for the piezoelectric stack 1120 due to the presence of additional "whipping" motion by the cutting tube 1112. The piezoelectric stack 1120 incorporated in the cutter tube drive mechanisms described herein can be mechanically configured to use any piezoelectric charge coefficient, i.e., $d_{33}$, $d_{31}$, $d_{15}$.

Figure 17C:
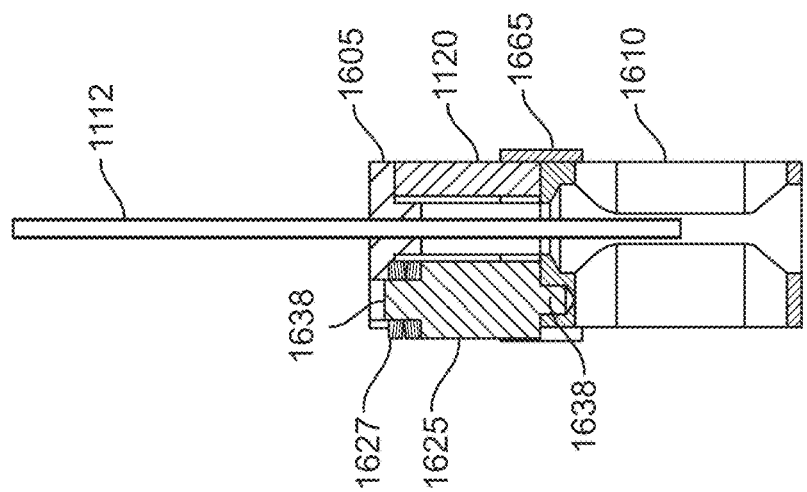
FIGS. 17B-17C are side and cross-sectional views, respectively, of the cutter tube drive mechanism of FIG. 17A.
Figure 17B:
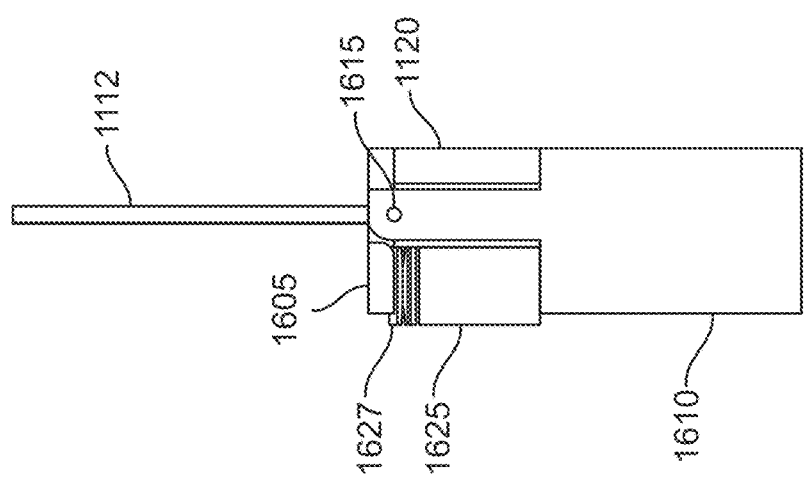
Figure 17A:
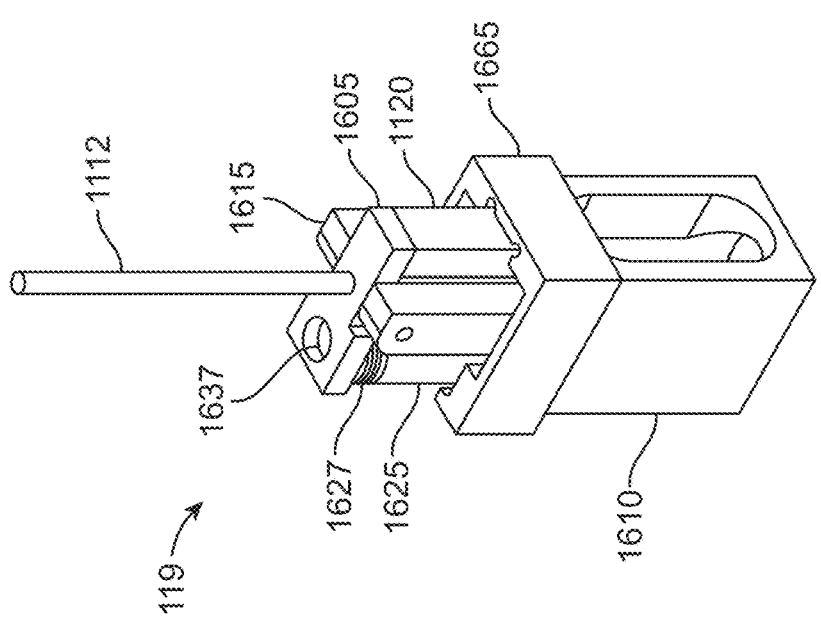
FIG. 17A illustrates an implementation of a cutter tube drive mechanism incorporating a straight rocker.

FIGS. 17A-17C illustrate an interrelated implementation of a cutter tube drive mechanism 119 incorporating a conventional or mechanical hinge coupled to a rocker arm or rocker plate. The rocker can be a straight rocker 1605. The straight rocker 1605 can be movably attached to the base 1610 via a rocker pivot pin 1615, which allows the rocker 1605 to freely rotate relative to the base 1610 about the rotational axis of the pivot pin 1615. The location of the hinge (i.e., rocker pivot pin 1615 shown in FIGS. 17A-17C) is further towards a distal end of the cutting tube 1112 compared to the location of the hinge in the offset rocker implementation shown in FIGS. 16A-16C. The rocker pivot pin 1615 in the straight rocker 1605 can be substantially aligned along the longitudinal axis of the tube 1112 and the rocker 1605 creating a fulcrum for the rocker 1605 The location of the rocker pivot pin 1615 relative to the tube 1112 may change the wag characteristics at the tip of the tube 1112 and may alter the "whipping" effect the tube 1112 exhibits during use. In the straight rocker, the pivot pin is substantially aligned with the rocker along the longitudinal axis of the cutter tube. In the offset rocker, the pivot pin is positioned proximal to the rocker along the longitudinal axis of the cutter tube.

The piezoelectric stack 1120 can be coupled to the base 1610 on a lower end and to the rocker 1605 on an upper end. The cutting tube 1112 can extend through a generally central regions of the base 1610 and the rocker 1605. The piezoelectric stack 1120 can be positioned off to one side of the base 1610. The piezoelectric stack 1120 can be attached to the base 1610 and rocker 1605 or unattached. The interfaces can incorporate one or more features that mitigate damage and point loads to the piezoelectric stack 1120 as described elsewhere herein.

The cutter tube drive mechanism 119 can include a spring post 1625 and a spring stack 1627 positioned opposite the piezoelectric stack 1120 such that the cutting tube 1112 is positioned between the piezoelectric stack 1120 and the springs. The tube 1112 can run through the rocker 1605 and the base 1610 and as described above, be attached or unattached to the rocker 1605 and base 1610. The spring stack 1627 is compressed when in a resting state thereby applying an upward force to a first end the rocker 1605 and a preload force to the piezoelectric stack 1120 applied by a second, opposite end of the rocker 1605. As the piezoelectric stack 1120 expands or grows under varying voltage, it rotates the rocker 1605 about the rotational axis of the pivot pin 1615 on the base 1610 and thereby moves or "wags" the tube 1112 in at least one direction. As the piezoelectric stack 1120 retracts the upward force applied by the spring stack 1627 against the first end of the rocker 1605 urges the second, opposite end of the rocker 1605 downward with the retracting piezoelectric stack 1120. The rocker 1605 rotates in the opposite direction, wagging the tube 1112 in the opposite direction. The spring stack 1627 can force the rocker 1605 to rotate and maintain contact with the end of the piezoelectric stack 1120.

The cutter tube drive mechanism 119 can include a piezoelectric stabilizer 1665. The piezoelectric stabilizer 1665 can surround where the piezoelectric stack 1120 and spring post 1625 contact the base 1610 to ensure the piezoelectric stack 1120 does not work its way out of position during operation. Any of the implementations described herein can incorporate a piezoelectric stabilizer 1665.

Figure 18:
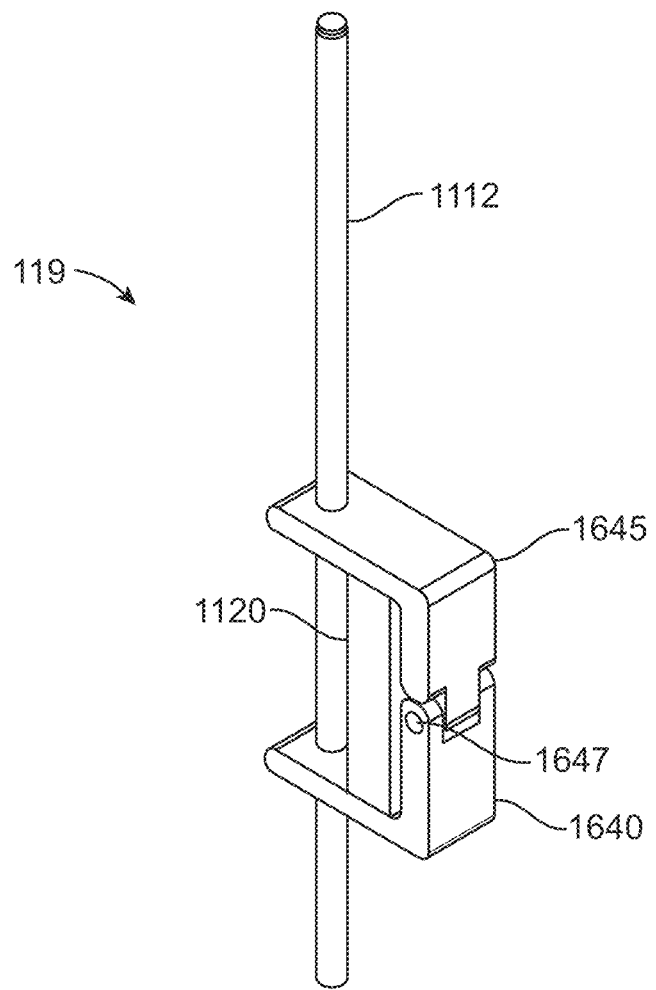
FIG. 18 is a perspective view of an implementation of a cutter tube drive mechanism incorporating a hinge clamp.

FIG. 18 illustrates an interrelated implementation of a cutter tube drive mechanism 119 incorporating a hinge clamp. The hinge clamp can include a lower clamp 1640 and an upper clamp 1645. The tube 1112 can be inserted through the holes on the upper clamp 1645 and lower clamp 1640. The lower clamp 1640 may be rotatably attached to the upper clamp 1645 via a hinge pin 1647. The lower clamp 1640 may be attached to the handle (not shown). The piezoelectric stack 1120 can fit in between the upper clamp 1645 and the lower clamp 1640. The piezoelectric stack 1120 can either be attached or unattached to the clamps 1640, 1645 as described elsewhere. During installation, a clamping force can be applied to the upper clamp 1645 and lower clamp 1640 forcing them to apply a preload force to the piezoelectric stack 1120 positioned therebetween. With the preload force applied, the tube 1112 can be attached to the upper and lower clamps 1645, 1640 such that when the clamping force is removed, the preload force is transferred to the tube 1112 and maintained on the piezoelectric stack 1120. As the piezoelectric stack 1120 grows, it rotates the upper clamp 1645 about the hinge pin 1647 and thereby wags the tube 1112 in one direction. As the piezoelectric stack 1120 retracts, the upper clamp 1645 rotates in the opposite direction, wagging the tube 1112 in the opposite direction. The preload carried in the tube 1112 ensures that the upper clamp 1645 retracts and maintains constant contact with the piezoelectric stack 1120. Additional clamping can ensure constant contact between the piezoelectric stack 1120 and other components, for example, on a portion of the upper and lower clamps 1645, 1640 on an outside region of the tube opposite the hinge pin 1647.

Figure 19C:
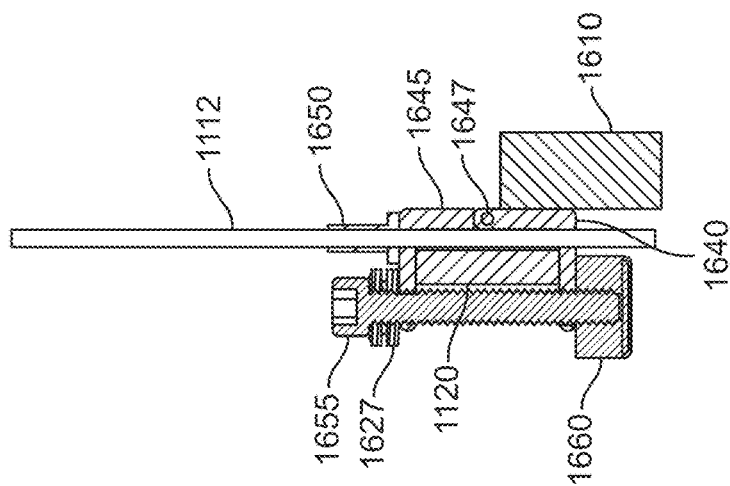
FIGS. 19B-19C are side and cross-sectional views, respectively, of the cutter tube drive mechanism of FIG. 19A.
Figure 19B:
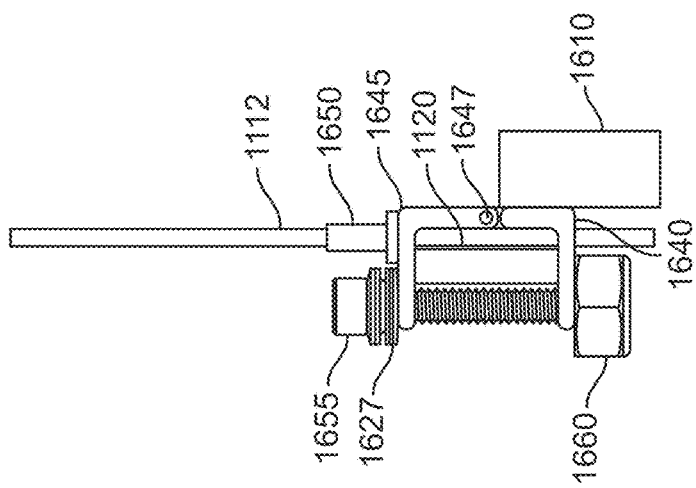
Figure 19A:
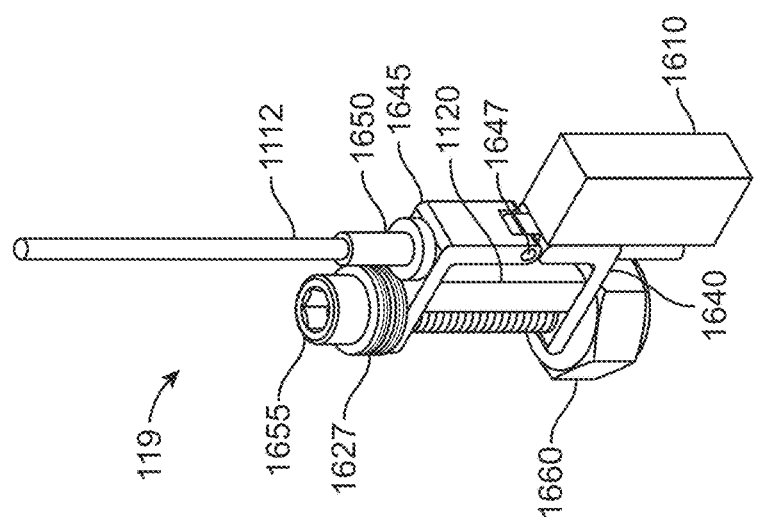
FIG. 19A illustrates an implementation of a cutter tube drive mechanism incorporating a parallel Belleville spring.

FIGS. 19A-19C illustrate an interrelated implementation of a cutter tube drive mechanism 119 also incorporating a hinge clamp. It should be appreciated that the various drive mechanisms described herein may incorporate one or more features of any other drive mechanism described herein even though that feature may not be explicitly described for a particular implementation. The hinge clamp can include a lower clamp 1640 and an upper clamp 1645. The lower clamp 1640 can be attached to the base 1610 via glue, welding, or other coupling means. The upper clamp 1645 can be attached to the lower clamp 1640 via the hinge pin 1647 such that the upper clamp 1645 is free to rotate about the hinge pin 1647. The piezoelectric stack 1120 can fit in between the upper clamp 1645 and the lower clamp 1640.

The cutting tube 1112 can run through both the upper clamp 1645 and lower clamp 1640. The cutting tube 1112 can be attached to the upper and lower clamps via glue, welding, or other attachment although the tube 1112 need not be mechanically coupled. A support bushing 1650 can slip around the tube 1112 or be attached to the cutting tube 1112 as described elsewhere.

The cutter tube drive mechanism 119 can include a spring stack 1627 and a preload screw 1655. The preload screw 1655 can be arranged parallel to the cutting tube 1112. The preload screw 1655 can run through the upper clamp 1645 and lower clamp 1640 and be threaded into a preload nut 1660 below the lower clamp 1640. The spring stack 1627, which can include Belleville springs, can be captured between the head of the preload screw 1655 and the upper surface of the upper clamp 1645. As the preload screw 1655 is tightened into the preload nut 1660 below the lower clamp 1640 during installation, the screw head compresses the spring stack 1627 against the upper clamp 1645. This, in turn, applies a preload force onto the piezoelectric stack 1120 positioned between the upper and lower clamps 1645, 1640.

The piezoelectric stack 1120 and the preload screw 1655 can be positioned on the same side relative to the location of the cutting tube 1112 in contrast to the implementation shown in FIGS. 16A-16C in which the piezoelectric stack 1120 and the preload mechanism are located on opposite sides relative to the location of the cutting tube 1112. An upper surface of the piezoelectric stack 1120 can engage a lower surface of the upper clamp 1645 and a lower surface of the piezoelectric stack 1120 can engage an upper surface of the lower clamp 1640 such that the piezoelectric stack 1120 is positioned and clamped between the upper and lower clamps 1645, 1640. The piezoelectric stack 1120 can be fixed to the upper and lower clamps 1645, 1640 via glue or other mechanical fixation.

As the piezoelectric stack 1120 grows, the upper clamp 1645 can be forced upwards. The upper clamp 1645 rotates about the hinge pin 1647 and compresses the spring stack 1627 against the head of the preload screw 1655. As the piezoelectric stack 1120 retracts, the spring stack 1627 forces the upper clamp 1645 downwards around the axis of the hinge pin 1647 maintaining constant contact against the upper end of the piezoelectric stack 1120. The preload screw 1655 allows for the amount of preload to be dialed in and adjusted during manufacturing to achieve the desired load.

Figure 20A:
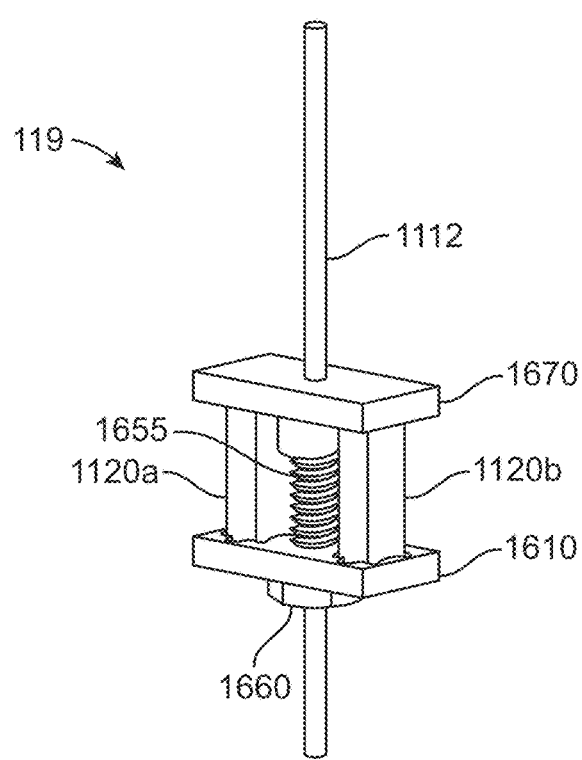
FIG. 20A illustrates an implementation of a cutter tube drive mechanism.
Figure 20B:
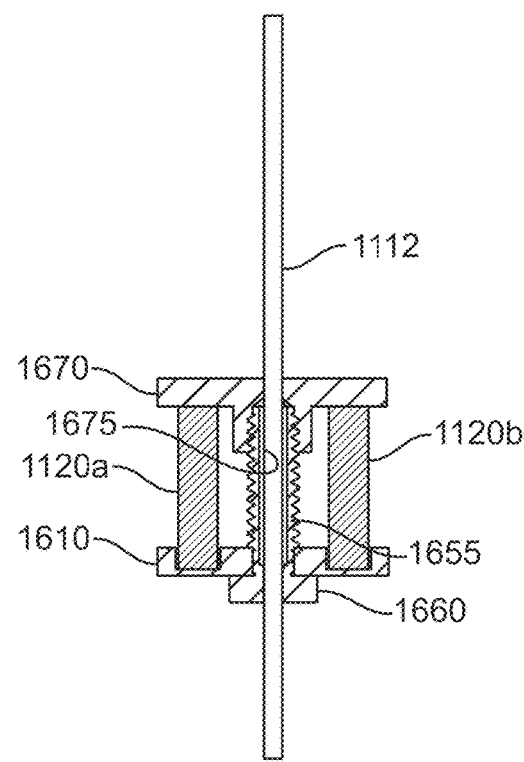
FIG. 20B is a cross-sectional view of the cutter tube drive mechanism of FIG. 20A.

FIGS. 20A-20B illustrate an interrelated implementation of a cutter tube drive mechanism 119 incorporating a biplane configuration. The drive mechanism 119 can include a base 1610, a top plate 1670, and two intervening piezoelectric stacks 1120a, 1120b. The two piezoelectric stacks 1120a, 1120b can either be unattached or attached to the top plate 1670 and base 1610. FIG. 20B shows the two piezoelectric stacks 1120a, 1120b can fit into pockets on the base 1610 to control the position of the piezos. The drive mechanism 119 can additionally include a preload screw 1655 and nut 1660. The screw 1655 can extend through the base 1610 and into corresponding threads available from a lower surface of the top plate 1670. As the preload screw 1655 is tightened, a preload force is applied to the piezoelectric stacks 1120a, 1120b via the top plate 1670. The tube 1112 can run through the top plate 1670 and through a central bore 1675 in the preload screw 1655 (see FIG. 20B). The tube 1112 may be unattached or attached to the top plate 1670 and preload screw 1655. As mentioned elsewhere herein, the piezoelectric stack can change with varying voltage. In an implementation, two separate alternating currents can be applied to the piezoelectric stacks 1120a, 1120b. The alternating currents may be out of phase such that one piezoelectric 1120a expands as the other piezoelectric 1120b retracts and vice versa. This can allow the top plate 1670 to pivot or rock thereby causing the tube 1112 to wag back and forth. The alternating currents can also be timed to one another in any manner that creates a desirable effect on the end of the tube 1112.

The drive mechanisms described above are configured to provide torsional motion to the cutting tube with a minimum peak tip velocity (e.g., at least 2.5 meters/second, but less than about 12 m/s). In any of the implementations described herein, the piezoelectric stack 1120 can be stacked parallel to the longitudinal axis of the tube 1112 (i.e., a vertical stack) or can be stacked perpendicular to the tube. Whether stacked parallel or perpendicular to the tube 1112, the direction of elongation can be the along the longitudinal axis of the tube 1112. The piezoelectric stack 1120 can be mechanically configured to use any piezoelectric charge coefficient including as examples $d_{33}$, $d_{31}$, and $d_{15}$.

Figure 21A:
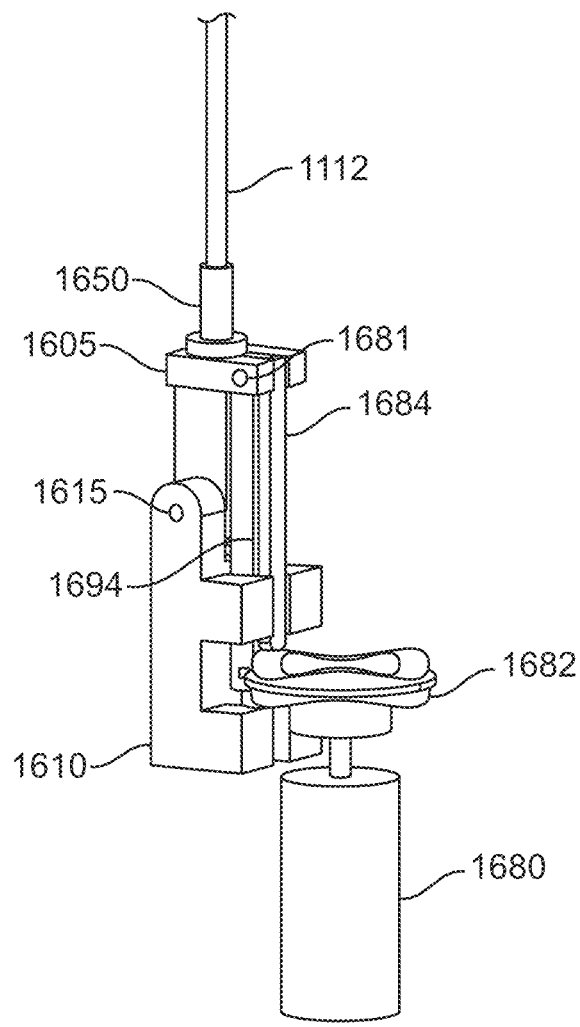
FIG. 21A illustrates an implementation of a cutter tube drive mechanism incorporating a motor-driven cam.
Figure 21B:
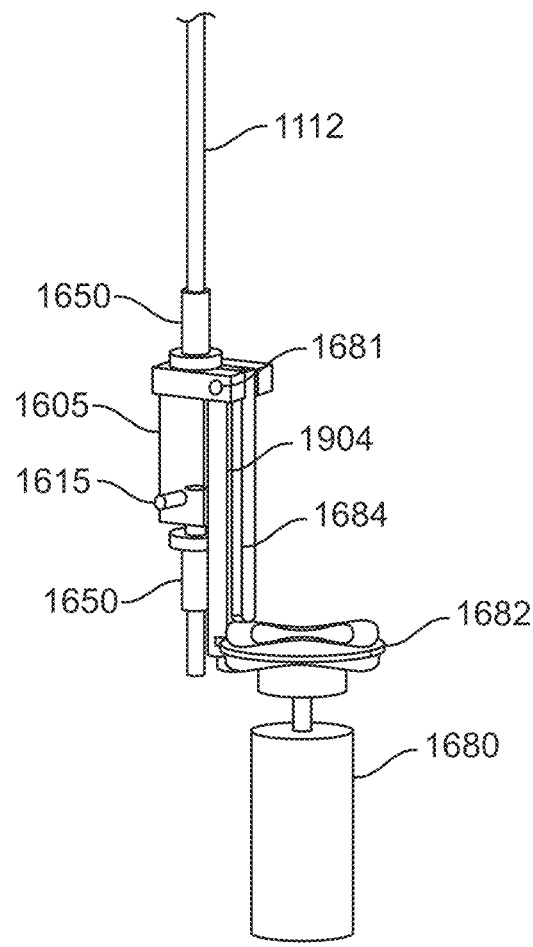
FIG. 21B is the cutter tube drive mechanism of FIG. 21A with the base hidden.

It should be appreciated that the drive mechanism 119 need not be a piezoelectric drive mechanism. FIGS. 21A-21D illustrate an implementation of a cutter tube drive mechanism incorporating a motor-driven cam that is capable of achieving a minimum tip speed. The drive mechanism 119 can include a base 1610, a motor 1680 configured to turn a cam 1682. The cam 1682 can incorporate a wave pattern on both ends. As the cam 1682 turns, the wave pattern of the cam 1682 drives a cam follower 1684 up and down. The cam follower 1684 is coupled to a rocker 1605 via a cam follower pin 1681. As the cam follower 1684 moves up and down it pivots a rocker 1605 about a rocker hinge pin 1615. As the rocker 1605 pivots back and forth, it can pivot the cutting tube 1112 back and forth. A support bushing 1650 can be incorporated that aids in distributing the forces on the tube 1112 and to help prevent the rocker 1605 from damaging the tube 1112. FIG. 21B is a side view of the drive mechanism 119 with the base 1610 hidden. The base 1610 can include a second support bushing 1650 that can contact the tube 1112 and provide a point of bending for the tube 1112 as it is driven back and forth.

Figure 21C:
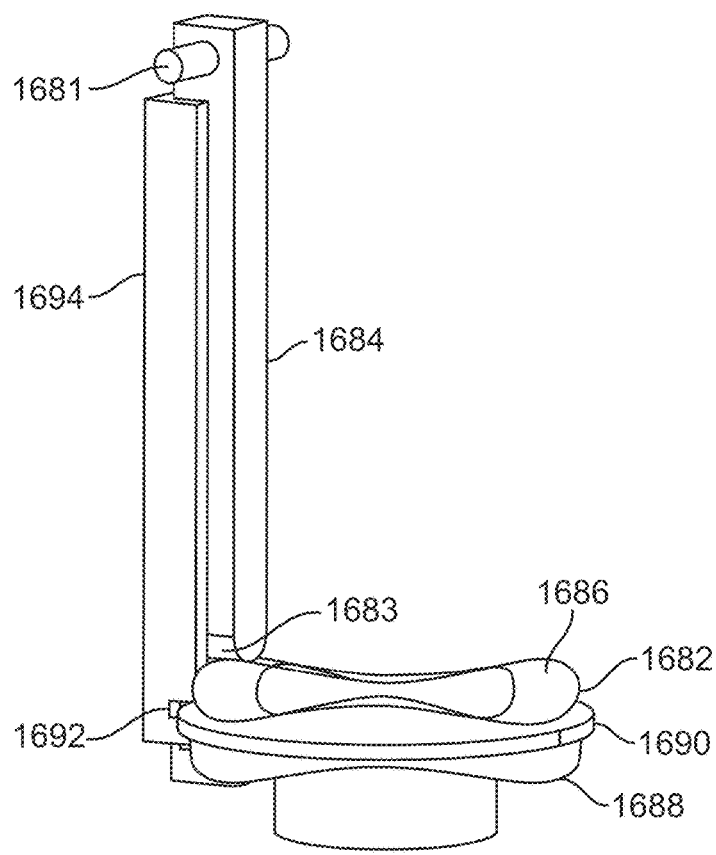
FIG. 21C is a close-up view of the cam mechanism of FIG. 21A.
Figure 21D:
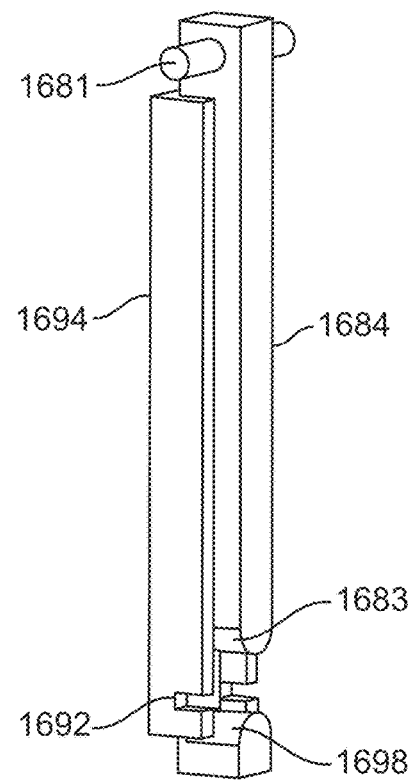
FIG. 21D is a view of the cam mechanism of FIG. 21C with the cam hidden.

FIG. 21C shows a close-up view of the cam mechanism. The upper cam surface 1686 of the cam 1682 can feature a radius so that the cam following surface 1683 of the cam follower 1684 can ride along the cam surfaces of the cam 1682 smoothly. The cam 1682 features an upper cam surface 1686 and a lower cam surface 1688. The shapes of the upper and lower cam surfaces 1686, 1688 can be inverses of each other such that the distance in the axial direction between the upper and lower cam surfaces 1686, 1688 is constant. The cam 1682 features a cam constraint rib 1690 that slides into the cam constraint slot 1692 on the cam constraint 1694. The cam constraint 1694 can be fixed to the base 1610 or can be integrated as one piece with the base 1610. The cam constraint slot 1692 can prevent the cam 1682 from moving axially as it turns and applies force to the cam follower 1684. FIG. 21D shows a close-up view of the cam mechanism with the cam 1682 hidden. The lower cam follower surface 1698 contacts the lower cam surface 1688 of the cam 1682 and drives the cam follower 1683 downwards. The lower cam follower surface 1698 can have the same radius as the upper cam follower surface 1683 to ensure smooth movement along the cam 1682.

Figure 25C:
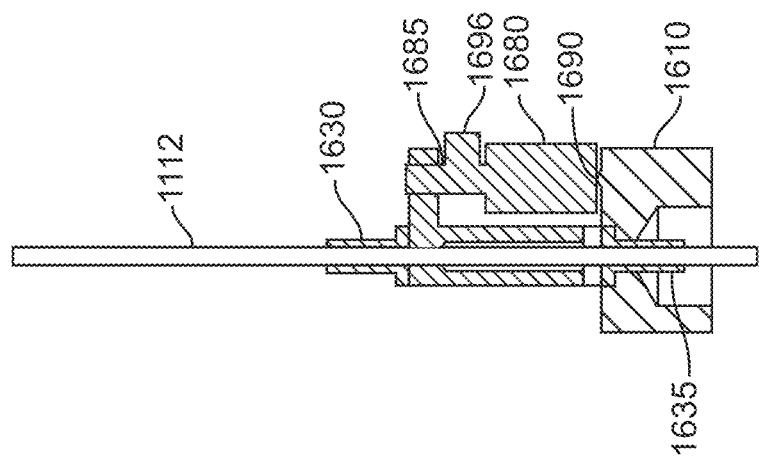
FIGS. 25A-25C illustrate an implementation of a cutter tube drive mechanism incorporating a vibrating motor.
Figure 25B:
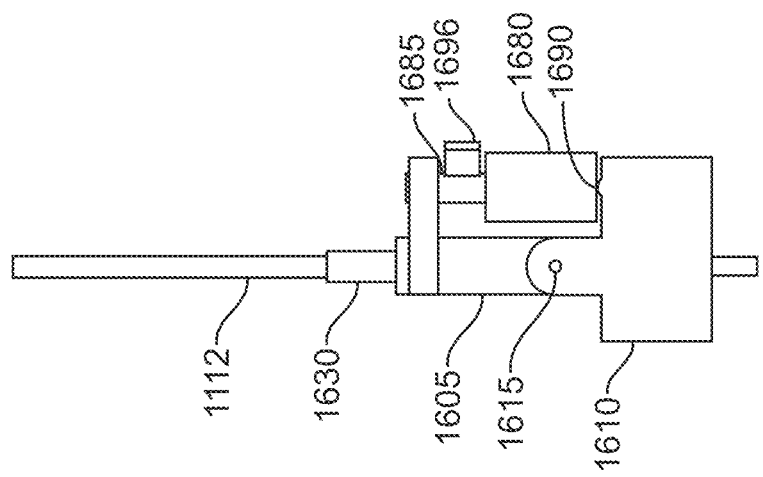
Figure 25A:
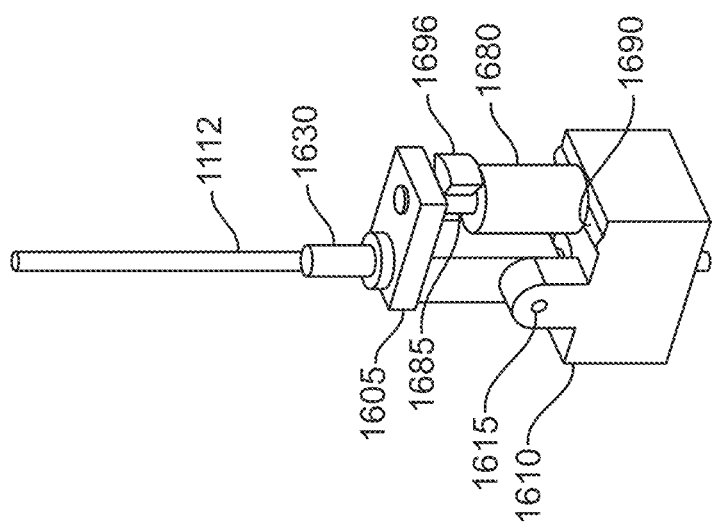
Figure 26A:
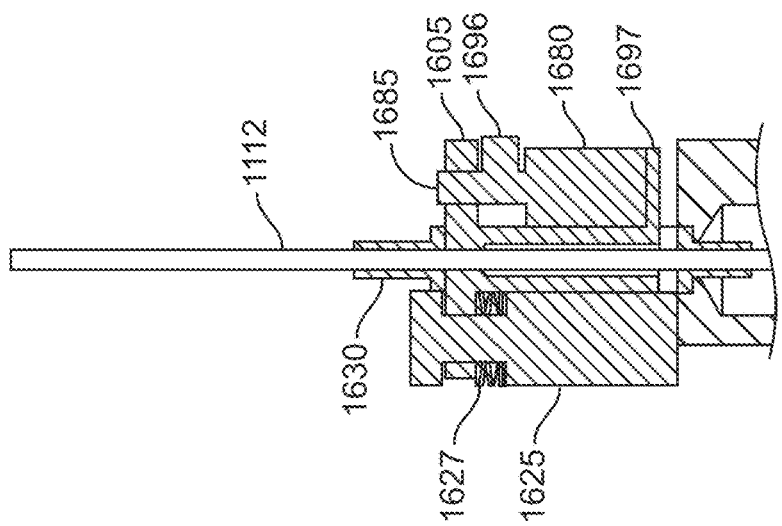
FIGS. 26A-26C illustrate another implementation of a cutter tube drive mechanism incorporating a vibrating motor.
Figure 26B:
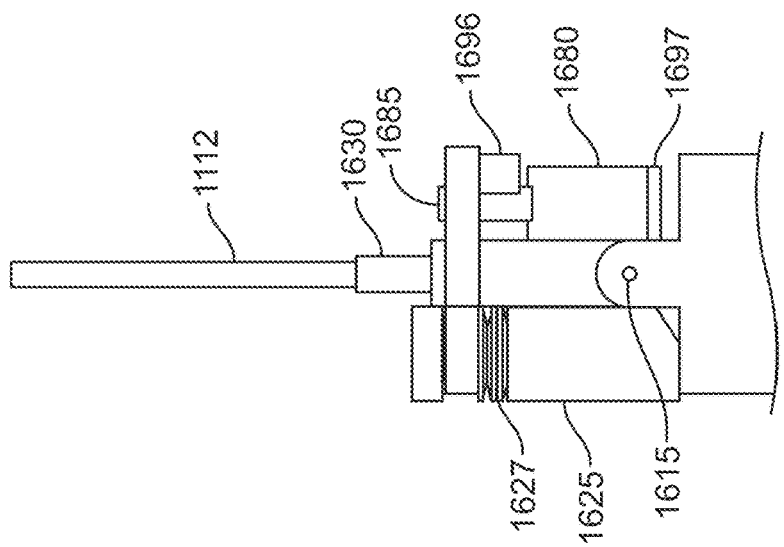
Figure 26C:
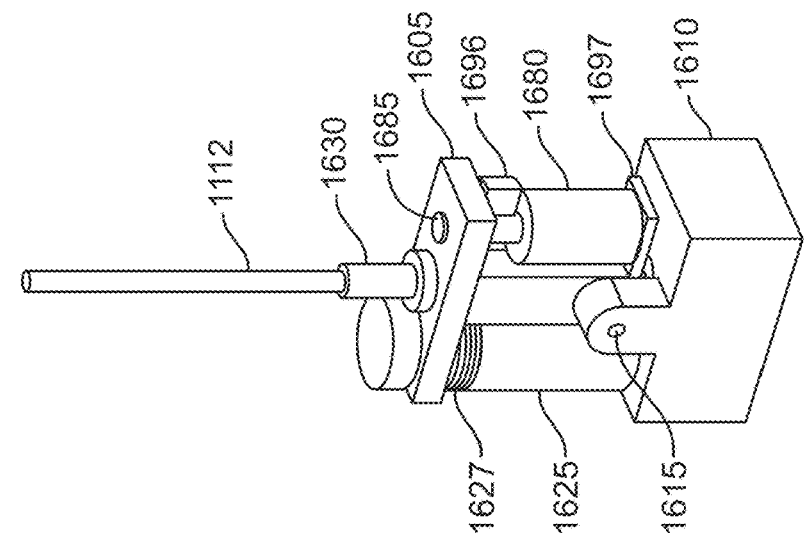

FIGS. 25A-25C and also FIGS. 26A-26C illustrate implementations of a cutter tube drive mechanism 119 incorporating a vibrating motor and a mechanical hinge incorporating a rocker 1605. The drive mechanism 119 can include a base 1610 configured to couple to a hand piece (not shown). The rocker 1605 can be attached to the base 1610 via a rocker pivot pin 1615 allowing the rocker 1605 to freely rotate relative to the base 1610. A motor 1680 can be coupled to the base 1610 such as on a top surface of the base 1610 at a coupling 1695. The coupling 1695 is configured to allow the motor 1680 to pivot side-to-side. In some implementations, the coupling 1695 can be a rounded ridge or other geometry. The coupling 1695 can be one of the other movable couplings described elsewhere herein. The cutting tube 1112 can extend through a bore in the rocker 1605 and through a bore in the base 1610. The motor shaft 1685 can extend through a bore in the rocker 1605. The motor shaft 1685 can be free to rotate relative to the rocker 1605. An eccentric or offset weight 1696 can be attached to the motor shaft 1685. As the motor shaft 1685 spins, the mass of the weight 1696 oscillating side-to-side causes the rocker 1605 to move or rock from side-to-side. In some implementation, the motor 1680 has a housing that is rigidly attached to the rocker 1605 and shakes the rocker 1605 and cutter tube 1112. In other implementations, the motor shaft 1685 is attached to a cam wobble plate that pushes on a cam follower that is rigidly connected to the rocker 1605 and cutter tube 1112. In another implementation, the motor housing is allowed to pivot such as via a rounded ridge, dome, or other geometry and the vibrating end is rigidly attached to the rocker 1605 and the cutter tube 1112. This can reduce the mass of the rocker 1605 and cutter tube 1112.

FIGS. 26A-26C illustrate another implementation of a cutter tube drive mechanism 119 incorporating a vibrating motor and incorporating a spring. In this implementation, the motor 1680 can be coupled on its lower end via welding, glue, or another mechanism to a motor support 1697. The motor support 1697 can extend from the bottom of the rocker 1605. The motor shaft 1685, which can extend through the rocker 1605 such that it can rotate freely, can be coupled to an offset weight 1696 configured to cause the rocker 1605 to rotate back and forth about the pivot pin 1615 as the motor shaft 1685 spins. This wags the tip of the tube 1112 back and forth. A spring post 1625 with a spring stack 1627 can be positioned on the opposite side of the pivot pin 1615 from the motor 1680. The rocker 1605 compresses the spring stack 1627 as it rotates counter-clockwise and the spring stack 1627 urges the rocker 1605 back in a clockwise direction.

Figure 27A:
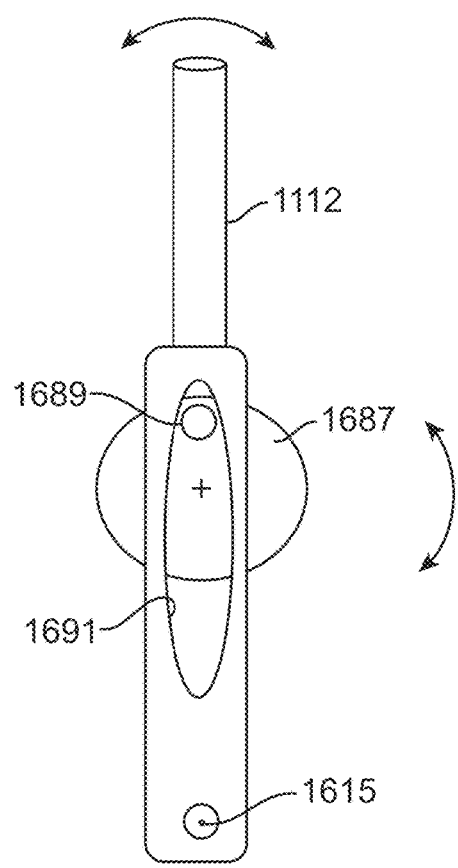
FIGS. 27A-27B illustrate other implementations of cutter tube drive mechanisms.

In an interrelated implementation, the cutter tube drive mechanism can include a motor-driven cam. The drive mechanism can incorporate a small motor that drives a wheel 1687 having a pin 1689 positioned near a perimeter of the wheel 1687 (see FIG. 27A). The pin 1689 can be positioned within a slot 1691 of a pivot arm 1693 that is attached to the cutter tube 1112 a distance away from the distal cutting tip. The cutter tube 1112 can be fixed longitudinally by a pivot pin 1615, but movable around the rotational axis of the pivot pin 1615. The rotational axis of the pivot pin 1615 is substantially parallel to a rotational axis of the wheel 1687. As the wheel 1687 rotates, the eccentrically positioned pin 1689 moves up and down within the slot 1691 of the pivot arm 1693. The pivot arm 1693, in turn, can oscillate about the rotation axis of the pivot pin 1615 causing corresponding wag of the distal cutting tip of the cutter tube 1112.

Figure 27B:
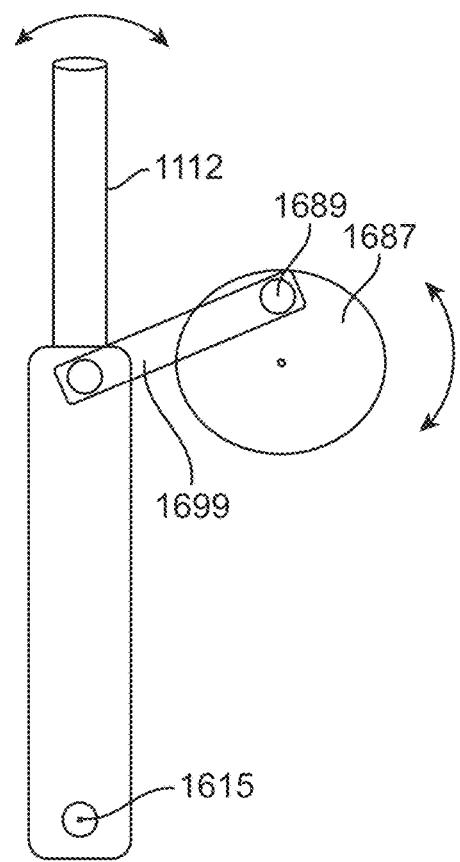

FIG. 27B illustrates an interrelated implementation of the cutter tube drive mechanism. The drive mechanism can again include a wheel 1687 driven by a small motor. The wheel 1687 can include an eccentrically positioned pin 1689 positioned near a perimeter of the wheel 1687. The pin 1689 can couple by a link arm 1699 to the pivot arm 1693 attached to the cutter tube 1112 a distance away from the distal cutting tip. The cutter tube 1112 can be fixed longitudinally by the pivot pin 1615, but movable around the rotational axis of the pivot pin 1615. As the wheel 1687 rotates, the pin 1689 causes the cutter tube 1112 to oscillate side-to-side around the rotational axis of the pivot pin 1615.

FIGS. 16A-16D, 18, 19A-19C, 20A-20B, 21B, and 25A-25C illustrate the lower (i.e., proximal) end of the cutting tube 1112 extending beyond the base 1610. A vacuum may be applied to the proximal end of the tube 1112 in order to evacuate material through the lumen of the tube 1112. Vacuum may be applied via an aspiration pump 1014 in the hand piece, which will be described in more detail below. It should be appreciated that the cutter tube drive mechanism can be incorporated within the disposable portion of the hand piece 1030.

The aspiration pump 1014 of the hand piece 1030, which can be integrated within, on or attached to the hand piece 1030, can draw the aspiration fluid and materials from the eye. As mentioned, the hand piece 1030 includes a hollow cutting tip or cutting tube 1112 that is configured to oscillate such as by a multi-stack of piezoelectric crystals 1120 or another cutter tube drive mechanism (i.e. voice coil, motor-driven cam mechanism, vibrating motor with eccentric weight) to break up the diseased lens. The fluid and materials from the eye enter a lumen 1110 through the cutting tube 1112. The inner lumen 1110 of the cutting tube 1112 is fluidly coupled to the waste line 1038. The aspirated material can be directed through the waste line 1038 towards the waste container 1044 by the aspiration pump 1014. An irrigation sleeve 1113 can be positioned over the cutting tube 1112 to provide irrigation fluid from the irrigation line 1034 through one or more irrigation openings 1111 (shown, e.g., in FIG. 9A) to the eye.

Figure 12:
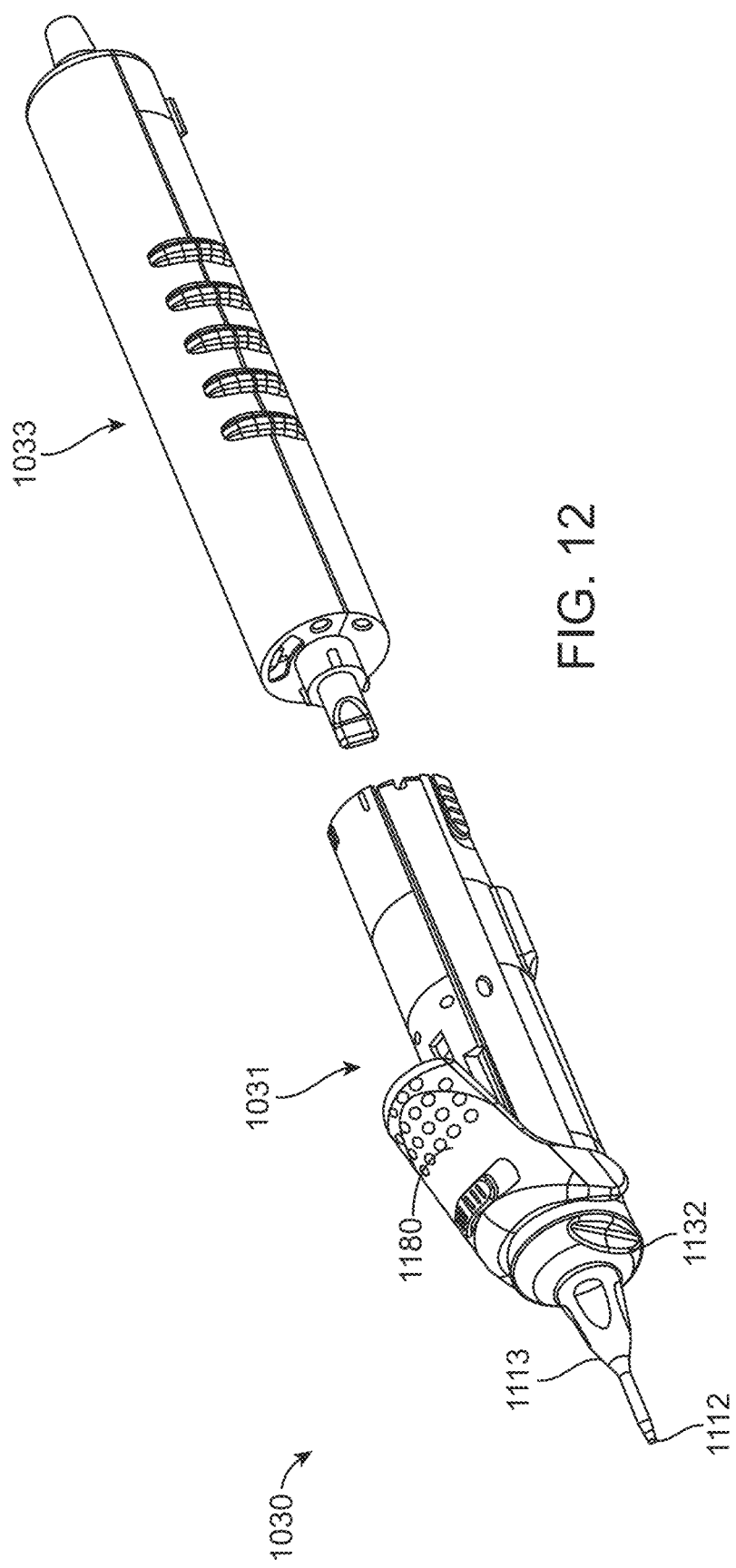
FIG. 12 shows a perspective view of the durable and disposable portions of an implementation of a hand piece separated from one another.

As best shown in FIG. 5B and also FIG. 12, the hand piece 1030 can include a disposable portion 1031 configured to be releasably coupled to a durable, reusable portion 1033. The disposable portion 1031 includes the components of the hand piece 1030 configured to come into direct contact with fluids and materials from the eye. The disposable portion 1031 of the hand piece 1030 can include the cutting tube 1112, irrigation sleeve 1113, the aspiration pump 1014, and connection sites for connecting the irrigation line 1034 and the waste line 1038 to the hand piece 1030. The irrigation line 1034 and waste line 1038 need not extend through the reusable proximal portion 1033. The reusable portion 1033 includes the components of the hand piece 1030 that are configured to remain outside the fluid path. The reusable portion 1033 may be sterilized and reused. The reusable portion 1033 can include the components configured to drive the aspiration pump 1014 and one or more of the components configured to drive the cutting tube 1112. For example, the pump motor 1115, the horn 1116, the piezoelectric crystals 1120 and the housing 1114 for containing the crystals 1120 can all be part of the reusable portion 1033. It should be appreciated that the reusable portion 1033 may also be disposable. For example, the drive mechanism for the cutting tube 1112 can be manufactured with lower cost materials such that it is financial feasible for portion 1033 to also be disposed of after a procedure. Lower cost materials such as polymer-based piezoelectric materials may allow for a significant reduction in cost.

The disposable portion 1031 may also include one or more components of the cutter tube drive mechanism 119. For example, the cutter tube drive mechanism including the rocker and pivot pin as well as the one or more components configured to rotate the rocker around the pivot pin can be positioned within the disposable portion 1031, including the piezoelectric stack(s) 1120 and associated couplings, clamps, and preload components. The cutter tube drive mechanisms shown in FIGS. 16A-16D, 17A-17C, 18, 19A-19C, 20A-20B, 21A-21D as well as 25A-25C and 26A-26C can all be incorporated within the disposable portion 1031 of the hand piece.

The coupling between the disposable portion 1031 and the reusable portion 1033 may be purely mechanical or may involve both mechanical and electronic couplings. For example, the disposable portion 1031 may have an electronic input configured to electronically couple with a portion of the reusable portion 1033. Alternatively, the disposable portion 1031 may have an input configured to mechanically couple and interact with the reusable portion 1033. The electronics configured to activate the cutter tube drive mechanisms can remain in the reusable portion 1033 of the hand piece such that upon coupling the disposable and reusable portions can be engaged with the cutter tube drive mechanism to activate the piezoelectric stack or motor, etc.

The disposable portion 1031 or the durable portion 1033 of the hand piece 1030 can include one or more inputs or actuators. The hand piece 1030 may also be actuated remotely. The instruments are sometimes referred to herein as a "device" or "tool" or "peripheral device" or "hand piece" or "hand held unit". Use of the term "hand piece" herein can include a hand piece coupled to a robotic arm or robotic system or other computer-assisted surgical system in which the user uses a computer console to manipulate the controls of the instrument. The computer can translate the user's movements and actuation of the controls to be then carried out on the patient by the robotic arm.

Each of these components as well as the coupling between the disposable and durable, reusable portions 1031, 1033 of the hand piece 1030 will be described in more detail below.

The systems described herein can include a single, reusable driver portion (sometimes referred to herein as a "durable portion") configured to operatively couple with one or more disposable working portions (sometimes referred to herein as a "disposable portion") in an interchangeable manner. The disposable working portions can be configured for different types of ophthalmic procedures including lens fragmentation, phacoemulsification, vitrectomy, bag polishing, aspiration, irrigation, coagulation, illumination, visualization, intraocular lens (IOL) insertion, and others. The operating parameters of the instrument can differ according to, for example, the configuration of the disposable working portion that is attached to the reusable driver portion.

The various features and functions of the devices described herein may be applied to one or more devices described herein even though they may not be expressly described in combination. It should also be appreciated that various features and functions of the devices described herein can be applied to conventional devices and systems known in the art also useful for cutting, fragmenting, emulsifying, or otherwise impacting tissues at or near a surgical site, including, but not limited to phacoemulsification systems, vitrectomy systems, bag polishing systems, and other tools useful in performing cataract surgeries or vitrectomy surgery, and the like.

Again with respect to FIGS. 5A-5B, the cutting tube 1112 can be a conventional phacoemulsification needle having a proximal end 1128 configured to couple with the horn 1116 extending through to a distal end region of the disposable portion 1031 upon coupling the disposable and durable portions 1031, 1033 of the hand piece 1030. The cutting tube 1112 is shown as being curved slightly away from a longitudinal axis of the hand piece 1030 and having a bevel tip. It should be appreciated the cutting tube 1112 can also be coaxial with the longitudinal axis such that extends substantially straight from the distal end of the hand piece 1030. Any of a variety of geometries and tip shapes are considered herein. At least a distal end region of the cutting tube 1112 and the irrigation sleeve 1113 are configured to be inserted into the eye in a minimally-invasive manner to cut, aspirate, and irrigate, such as during a cataract procedure.

As will be described in more detail below, the cutting tube 1112 is configured to oscillate (e.g., longitudinally, torsionally) in order to jackhammer or shear lens tissue and aspirate the emulsified lens tissue and fluid out of the eye. Cutting tube motion is described in more detail below. As used herein, "oscillate" or "oscillating movements" can include any periodic, repetitive movement that occurs according to a pattern and need not be sinusoidal. The oscillating movement can include reciprocating sliding movements that occur in a back and forth manner relative to the hand-held unit as described above. The oscillating movement can include repeatedly advancing and retracting the cutting tube along its longitudinal axis. The repeated advancing and retracting may occur along the longitudinal axis, but the path the oscillating movements take need not be linear. The path of movement can occur non-linearly (i.e. away from the longitudinal axis during at least a portion of the movement) along an elliptical pathway or a curvilinear pathway. The path of movement can be rotational, orbital, or torsional around the longitudinal axis of the device or other type of movement relative to the longitudinal axis of the device including three-dimensional movements in which the cutting tube moves back and forth as well as from side-to-side. The oscillating movements include profiles of repetitive patterns that may change depending on where in the cycle of oscillation the movement occurs. The oscillating movements can be asymmetric in profile, as will be described in more detail below.

The elongate component of the instrument being oscillated may be referred to herein as a "shaft" or "cutter" or "cutting tube" or "elongate member" and can be configured for different techniques, including phacoemulsification, vitrectomy, bag polishing, or other technique. At least a portion of the cutter can be tubular and having an internal lumen extending through it such that fluids can be delivered and/or aspirated through the internal lumen between a distal opening and a proximal opening from the lumen.

Any of a variety of configurations of the elongate cutting tube 1112 are considered herein. The cutting tube 1112 may have inner and outer members or the cutting tube 1112 can include only a single tubular element configured to oscillate relative to the hand piece 1030 to cut and aspirate material. Where the cutting tube 1112 is described as having an inner elongate member coaxially arranged within an outer tubular member the inner elongate member can be a solid rod and need not include an inner lumen. In some implementations, the cutting tube 1112 has a sharpened cutting tip or bevel, which can include a needle tip. The hand piece 1030 can include a cutting element having a sharpened needle tip and can be a solid element extending through an outer tubular member and aspiration forces applied through the lumen of the outer tubular member such that fluids and tissues are drawn into an annular gap extending between the inner and outer members. The cutting tube 1112 can have an inner lumen 1110 and distal edge configured to cut tissue. The distal edge can be sharpened while the opening into the tube can be cut at an angle to the elongate axis of the elongate member or perpendicular to the elongate axis of the elongate member. The inner lumen 1110 of the cutting tube 1112 can be configured to aspirate material therethrough, such as ocular lens material, lens fragments, vitreous, and/or fluids from the eye. Thus, aspiration forces can be applied through the inner lumen 1110 of the cutting tube 1112. However, aspiration forces can also be applied through a lumen of a tubular outer member extending over the cutting tube 1112 such that aspiration occurs through the annular space between the two. In such a configuration, the gap between the tubular outer member and the inner member can vary, for example, between about 0.001" to about 0.100". In some implementations, the aspiration forces can be applied through both the inner elongate member having a lumen and the lumen through the outer tubular member.

Figure 6:
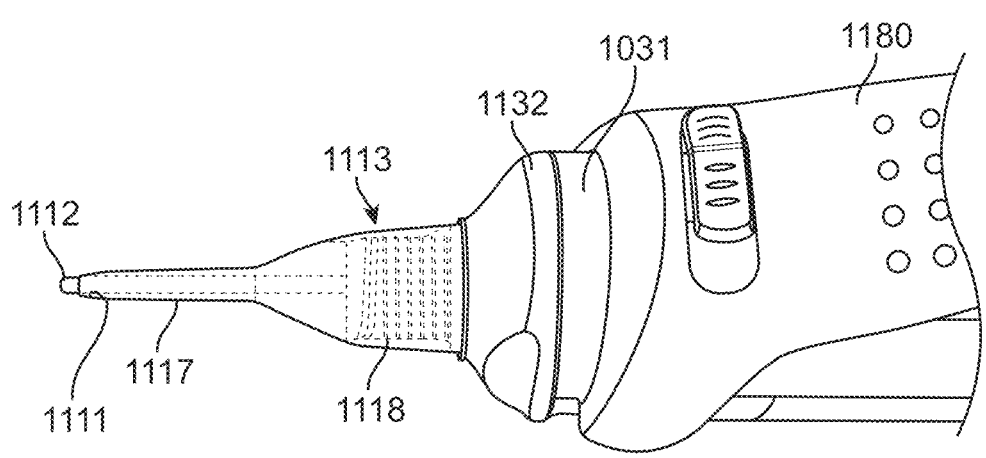
FIG. 6 shows a distal end region of the hand piece having an irrigation sleeve attached over a lens cutting tip.
Figure 9A:
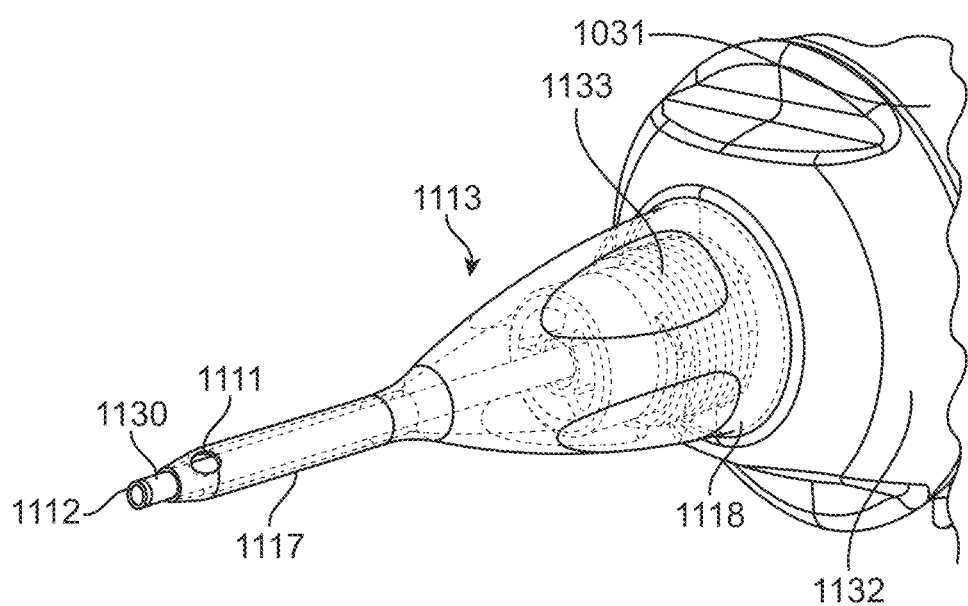
FIGS. 9A-9B shows the lens cutting tip of the hand piece of FIG. 7B having an irrigation reservoir.
Figure 9B:
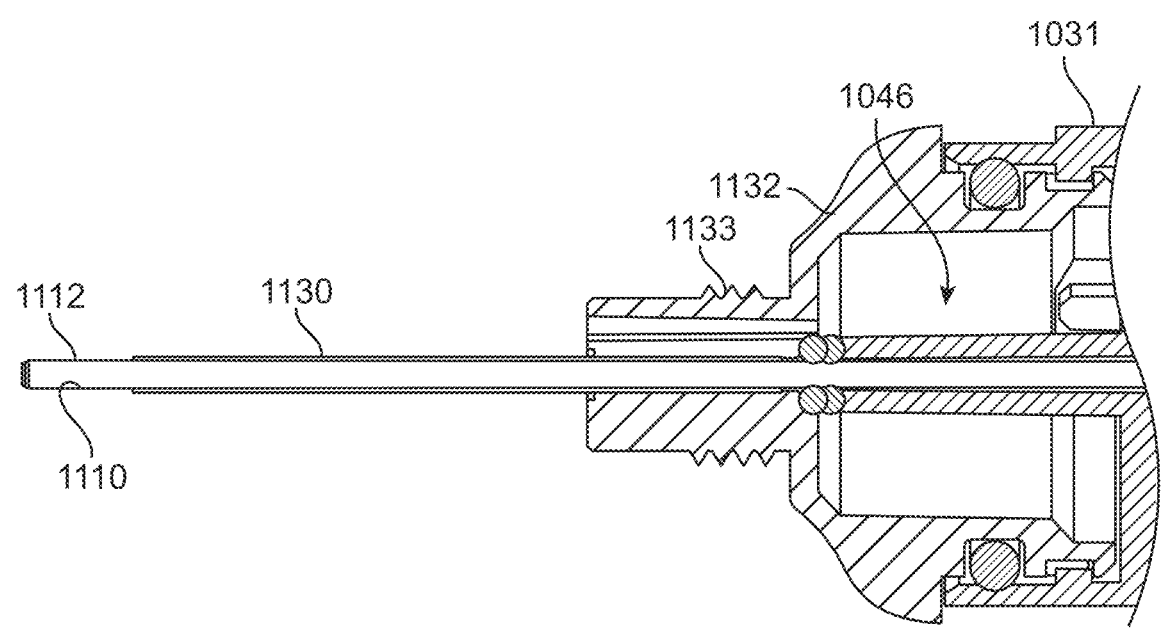

FIG. 6 and also FIG. 9A illustrate a distal end region of the disposable portion showing the cutting tube 1112 extending beyond a distal end of the irrigation sleeve 1113. The irrigation sleeve 1113 may include one or more openings 1111 near its distal end through which irrigation fluid may be delivered into the eye near the terminus of the cutting tube 1112. The irrigation sleeve 1113 can extend proximally over the cutting tube 1112 and couple with a distal end region of the disposable portion 1031. The distal end region of the disposable portion 1031 can include a nose cone or tip 1132 configured to receive the irrigation sleeve 1113. The tip 1132 and the irrigation sleeve 1113 can each be removably attached to the hand piece 1030. The irrigation sleeve 1113 can be a standard irrigation sleeve (e.g. irrigation tips by MST, Redmond, Wash.) having a substantially flexible, distal tubular portion 1117 and a less compliant, proximal coupling portion 1118. The tip 1132 can include external threads 1133 (see FIG. 9B) or other coupling features on a front end region configured to engage with corresponding threads or features on the proximal coupling portion 1118 of the irrigation sleeve 1113.

Figure 7A:
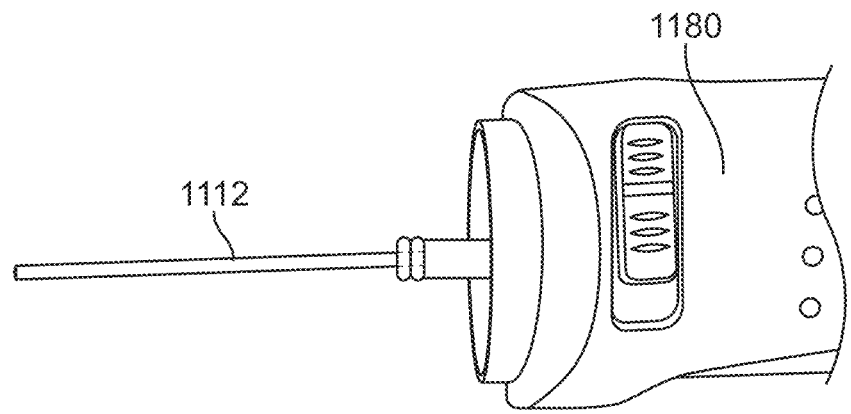
FIG. 7A shows the distal end region of the hand piece of FIG. 6 with the irrigation sleeve and tip removed.
Figure 7B:
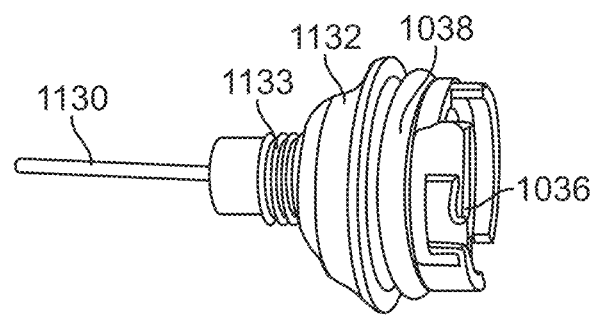
FIG. 7B shows the lens cutting tip of FIG. 6.
Figure 7C:
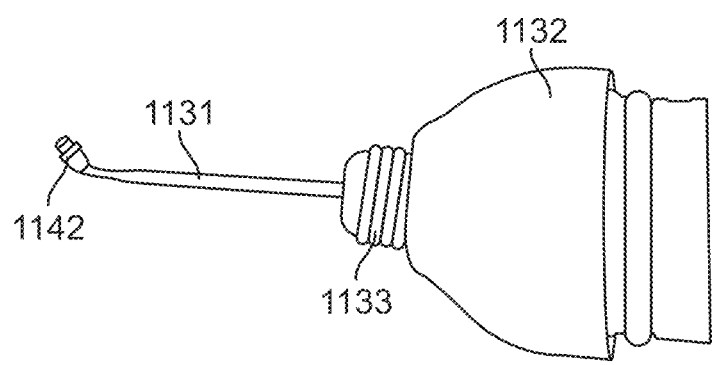
FIG. 7C shows a bag polishing tip having a bag polishing nub for use with the phacoemulsification hand piece of FIG. 7A.

The tip 1132 can be configured for any of a variety of techniques a user desires to perform with the hand piece 1030 during a procedure. Any of a variety of tips 1132 may be reversibly coupled to the distal end region of the disposable portion 1031 depending on the procedure in the eye a user desired to perform. The tips 1132 may be configured for phacoemulsification, bag polishing, vitrectomy, and other procedures. The tip 1132 can be reversibly coupled to the disposable portion 1031. FIG. 7A illustrates the distal end region of the disposable portion and the cutting tube 1112 without the tip 1132 being attached. FIG. 7B illustrates a first implementation of an exchangeable tip 1132 and FIG. 7C illustrates a second implementation of an exchangeable tip 1132. The proximal end region of the exchangeable tip 1132 can incorporate a reversible coupling feature 1136 and a sealing element 1138 such as an O-ring. The configuration of the coupling feature 1136 can vary including, but not limited to threads, snap lock, interference fit, bayonet, or other feature configured to allow the tip 1132 to affix to and seal with the disposable portion 1031.

The exchangeable tip 1132 shown in FIG. 7B includes a lens removal protective sleeve 1130 configured to be used during phacoemulsification. The lens removal protective sleeve 1130 can be fixedly coupled and extend from the distal end region of the tip 1132. The lens removal protective sleeve 1130 is sized and shaped to be positioned concentrically over the cutting tube 1112 along at least a portion of the proximal length of the tube 1112. The lens removal protective sleeve 1130 is configured to protect corneal tissues from damage where the cutting tube 1112 extends through the corneal incision during cutting tube 1112 motion when performing phacoemulsification. The lens removal protective sleeve 1130 may be formed of substantially flexible material such as silicone or substantially rigid materials such as a rigid plastic extrusion or metal hypotube. In some implementations, the lens removal protective sleeve 1130 can be a rigid tube having an inner diameter that is closely matched to an outer diameter of the cutting tube 1112 resulting in a low clearance between the two. The low clearance between the cutting tube 1112 and the lens removal protective sleeve 1130 means the lens removal protective sleeve 1130 maintains a small outer diameter such that the incision size through the cornea is minimized while still allowing for relative sliding between the inner and outer shafts. The cutting tube 1112 can have a maximum outer dimension of between 0.5 mm and 1.4 mm. The lens removal protective sleeve 1130 may be rigidly coupled to the tip 1132, exchangeable, or may be retractable. The length of the lens removal protective sleeve 1130 can vary, but is generally at least as long as necessary to cover the region of the cutting tube 1112 that extends through the incision. A user can cover the oscillating cutting tube 1112 and use a different sort of tip during a procedure, for example for capsular bag polishing and cortical tissue removal following lens extraction. Longer length of the lens removal protective sleeve 1130 can cover half the stroke length of the oscillating cutting tube 1112, thereby reducing exposed stroke length of the oscillating cutting tube 1112. The lens removal protective sleeve 1130 can be longitudinally positionable such that the effective stroke length of the oscillating cutting tube 1112 can be adjusted from zero to 100% of its uncovered stroke length. The lens removal protective sleeve 1130 can also be positioned so that the oscillating cutting tube 1112 remains recessed a certain depth within the lens removal protective sleeve 1130. This can prevent ocular tissue from coming into contact with the oscillating cutting tube 1112, and effectively resulting in a suction-only mode of operation. The lens removal protective sleeve 1130 when positioned to reduce the effective cutting tube stroke length can prevent tissues from 'lollipopping' on the end of the cutting tube 1112 by pushing stuck tissue off the cutting tube 1112 as the cutting tube 1112 tip retracts within the lens removal protective sleeve 1130.

Figure 8A:
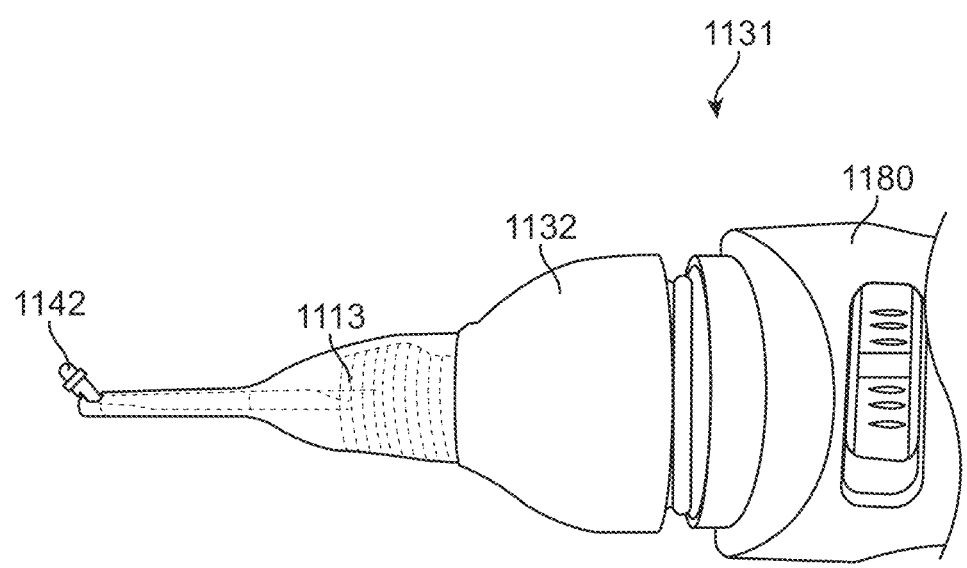
FIG. 8A shows a bag polishing tip attached to the hand piece of FIG. 6 and an irrigation sleeve attached over the bag polishing protective sleeve.
Figure 8B:
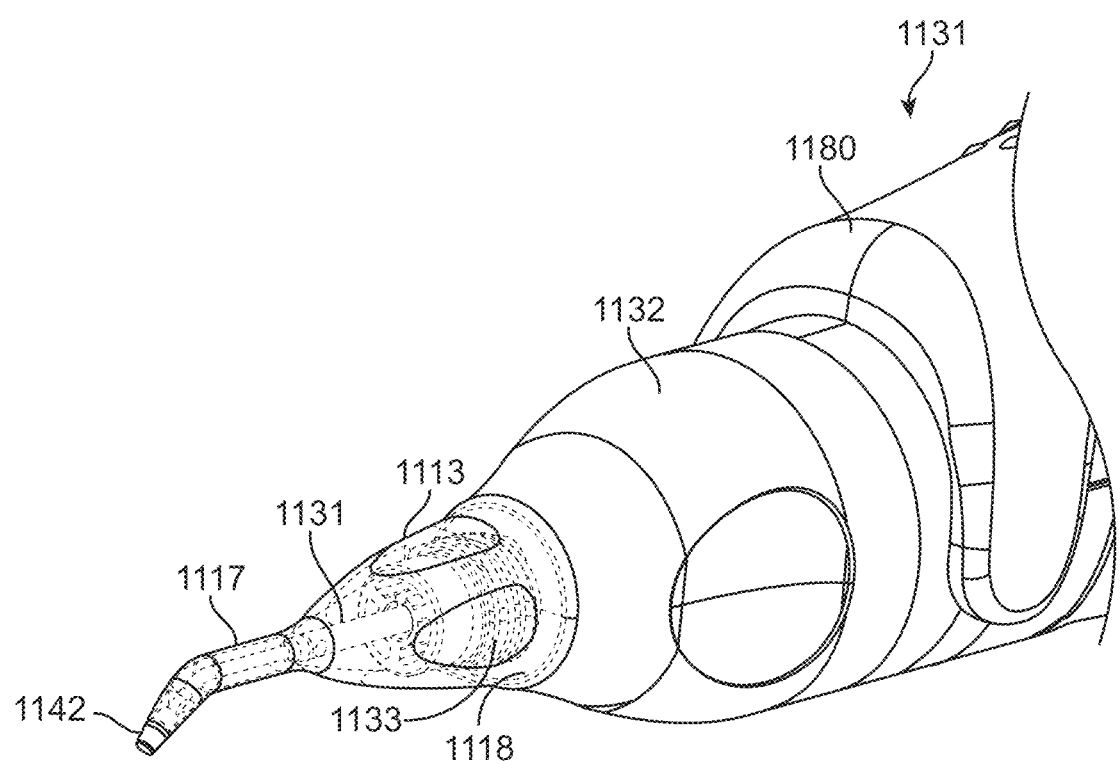
FIG. 8B shows a bag polishing tip attached to a hand piece and an irrigation sleeve attached over the bag polishing protective sleeve.
Figure 8C:
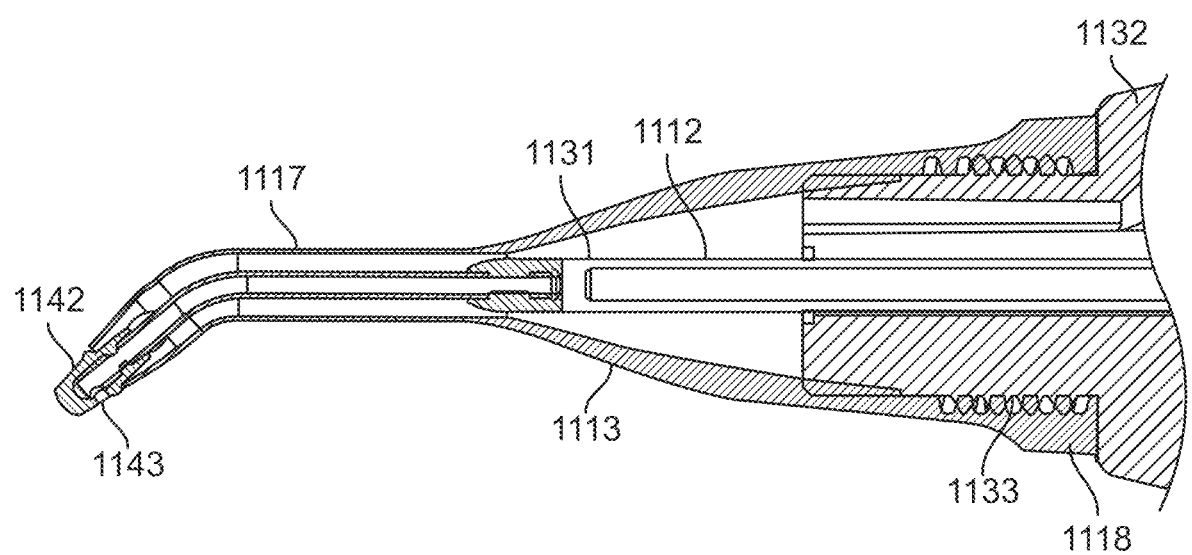
FIG. 8C is a cross-sectional view of the bag polishing tip of FIG. 8B.

The color of the exchangeable tip 1132 and/or the sleeve of the tip 1132 can provide information regarding the length of the sleeve and for what purpose it is useful. FIG. 7B shows a lens removal tip 1132 having a shorter lens removal protective sleeve 1130 configured for protecting the cornea during phacoemulsification. FIG. 7C shows a bag polishing tip 1132 having a longer bag polishing protective sleeve 1131 coupled to a bag polishing nub 1142 (see also FIGS. 8A-8C). The lens removal tip 1132 may be a first distinguishable color such as blue and the bag polishing tip 1132 may be a second distinguishable color such as white. Other markers, indicators, colors, are considered as well for easily distinguishing between the tips. The bag polishing protective sleeve 1131 of the bag polishing tip 1132 in FIG. 7C has a length sufficient to receive the cutting tube 1112 such that the distal end of the cutting tube 1112 is always contained within the bag polishing protective sleeve 1131 with the inner lumen of the bag polishing nub 1142 extending beyond the distal tip of the fully extended cutting tube 1112 thereby completely isolating cutting tube 1112 action from ocular structures. FIGS. 8A-8C illustrate the bag polishing tip 1132 positioned on the distal end region of the disposable portion 1131. The cutting tube 1112 is fully contained within the bag polishing protective sleeve 1131. The bag polishing nub 1142 is positioned beyond the distal tip of the irrigation sleeve 1113.

Surgeons commonly perform a bag polishing step following lens removal cataract. The bag polishing nub 1142 is gently slid along the surface of the capsular bag to release any adhered cortical material. The cortical material that is released is then aspirated through small holes in the bag polishing nub 1142. The nub 1142 may include a small hole 1143 through at least one side of its diameter (see FIG. 8C). The hole(s) 1143 may have any of a variety of sizes, shapes, and distributions along the wall depending on the overall number of holes 1143 incorporated. The hole 1143 may have a diameter in the range of about 0.002" to about 0.030", or preferably about 0.008" to about 0.012". In an implementation, the hole 1143 may face downward relative to the perspective of a user holding the hand piece 1030 or may face sideways or upwards relative to a user holding the hand piece 1030. In some implementations, the hole 1143 may be partially or fully on the distal face of the nub 1142. The distal face of the nub 1142 may be substantially rounded such as a semi-hemispherical shape or the distal face may be substantially flat. The flat face of the nub 1142 may be angled relative to the diametrical axis of the nub 1142. A relief hole may be positioned along at least a portion of the bag polishing tip 1132, such as the bag polishing protective sleeve 1131 or the nub 1142. The relief hole may be substantially smaller than the hole 1143, for example about 0.0001" to about 0.008", or more preferably between 0.001" to about 0.004". The relief hole may function as a bypass when the hole 1143 is occluded. The relief hole also allows vacuum to dissipate when the hole 1143 is occluded and the user releases a trigger 1180 on the hand piece 1030 when the hand piece 1030 is idle. Any accumulated vacuum may dissipate via the movement of fluid through the relief hole. The nub 1142 may include a surface texture for freeing the cortical tissue. The shape of the nub 1142 may be substantially atraumatic such that contact between the nub 1142 and the capsular bag does not risk puncturing the capsular bag during scrubbing motions.

It should be appreciated any of a variety of accessory tips can be coupled to the distal end of the disposable portion 1031. In some implementations, a vitrectomy style cutting sleeve having a side opening for cutting in a guillotine style fashion. The sleeve can be inserted over the cutting tube 1112 such that the cutting tube 1112 extends through and is coaxially arranged within an outer tube such that the cutting tube 1112 slides reciprocally within the outer tube. This style cutting element can be particularly useful for chopping and removing harder lens material. The outer tube can be a stationary tubular element coupled to a distal end region of the hand held portion 1030 and the cutting tube 1112 can be movable such that it can oscillate within the lumen of the outer tube. The distal tip of the cutting tube 1112 can be formed into a cutting edge, such as a short, sharpened bevel. In operation, tissue may enter into the outer tube through the side opening and be dissected by the cutting edge as the cutting tube 1112 is reciprocated within the outer tube. This vitrectomy style cutting tip can further include a removable or retractable outer sheath for sliding over the side openings, for example, during insertion of the shaft into the anterior chamber. During insertion, the cutting area of the shaft can remain covered within the outer protective sheath to prevent snagging on the incision or other eye tissues prior to cutting. After insertion, the sheath can be retracted or otherwise removed when the operator is ready to start cutting and/or aspirating. The retraction can be manually activated by a user or can be automatically retracted by the device upon actuation of cutting and/or aspiration. After cutting/aspiration is complete and the instrument is ready to be removed from the eye, the sheath can be advanced distally to once again cover the openings.

The exchangeable tips 1132 can be used with cutting tubes 1112 that are substantially straight, particularly where the sleeves of the tips 1132 are rigid. In some implementations where the cutting tube 1112 is curved away from the longitudinal axis or incorporates a feature angled relative to the longitudinal axis, the sleeve of the exchangeable tips 1132 may be flexible to allow for the sleeve to insert over the cutting tube 1112.

A single reusable driver portion 1033 can be configured to operatively couple with one or more disposable working portions 1031 in an interchangeable manner. The disposable working portions 1031 can be configured for different types of procedures including lens fragmentation, emulsification, vitrectomy, bag polishing, aspiration, irrigation, coagulation, illumination, visualization, IOL insertion, and others. The disposable working portions 1031 therefore may be used for any of a variety of procedures including vitrectomy, phacoemulsification, intraocular lens insertion, etc. The operating parameters of the instrument can differ according to, for example, the disposable working portion 1031 attached to the reusable driver portion 1033 and/or the particular procedure being performed, the different stages of the procedure, the surgeon's personal preferences, whether the procedure is being performed in the anterior or posterior portion of the patient's eye, and so on. The components of the working portion 1031 can vary depending on the type of procedure and each of the different working portions 1031 regardless the procedure it is configured to perform can operatively couple and be operated by a single reusable driver portion 1033. The different disposable working portions 1031 will be described in more detail below.

Again with respect to FIGS. 5A-5B, the irrigation fluid line 1034 can connect to the disposable portion 1031 of the hand piece 1030 via an irrigation port 1144. The location of the irrigation port 1144 can vary, but generally the irrigation port 1144 is arranged relative to the irrigation fluid line 1034 such that the irrigation fluid line 1034 is not integrated or embedded within or extending through a significant length of the hand piece 1030 as is the case with conventional hand pieces. In an implementation, the irrigation port 1144 can be located near a distal end region of the disposable portion 1031 near where the irrigation sleeve 1113 couples with the tip 1132. The irrigation port 1144 provides a substantially rigid connection to the otherwise flexible irrigation line 1034 such that fluid from the irrigation source 1032 may be delivered through the irrigation sleeve 1113 to the eye. The location of the aspiration port 1154 can also vary.

The irrigation source 1032 can couple to the irrigation sleeve 1113 via the irrigation fluid line 1034. The irrigation sleeve 1113 can extend over at least a portion of the protective sleeve 1130, 1131 as shown in FIG. 8C or 9A. The irrigation sleeve 1113 can be removed from the hand piece 1030, for example, as part of a removable tip 1132 or removed individually from the tip 1132 via threads or other coupling feature. FIG. 9A shows the irrigation sleeve 1113 threaded onto a forward end of the tip 1132 having external threads 1133 and extending over a proximal region of the cutting tube 1112.

In some implementations, the hand piece 1030 can incorporate an irrigation fluid reservoir 1046 in communication with the irrigation flow path between the irrigation port 1144 and the irrigation sleeve 1113. In an implementation, the irrigation fluid reservoir 1046 is located within the tip 1132 near the distal tip of the disposable portion 1031 of the hand piece 1030 allowing for virtually immediate replenishment of the aspirated fluid volume (see FIG. 9B). The reservoir 1046 can be configured to store an amount of fluid from the irrigation line 1034 near where the irrigation fluid is being delivered through the sleeve 1113. The reservoir 1046 can fill with irrigation fluid such that in the event of a cutting tube occlusion and the resulting increase in vacuum pressure, the sudden outrush or "surge" of fluid removed when the occlusion resolves, the irrigation fluid stored up in the reservoir 1046 can be available to very quickly replace the surge volume removed. The fluid from the reservoir 1046 can be pulled into the eye almost instantaneously upon the increase in negative pressure to maintain sufficient pressure within the eye to avoid collapse of the anterior chamber. The reservoir 1046 can be a compliant chamber such as balloon or elastic membrane, or incorporate another compliant element configured to urge fluid out of the reservoir 1046 when there is a decrease in anterior chamber pressure. In some implementations, the reservoir 1046 is contained on one end by a spring-loaded piston that may elastically move such that the volume of the fluid in the reservoir 1046 changes as the pressure within the eye changes. The piston may be connected mechanically to the pumping mechanisms of the device such that any pulses of suction are actively timed with inspiration of fluid into the eye.

The distal cutting tube 1112 including any protective sleeves, tips, or irrigation sleeves can have a maximum cross-sectional diameter that is suitable for minimally-invasive procedures in the eye to minimize the corneal incision size. In some implementations, the maximum cross-sectional diameter of the cutting tube 1112 is about 1.25 mm. The maximum cross-sectional diameter can be smaller than this or can be larger than this diameter, for example, no more than about 2 mm in diameter, no more than about 3 mm in diameter, up to about 4 mm in diameter, or up to about 5 mm in diameter. As described elsewhere herein, a distal opening from the cutting tube 1112 can have a smaller inner diameter in relation to the inner diameter of the remainder of the lumen 1110 extending through the cutting tube 1112 to mitigate problems with clogging. In some implementations, the difference between the nominal inner diameter of the cutting tube 1112 and the inner diameter of the distal opening can be between about 0.003" to about 0.006". In some implementations, the cutting tube 1112 can have a nominal inner diameter of about 0.0375" that narrows at the distal opening to about 0.033". The nominal inner diameter of the cutting tube 1112 can be between about 0.012" to about 0.036". Thus, eye tissue pieces that are smaller than the tip diameter can be aspirated through the lumen 1110 of the cutting tube 1112 and once inside the lumen 1110 are less likely to get stuck or cause a clog because the inner diameter of the remainder of the lumen 1110 is larger than the inner diameter of the distal opening.

Again with respect to FIGS. 5A-5B, the phacoemulsification hand piece 1030 can include an integrated aspiration pump 1014 within the disposable portion 1031 of the hand piece 1030. The aspiration pump 1014 can be located in, on, or otherwise near the hand piece 1030 thereby minimizing a length of the aspiration line 1038 between the vacuum source provided by the pump 1014 and the distal tip of the cutting tube 1112 within the eye 36. Incorporating a vacuum source within the hand piece 1030 (e.g. near the distal cutting tip) minimizes the volume of the aspiration flow path improving control and responsiveness while decreasing latency or hysteresis. Conventional phaco devices and other devices using a vacuum source remote from the hand-piece suffer from slow responsiveness and lower effective vacuum applied at the treatment site. Conventional systems have long, compliant suction lines connecting the vacuum source to the hand-piece. Compliance within a fluidic system can increase the time for suction to be transmitted from the suction source to the treatment site when the suction source is activated (and deactivated). Compliance within a fluidic system can also contribute to losses in vacuum transmitted to the treatment site resulting in the effective vacuum amount being different from the theoretical vacuum setting at the source. Additionally, the longer the fluidic lines between the vacuum source and the treatment site, the greater the friction losses, further reducing the vacuum available at the treatment site. For example, a remote vacuum source set at 600 mmHg may effectively transmit to the treatment site only 200 mmHg during some periods. The latency and hysteresis in conventional phaco devices having a remote vacuum source causes these designs to be susceptible to surges in fluid volume aspirated following a clog, particularly when the vacuum source is set at the higher flow rates. The actual surge volume in conventional systems is approximately equal to the degree of volumetric compliance in the suction line extending between the remote vacuum source and the hand-piece, which can be quite large (e.g. greater than 20 mL in some instances). This is a large surge volume to manage considering average patients have an anterior chamber volume of less than 0.3 mL. Users tend to set the vacuum source to lower levels to mitigate the increased surge volume risk associated with higher flow rates.

The hand pieces described herein can apply greater effective vacuum at the treatment site and more rapidly respond to pressure changes, and by avoiding the line losses associated with conventional systems. The hand pieces described herein have improved responsiveness and control even when used as higher vacuum settings. If an occlusion occurs due to a piece of lens blocking the distal opening, the vacuum will build (e.g. up to about 500 to 600 mmHg or more). When the blockage passes breaking the seal, the surge associated with the devices described herein is significantly improved as compared to conventional devices having remote vacuum sources. For example, the surge volume of the devices described herein can be as low as about 100 cubic mm, 200 cubic mm, or no more than about 300 cubic mm, whereas conventional phaco machines can have surge volumes that can be 10×, 20×, 50×, or 100× greater than this volume. The surge volume is smaller because the hand pieces described herein have a comparatively shorter aspiration flow path between vacuum source and target treatment site. The short aspiration flow path may also be substantially rigid or non-compliant, which further reduces the surge volume. For example, greater than 50%, 55%, 60%, 65%, 70%, 75%, 80%, 85%, 90% of the aspiration flow path of the devices described herein can be rigid resulting in no more than 10%, 15%, 20%, 25%, 30%, 35%, 40%, 45%, or 50% compliance in the aspiration flow path. The substantially non-compliant and short aspiration flow path of the devices described herein reduces the potential surge volume and also reduces the dead space that can contribute to the latency effect and lack of responsiveness.

The configuration of the pump 1014 within the hand piece 1030 can vary. Preferably, the aspiration pump 1014 has a small form factor such that it does not significantly impact the relative ergonomics of the hand piece 1030. The aspiration pump 1014 can be a piston pump, roller pump, peristaltic pump, linear peristaltic pump, scroll-type pump, venturi, rotary vane, gear, screw, diaphragm, centrifugal, or other pump. In an implementation, the aspiration pump 1014 of the hand piece 1030 is a roller or peristaltic pump (see FIGS. 5A-5C). In another implementation, the aspiration pump 1014 of the hand piece 1030 is a piston pump (see FIGS. 13A-13L). In another implementation, the aspiration pump 1014 of the hand piece 1040 is a linear peristaltic pump (see FIGS. 221-22D, 23A-23D, 24A-24B). The aspiration pump 1014 can be the piston pump described in U.S. Patent Publication No. 2018/0318133, published Nov. 8, 2018, which is incorporated by reference herein.

The pump 1014 can be configured to apply continuous, semi-continuous, and/or pulsatile aspiration. The hand piece 1030 can also include more than a single aspiration source where each source may be programmed to apply (simultaneously, if desired) different flow rates. For example, the hand piece 1030 may include a first aspiration pump internal to the hand piece 1030 configured to apply a continuous or semi-continuous flow rate (low-level or high-level aspiration) and a second aspiration pump internal to the hand piece configured to apply a pulsatile flow rate. The different flow rates and flow types can also be applied by a single pump that may be selectively activated to achieve the different aspiration types.

Figure 5C:
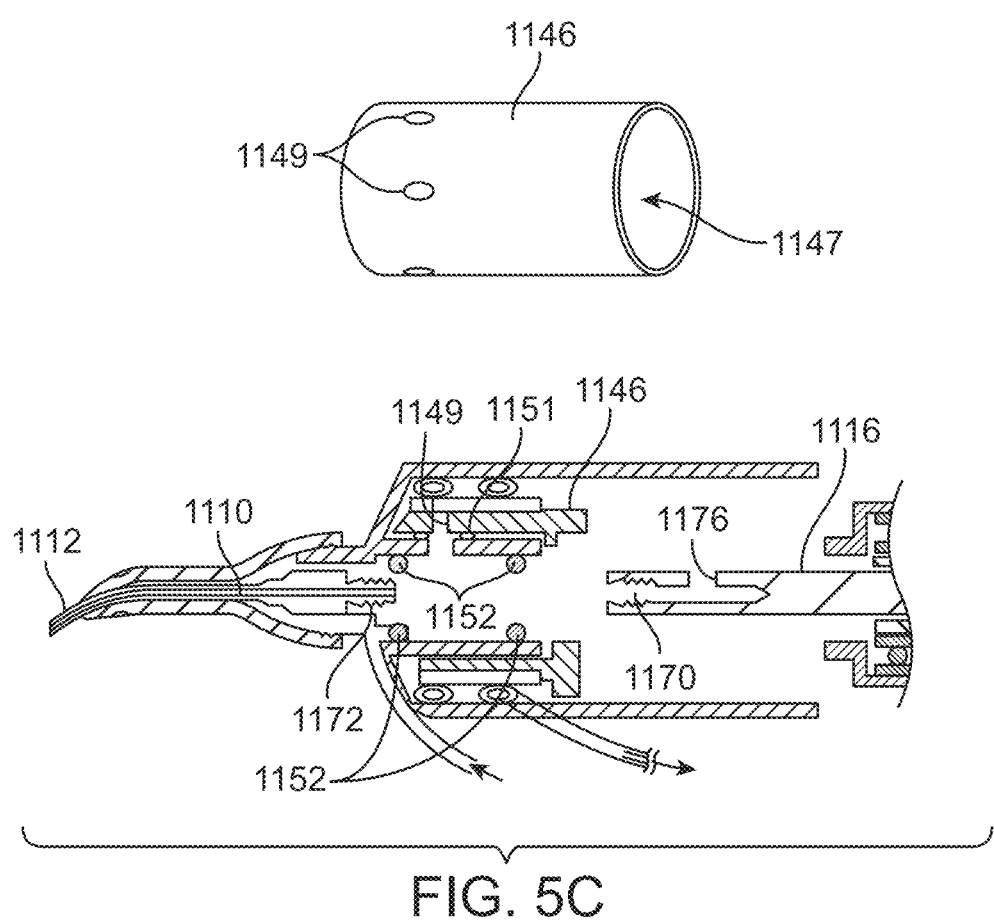
FIG. 5C shows the hand piece of FIG. 5B illustrating a pulsatile vacuum valve.

In an implementation and as shown in FIGS. 5A-5C, the aspiration pump 1014 of the hand piece 1030 is a roller pump or peristaltic pump contained within the housing 1145 near distal end of the disposable portion 1031 of the hand piece 1030 configured to draw fluid and materials into the distal tip of the cutting tube 1112 and direct it toward the waste line 1038. The aspiration pump 1014 can include a roller housing 1146, one or more peristaltic rollers 1148, and fluid tubing 1150 contained within a peristaltic housing wall, which can be formed by the inner surface of the housing 1145 of the disposable portion 1031. The fluid tubing 1150 can be wound in a helical or spiral configuration from near the distal end of the housing 1145 towards the proximal end of the housing 1145. The number of helices or complete turns the fluid tubing 1150 makes can vary, but may be at least 1, 2, 3, 4, or 5 turns. The fluid tubing 1150 can be in communication with the lumen 1110 of the cutting tube 1112 such as via a port (not shown) at a first end and in communication with the aspiration port 1154 at a second end. The waste line 1038 can connect to the disposable portion 1031 via an aspiration port 1154. Alternatively, the waste line 1038 does not need to connect to an aspiration port 1154 per se and can be a continuation of the same tubing line 1150 of the roller pump 1014. The one or more peristaltic rollers 1148 can be radially disposed cylindrical pins configured to compress the fluid tubing 1150 against the inner, peristaltic housing wall 1145. The number of rollers can vary including 1, 2, 3, 4, 5, or more rollers 1148. As the peristaltic rollers roll along the tubing 1150, fluid is urged towards the waste line 1038 as well as drawn into the lumen 1110 of the cutting tube 1112. The peristaltic rollers 1148 may be positioned between the co-axial roller housing 1146 and the fluid tubing 1150, and the fluid tubing 1150 may be positioned between the peristaltic rollers 1148 and the peristaltic housing wall 1145. The rollers 1148 may be rolled by the inner, coaxial cylindrical roller housing 1146 and thus, the aspiration pump 1014 functions like roller bearings with rolling pins. Alternatively, the relative locations of the tubing 1150 and pins 1148 and roller housing 1146 can be reversed such that the rollers exist at a larger radius than the tubing, squeezing the tubing to the inside. The roller housing 1146 can be a cylindrical element having a proximal end that is driven by the pump motor 1115 within the durable portion 1033 of the hand piece 1030, which will be described in more detail below. The roller housing 1146 can couple with the pump motor 1115 upon coupling the disposable portion 1031 with the durable portion 1033. Any of a variety of coupling features are considered herein. For example, the roller housing 1146 and the pump motor 1115 can couple together via a dog clutch or spline or other type of reversible coupling that connects two rotating components. The proximal end of the roller housing 1146 can include a set of regularly spaced recesses (or protrusions) that engage with a set of corresponding protrusions (or recesses) on the distal end of the motor 1115. Alternatively, the rollers 1148 and roller housing 1146 may be part of the reusable portion instead of the disposable portion thereby eliminating the need for the coupling mechanism that connects the two rotating components and reducing the disposable portion component cost.

The vacuum can be applied by the aspiration pump 1014 in the hand piece 1030 in disconnected pulses of negative pressure, for example, by actuation of one or more valves or due to movement of one or more pistons or by the pattern of the roller movement. As described elsewhere herein the cycling of the negative pressure pulses and positive pressure pulses can vary (e.g. between 1 Hz and about 10,000 Hz, or 100 Hz to about 5,000 Hz, or about 500 Hz to about 2000 Hz) and very small volumes (e.g. 10 uL up to about 1 mL). The cycling of negative pressure can be very fast (e.g. between about 5,000 Hz to about 10,000 Hz) or can be not as fast (e.g. 1 Hz up to about 1000 Hz).

Peristaltic pumps may provide negative pressure in a less pulsatile manner than, for example, piston pumps. Still, peristaltic pumps may create somewhat uneven, semi-continuous aspiration. As each roller 1148 contacts the tubing 1150 and starts to roll there may be a brief pause in vacuum generation. As the roller 1148 moves, the vacuum generation is relatively smooth until the next roller 1148 makes contact with the tubing 1150 and so on. Thus, pulsation with the peristaltic pump can be achieved depending on the number of rollers 1148 and the timing of roller 1148 contact with the tubing 1150. In contrast, piston pumps can create a sharp spike in vacuum as the piston retracts backwards. This sharp spike in vacuum can be leveraged to create pulsatile aspiration, for example, by incorporating a plurality of pistons retracting sequentially.

It should be appreciated that conventional phacoemulsification hand pieces (e.g., those utilizing piezoelectric resonant drive systems) can incorporate an aspiration pump within or on the hand piece as described above. The aspiration pump can be positioned near the distal end of the hand piece, for example, in front of the piezoelectric crystals. The aspiration pump can also be positioned near the proximal end of the hand piece, for example, behind the piezoelectric crystals. The pump can be integrated with the hand piece or coupled to a region of the hand piece in a snap-on or modular fashion to generate aspiration forces near the cutting tube and minimize the length of the compressible tubing. The aspiration pump on the conventional phacoemulsification hand piece can vary in configuration including peristaltic, linear peristaltic, scroll, piston, or other pump type as described elsewhere herein.

The pulsatile aspiration also can be achieved using valving in the hand piece 1030 to control exposure of the cutting tube 1112 to the vacuum pressure generated in the hand piece 1030. The valving can be incorporated to provide more pulsatile, discontinuous aspiration regardless of the type of pump 1014 and regardless whether the pump is incorporated in the hand piece 1030 or external to the hand piece 1030. For example, a conventional phacoemulsification system having a remote pump within the console may incorporate one or more valves near the cutting tube of the hand piece 1030 to control exposure of the cutting tube to the negative pressure generated. The one or more valves may be integrated within the hand piece positioned near a distal end (i.e. the location of the cutting tube) or near a proximal end of the hand piece.

The valves allow for a full vacuum to be applied through the cutting tube 1112 in short pulses. The one or more valves may be coupled to the hand piece 1030 and positioned along a portion of the aspiration path. The valve may be movable from a closed configuration that blocks the aspiration path towards a fully open position opening the aspiration path to the lumen of the cutting tube 1112. The valve may be positioned in any position between the closed and fully open positions. The valve may be a movable element configured to move relative to an aperture to open and close the aspiration path. For example, the valve may be moved to a first position that exposes a small portion of the aperture. The valve may be moved to a second position that exposes a larger portion of the aperture. The valve may be moved to a first position for a period of time until the vacuum pressure within the cutting tube 1112 reaches a certain percentage of a target maximum pressure (e.g. 75% or 570 mmHg of a target 760 mmHg). Once the target vacuum pressure is reached, the valve may be actuated to move to achieve a cycling of the suction pressure. The first phase may help in establishing the desired suction pressure that is then transitioned to a cyclic/periodic or modulated phase of vacuum. Motion of the valve may be achieved manually upon actuation by a user or may be achieved automatically upon initiation of the pump 1014 or cutting tube 1112 motion. It should be appreciated that the valving of the aspiration through the cutting tube 1112 can be used to control application of aspiration from the pump 1014 within the hand piece 1030 or to control application of aspiration from a pump remote from the hand piece 1030.

A small reservoir or vacuum accumulator may be incorporated within a region of the hand piece 1030. The accumulator may maintain the vacuum level achieved by the aspiration pump 1014 in the hand piece 1030 for a period of time. Momentary opening of the one or more valves within the hand piece 1030 may expose the vacuum reservoir to the lumen 1110 of the cutting tube 1112 enables the discontinuous, pulsatile application of suction. In some implementations, the valve is one as described in U.S. Publication No. 2018/0318132, filed May 3, 2018, and which is incorporated by reference herein. The configuration and arrangement of the valves can vary including poppet, ball, needle, leaf, pinch, or other rotationally sliding type of valve useful for controlling vacuum.

FIG. 5C illustrates an implementation of a valve within the hand piece 1030 configured to momentarily expose the lumen 1110 of the cutting tube 1112 to vacuum. The vacuum may be stored within an accumulator or any internal volume space available within the vacuum system. As discussed above, the roller housing 1146 may be a cylindrical element driven to rotate by the pump motor 1115. The roller housing 1146 may include an inner bore 1147 that is configured to be placed in fluid communication with the lumen 1110 of the cutting tube 1112 through one or more through-holes 1149 in the cylindrical wall of the roller housing 1146. When the through-hole 1149 in the roller housing 1146 aligns with an opening from the inner lumen 1110 of the cutting tube 1112 the lumen 1110 is exposed to vacuum created by the aspiration pump 1014. The more through-holes 1149 in the wall of the roller housing 1146, the greater the number of vacuum pulses per rotation of the housing 1146. Communication between the through-holes 1149 and the inner lumen 1110 may be sealed with one or more O-ring seals 1151.

Additionally, the cycles of negative pressure can be interspersed with short regurgitation via application of positive pressure between pulses of negative pressure. In some implementations, the cycles of negative pressure include short periods of vacuum interspersed by short periods of decreasing vacuum or no vacuum. In some implementations, the cycles of negative pressure include short periods of vacuum interspersed by short periods of positive pressure thereby resulting in a short regurgitation of fluid through the cutting tube, for example, between each roll of the peristaltic pin or during each cycle of piston movement.

Whether or not positive pressure is applied between the pulses of vacuum, the pulsatile vacuum creates pulses of discontinuous negative pressure through the cutting tube that can be between about 4 inHg up to about 30 inHg, preferably as close to full vacuum as possible with very little loss in pressure. In some implementations, the hand piece 1030 can create pulses of discontinuous negative pressure through the internal lumen of the cutting tube 1112 at a cycling frequency. The hand piece 1030 can also create pulses of discontinuous positive pressure having the same cycling frequency. Thus, the pulses of discontinuous negative pressure are interspersed by the pulses of discontinuous positive pressure. The cycling frequency of the pulses can be a relatively fast frequency, for example, at least about 0.5 Hz up to about 5000 Hz, or between 1 Hz and 4000 Hz, or between about 10 Hz up to about 2000 Hz. In some implementations, the cycling frequency of the pulses of discontinuous negative pressure is between about 1 Hz up to about 500 Hz. The pulses of discontinuous negative pressure aspirate a first amount of material into the internal lumen through the opening at the cycling frequency. The pulses of discontinuous positive pressure expel a second amount of material at the cycling frequency from the internal lumen through the opening. The volume of material being moved per cycle can vary, but is generally relatively small, for example, between about 0.1 mL up to about 1.0 mL, or approximately 0.5 mL. In some implementations, the nominal amount of fluid removed per pulse is about 100 microliters, or between 10 microliters up to about 1000 microliters. The second amount of material can be substantially less than the first amount of material within this general range of fluid amounts. The pulses of discontinuous negative pressure can be interspersed by discontinuous periods of lessening vacuum, no vacuum, or positive pressure at the same frequency.

In some implementations, the hand piece 1030 is limited from achieving maximum vacuum by incorporating a feature that automatically bypasses the cutting tube lumen 1110 depending on whether a threshold vacuum is reached. For example, a bleed valve, shunt, or other bypass mechanism can be incorporated to prevent a threshold amount of vacuum from being applied at a distal opening of the cutting tube 1112 and into the eye. A bypass to turn on or off the suction can limit the maximum amount of vacuum that can be generated within the eye even if the opening into the cutting tube 1112 is clogged. This bypass can prevent the vacuum from building in the event of cutting tube tip occlusion to decrease surge upon removal of that blockage. The bypass mechanism can be adjustable or selective such that a user can choose whether or not they want the potential for maximum vacuum or something less than maximum vacuum applied. An implementation of a vacuum bypass is described in more detail below with respect to FIG. 13L.

The disposable portion 1031 or the durable portion 1033 of the hand piece 1030 can include one or more inputs or actuators. The one or more inputs can vary including such as a trigger, button, slider, dial, keypad, switch, touchscreen, or other input that can be retracted, pressed, squeezed, slid, tapped, or otherwise actuated to activate, modify, or otherwise cause a response of the hand piece 1030. In an implementation, the hand piece 1030 includes a trigger 1180 positioned on a region of the disposable portion 1031 (see FIG. 6 and FIG. 12). The one or more user inputs can also be remote from the hand piece 1030 (e.g. on the system 1010 or on an external computing device in operative communication with the system 1010) or in a wired or wireless actuating device such as a foot pedal.

The hand piece 1030 can include separate inputs to activate each function of the device and/or the system 1010 in operative communication with the device (i.e. cutting, infusion, aspiration, including continuous or semi-continuous aspiration, pulsed vacuum, and/or pulsed vacuum with regurgitation between pulses, etc.). Alternatively, the input can be a multi-way button or trigger 1180 to activate more than a single function. For example, the hand piece 1030 can be configured for fluid delivery, fluid aspiration, and cutting. The trigger 1180 can activate irrigation-only function, continuous aspiration-only function, irrigation-plus-continuous aspiration function, or irrigation-plus-pulsed aspiration-plus-cutting function, etc. Generally, cutting without aspiration is not desired, however, a cutting-only function is considered herein as well. As an example and not to be limiting, a user can activate a first button or place the trigger 1180 in a first position to turn on the irrigation-only function or continuous aspiration-only function. After the first button is activated, the user can then activate a second button or place the trigger 1180 in a second position to turn on the irrigation-plus-continuous aspiration function. The user can then activate a third button or place the trigger 1180 in a third position to turn on the irrigation-plus-pulsed vacuum-plus-cutting function. The user can then commence cutting while vacuum continues. In some implementations, the second trigger activation is only possible after the first trigger activation occurs. The input can be a multi-way trigger 1180 as described above that has a first position configured to turn on both vacuum and oscillate the cutting tube (i.e. vacuum-plus-cutting function) and a second position configured to pause oscillation of the cutting tube while the vacuum through the cutting tube continues.

In some implementations, the hand piece 1030 can allow suction within the system to dissipate, for example, when a user desires to release an inadvertently captured capsular bag or when the device is idle. The venting mechanism can be coupled functionally to the trigger 1180 of the hand piece 1030, such as the multi-stage trigger 1180 shown in FIG. 12. When the trigger 1180 is idle, the venting mechanism can actively vent the device and when the trigger 1180 is activated to aspirate, the venting mechanism can be shut off. In some implementations, the trigger 1180 in its first, idle configuration can be biased upwards such that upon release of manual pressure on the trigger aspiration shuts off. Downward motion of the trigger 1180 can trigger aspiration (as well as irrigation and/or oscillation as described elsewhere herein). When the trigger 1180 is in the idle configuration and biased upwards, the system vents. When the trigger is urged downwards to activate aspiration, venting is turned off.

In some implementations, the drive mechanism can be a piezoelectric drive mechanism or motor-driven cam mechanism or vibrating motor with eccentric weight as described elsewhere herein capable of achieving side-to-side motion or "wag" of the cutting tube 1112 via a rocker, clamp, or other configurations (see, for example, FIGS. 16A-21D, and 25A-25C, 26A-26C) to translate the retraction and expansion of the piezoelectric along a first axis into motion of the cutting tube 1112 along a different axis that is generally orthogonal to the first axis. These cutter tube drive mechanisms can be positioned within the disposable portion as well.

As mentioned above and again with respect to FIGS. 5A-5C, the reusable, durable portion 1033 of the hand piece 1030 may include the pump motor 1115 with or without a gearbox and a drive mechanism. The drive mechanism can include the horn 1116, the piezoelectric crystals 1120 contained within the housing 1114, and a power cord 1160 configured to connect to the control unit 1012 of a phacoemulsification system 1010 to provide ultrasonic power for the piezoelectric drive system as well as DC power for the pump motor 1115. The piezoelectric crystals 1120 can be arranged coaxial to the longitudinal axis of the cutting tube 1112 for longitudinal motion and/or perpendicular to the longitudinal axis of the cutting tube 1112 for torsional motion.

Where the disposable portion 1031 is configured to come into contact with eye material, the durable portion 1033 is configured to remain outside of the eye and to not come into contact with material extracted from the eye. The cutting tube 1112 of the disposable portion 1031 may couple to the horn 1116 of the durable portion 1033, which in turn is driven by the piezoelectric crystals 1120. It should be appreciated that the durable portion 1033 may include any of a variety of drive mechanisms besides piezoelectric, such as magnetostrictive, electric, electromagnetic, hydraulic, pneumatic, mechanic, voice coil, or other type of drive mechanism. It should also be appreciated that the cutter tube drive mechanism can be within the disposable portion 1031 or with the durable portion 1033. Each of these components will be described in more detail below.

The motor 1115 for the aspiration pump 1014 can be a brushless DC motor or any type of motor or driver suitable for rotating a shaft. In an implementation, the pump motor 1115 can be an electric motor including a stator 1162 and a rotor 1164. The rotor 1164 can be a cylindrical shaped rotor configured to rotate due to interaction with the stator 1162. The movable rotor 1164 can couple to the co-axial roller housing 1146 as described above via a dog clutch or other type of coupling. The connection between the aspiration pump 1014 and the pump motor 1115 may incorporate gear reduction via gearbox or other mechanism. In an implementation, the durable portion 1033 incorporates a Harmonic-Drive gear reduction configured to achieve at least a 30:1 reduction. The speed of the motor 1115 can be controlled by a potentiometer linked to the trigger 1180 or a non-contact sensor configured to sense motion of the trigger 1180.

In an implementation, the durable portion 1033 can include a potentiometer ribbon extending between a distal end region of the durable portion 3210 and configured to activate the potentiometer. For example, the proximal end of the potentiometer ribbon can include a cut-out or other feature configured to engage with the potentiometer such that movement of the ribbon impacts the activation of the potentiometer. The trigger 1180 can be linked to a button rod that is movable along a longitudinal axis of the device as the trigger 1180 is actuated into one of a plurality of position. For example, when the trigger 1180 is moved from a first actuated position, the trigger can move the button rod a distance proximal such that a proximal end of the button rod extends a first distance into the proximal durable portion of the hand piece. The extension of the button rod into the durable portion can impact the speed of the motor by interacting with the distal end of the potentiometer ribbon extending with in the durable portion. Movement of the potentiometer ribbon in turn can activate the potentiometer engaged with the cut-out of the ribbon. The potentiometer can, in turn, change the speed of motor rotation. In some implementations, a non-contact sensor such as a Hall Effect sensor may be used to sense the distance the button rod has moved as a result of the trigger being depressed.

Still with respect to FIGS. 5A-5C, the motor 1115 can including a motor housing 1168 that is fixedly coupled to a forward end of the housing 1114 containing the multi-stack of piezoelectric crystals 1120. The crystals 1120 may be held within the housing 1114 by a back cylinder 1122 and bolt 1124. In other implementations, the piezoelectric stack can be part of the disposable portion as discussed above.

In conventional phacoemulsification, the piezoelectric crystal stack is driven at a very high frequency (e.g. 40,000 cycles/second) to achieve about 0.004" amplitude (about 100 μm) at the distal cutting tip. The piezoelectric crystals in conventional phacoemulsification are driven at their resonant frequency of the system and thus, only sinusoidal, symmetric motion at the cutting tip can be achieved. The conventional piezoelectric stacks and resonant mass rely on harmonics for cutting tip motion and thus, asymmetric motion is not possible without increasing significantly the energy and/or causing significant vibration.

In the case of the hand piece 1030 described herein, the oscillating system mass may be reduced to the greatest degree possible allowing the cutting tube 1112 to be driven directly (with or without amplifying components such as a rocker or other feature) by the piezoelectric stack 1120 in a non-resonant manner at a frequency that is less than ultrasonic (below 20 kHz). Despite being driven in a non-resonant manner, the cutting tube 1112 can have some additional "whipping" motion that results in greater overall displacement of the cutting tube 1112 than would otherwise be predicted.

Direct piezoelectric drive allows for obtaining asymmetrical motion of the cutting tube 1112, if desired, such that the retraction speed can be slower than the advancement speed. This allows for a fast advancement speed sufficient to achieve cutting, but a retraction speed kept below a cavitation threshold. In some implementations, this may include increasing the frequency of the piezoelectric crystal stack

1120. As discussed above the length of the horn 1116 is typically designed such that the distal end of the horn 1116 is at least 1 half wavelength away from the end of the piezoelectric crystal stack 1120. There are multiple ways to potentially reduce this length and thereby decrease the length and size of the horn 1116. The equation for wavelength $\lambda = c/f$, where $\lambda$ is the wavelength, c is the wave speed, and f is the frequency. In some implementations, the frequency can be increased in order to decrease the wavelength and therefore the required length of the horn 1116. As described elsewhere in this application, certain implementations reduce the retraction speed of the cutting tube 1112 such that cavitation may be avoided. Using such devices and methods provides an opportunity to increase the frequency of the cutting tube 1112 such that the horn 1116 may be smaller without adversely increasing the amount of cavitation. In still other implementations, the stroke distance of the cutting tip 1112 can be reduced while the frequency of oscillation is increased. Therefore the retraction speed of the cutting tube 1112 remains below a critical cavitation inducing level. By increasing the frequency as described above, the horn 1116 may be smaller.

Cataracts are typically classified based on severity on a scale of 1 to 5. The hand piece 1030 incorporating a piezoelectric stack 1120 configured for non-resonant, direct drive of the cutting tube 1112 may be particularly useful for cataracts in a range of 1 to 3. Users may choose to switch to conventional resonant phacoemulsification for harder cataracts above 3 to about 4. The systems described herein may be configured to switch between ultrasound and non-ultrasound modes. Switching between modes can be achieved by switching hand pieces entirely. For example, the console may be configured to couple with a conventional phacoemulsification hand piece as well as a non-ultrasound, direct drive hand piece. In another implementation, the same hand piece may be driven at different frequencies. For example, the drive mechanism may include a voice coil type drive mechanism that can be programmed to drive the cutter tube at ultrasound frequencies or at non-ultrasound frequencies in order to achieve asymmetric cutter tube motion.

The displacement or travel distance of the cutting tube 1112 of the hand piece 1030 described herein can vary. The longitudinal amplitude or displacement of the tip of the cutting tube 1112 can be equal to or greater than conventional phacoemulsification needles (i.e. 100 um or 0.004"). The longitudinal amplitude can be achieved via direct drive and at a lower frequency than conventional phacoemulsification (e.g. about 10,000 cycles/second). In an implementation, the displacement achieved by the cutting tube 1112 can be between about 0.005 mm-1.0 mm at a frequency of oscillation of the distal tip that is about 0.5 Hz-10,000 Hz, 0.5 Hz to 5000 Hz, or more preferably between 2000 Hz and 5000 Hz, or between 2,500 Hz and 4,000 Hz, or between 3,000 Hz and 3,600 Hz. In some implementations, the frequency is about 3,200 Hz. In this way, the devices described herein would not be ultrasonic and therefore would avoid generating the heat and cavitation associated with harmful effects in the eye during cataract surgery. In some implementations, the cutting tube 1112 of the hand piece 1030 can have a greater amplitude or displacement distance while being moved at a lower frequency than conventional phaco needles. In some implementations, the cutting tube 1112 is moved 0.012" to about 0.019". The amplitude can be between 0.005 mm to about 1.0 mm, or more preferably between 0.05 mm to about 0.1 mm. The frequency of oscillation can be less than 30,000 Hz, less than 25,000 Hz, less than 20,000 Hz, less than 15,000 Hz, less than 10,000 Hz and down to about 0.5 Hz, or down to about 1 Hz, or down to about 2 Hz, or down to about 5 Hz, or down to about 10 Hz, or down to about 25 Hz, or down to about 50 Hz, or down to about 100 Hz, or down to about 250 Hz, or down to about 500 Hz. The frequency of oscillation can be between about 0.5 Hz to about 30,000 Hz, or between 1 Hz to about 5000 Hz, or between about 2 Hz to about 2000 Hz.

As mentioned elsewhere herein, pulsatile vacuum may be applied through the cutting tube 1112 using the aspiration pump 1014 in the hand piece 1030. The relative coordination of the pulses of vacuum and oscillating motion of the cutting tube 1112 can vary. A pulse of vacuum may be applied during at least a portion of the extension of the cutting tube 1112. A pulse of vacuum may be applied during at least a portion of the retraction of the cutting tube 1112. A pulse of vacuum may be applied during at least a portion of both extension and retraction of the cutting tube 1112. In some implementations, the pulse of vacuum may begin before and be maintained during extension of the cutting tube 1112. The pulse of vacuum may begin after extension of the cutting tube 1112 begins. A single pulse of vacuum may be applied during multiple extensions and retractions. For example, the vacuum may be applied continuously through the cutting tube 1112 during at least about 1 oscillation, at least about 2 oscillations, at least about 5 oscillations, at least about 10 oscillations, at least about 20 oscillations, at least about 30 oscillations, at least about 40 oscillations, at least about 50 oscillations, up to about 100 oscillations of the cutting tube 1112. As an example, the cutting tube 1112 may oscillate 50 times during a single vacuum pulse that lasts 25 ms such that the frequency of oscillation of the cutting tube 1112 is about 2000 Hz.

The piezoelectric crystal stack 1120 in the hand piece 1030 can be longer than in conventional resonant drive phacoemulsification (e.g., about 2" in length) in order to achieve the amplitudes found in conventional, resonant phacoemulsification systems.

Again with respect to FIGS. 5A-5C, the horn 1116 can extend from a distal end of the piezoelectric stack 1120. The piezoelectric crystals 1120 move the horn 1116, which in turn moves the cutting tube 1112. Upon coupling the disposable and reusable portions 1031 and 1033 of the hand piece 1030, the horn 1116 can insert centrally through the aspiration pump 1014 in the disposable portion 1031. The roller housing 1146, the peristaltic rollers 1148, and the tubing 1150 thereby can radially surround the horn 1116. The distal end of the horn 1116 can extend through the inner bore 1147 of the roller housing 1146 and distally beyond the pump 1014 and is available near the distal end region of the disposable portion 1031 of the hand piece 1030 for coupling with the cutting tube 1112. As best shown in FIG. 5C showing the disposable portion 1031 removed from the reusable portion 1033, the horn 1116 can include an inner threaded recess 1170 configured to receive and engage with outer threads 1172 on a proximal end of the cutting tube 1112. The proximal opening from the lumen 1110 of the cutting tube 1112 can communicate with the inner recess 1170 of the horn 1116. The inner recess 1170 of the horn 1116 can include an opening or port 1176 configured to communicate with the helical tubing 1150 of the pump 1014. This port 1176 allows for fluid and other material aspirated into the lumen 1110 of the cutting tube 1112 to enter the pump 1014 and be urged toward the waste line 1038. Vacuum is applied to the inner lumen 1110 of the cutting tube 1112 upon alignment of the through-holes 1149 in the roller housing and the opening 1176 in the horn 1116. As the roller housing 1146 rotates the through-holes 1149 and the opening 1176 in the horn 1116 go in and out of alignment with one another. This cycling effectively turns on and off aspiration through the cutting tube 1112.

The horn 1116 can be formed of any suitable material or combination of materials for the purposes described herein. The material used for the horn 1116 affects the speed of sound in the horn material and therefore the length of the horn 1116 required such that the tip is located at least one half wavelength away from the piezoelectric crystals 1120. The horn 1116 may be formed of aluminum, stainless steel, titanium, or other commonly used materials. For example, the speed of sound in titanium is on the order of 6,070 m/s. In some embodiments, other materials may be considered for the horn material that have lower speeds of sound. For example, copper has a speed of sound on the order of 3,900 m/s and lead has a speed of sound on the order of 1,300 m/s. The slower the speed of sound, the smaller the horn 1116 may be needed such that the end of the horn is at a maximum amplitude node.

In some implementations, the hand piece 1030 can incorporate a drive mechanism configured to directly drive the cutting tube 1112 forward and backward or oscillating the cutting tube 1112 side-to-side as described elsewhere herein, rather than relying on resonance. The piezoelectric stack 1120 can respond to changes in voltage by decreasing or increasing in size. A voltage profile powering the piezoelectric stack 1120 can generate a motion profile of the cutting tube 1112 to produce the desired cutting tube movement. In some implementations, the voltage waveform sent to the piezoelectric stack 1120 can be generally non-sinusoidal in shape and therefore the cutting tube 1112 moves in a generally non-sinusoidal pattern as described elsewhere herein. The voltage may have a waveform that contracts the piezoelectric stack 1120 slower than it allows it to expand. This moves the cutting tube 1112 slower on the retraction stroke than on the extension stroke. Any number of motion profiles may be commanded based on the voltage waveform supplied to the piezoelectric stack 1120. For example, two or more overlapping voltage sinusoidal waveforms can be supplied to the piezoelectric stack 1120 that creates an interference effect such that a non-sinusoidal wave form is created. These drive mechanisms can be incorporated within the disposable or the reusable portions of the hand piece 1030. In a preferred implementation, the drive mechanism incorporates a piezoelectric stack 1120 that is contained within the disposable portion of the hand piece 1030.

In still further implementations, a combination of mechanisms and modalities are incorporated in the device to drive the cutting tube 1112 with a non-sinusoidal motion profile. For example, an electromagnetic coil can be configured to move a ferritic or magnetic core forward with the application of a current through the coil. The core can be configured to be driven forward by the electromagnetic coil, but then retract backwards (i.e. proximally) through the force of a compressed spring. Therefore, with an increase in current through the coil, the core is driven forward. With the current is reduced, the core retracts backward. In this manner, the core may be connected to cutting tube 1112 so that the extension forward can be executed quickly by the sudden increase in voltage in the coil, but the retraction may be slower by the force of the compressed spring.

The cutting tube 1112 can be driven so as to have an asymmetrical or sinusoidal motion profile. For example, some drive mechanisms providing a torsional cutting tube motion (see, e.g., FIGS. 16A-16D, 17A-17C, 18, 19A-19C, 20A-20B, 21A-21D, 25A-25C, 26A-26C, 27A-27B) need not provide asymmetrical motion profiles.

The hand piece 1030 can be capable of multiple functions (i.e. irrigation, aspiration, and cutting functions) all while maintaining full portability, flexibility, and freedom of movement. The functions of the hand piece 1030 can be initiated using an input (trigger 1180) on the hand piece 1030 capable of being actuated with a single finger or thumb. Because the hand piece 1030 requires no foot pedal, a user can stand more comfortably and naturally (e.g. on two feet or shifting their weight from foot to foot however they please) to perform a procedure. As described above, the hand piece 1030 may be actuated using the one or more inputs or triggers 1180 on the hand piece 1030 and/or remote from the hand piece 1030 such as on the control unit of the system 1010. The one or more inputs can be urged by a user into a position that causes the drive mechanism to ramp up one or more of the actions. For example, the trigger 1180 on the hand piece 1030 (or a foot pedal) can connect to the control unit that in turn interprets the signal and supply an appropriate drive waveform to the piezoelectric crystal stack 1120.

Use of the term "hand piece" herein can include a hand piece that is coupled to a robotic arm or robotic system or other computer-assisted surgical system in which the user uses a computer console to manipulate the controls of the instrument. The computer can translate the user's movements and actuation of the controls to be then carried out on the patient by the robotic arm. Thus, where the term "hand" or "hand piece" is used herein it should be appreciated that the hand may be a surgeon's own hand or a robotic "hand" manipulating the hand piece.

Coupling Between Disposable/Durable Portions

As mentioned above, the hand piece 1030 can include the disposable portion 1031 that is configured to releasably couple to the durable portion 1033. The disposable portion 1031 generally includes components configured to be exposed to human fluids and materials whereas the durable portion 1033 is intended to be reused with a new disposable portion 1031 coupled to it. The disposable and durable portions 1031, 1033 of the hand piece 1030 can couple together using a variety of mechanisms such as threads, snap-lock, bayonet lock, and the like.

In some implementations, the proximal end region of the housing 1145 of the disposable portion 1031 can define a chamber having a proximal opening through which at least a portion of the durable portion 1033 may be inserted and coupled to the disposable portion 1031 such as via bayonet lock mechanism (see FIGS. 5A-5C). For example, the horn 1116 and the motor 1115 within the motor housing 1168 may be inserted through the proximal opening of the housing 1145 of the disposable portion 1031 such that the motor housing 1168 is received within the chamber of the housing 1145. The two portions 1031, 1033 may then be in locked engagement with one another such as via a bayonet lock mechanism by turning a certain number of degrees once the horn 1116 and motor housing 1168 are received within the chamber. The connection between the disposable and durable portions 1031, 1033 can be purely mechanical or both mechanical and electrical connection. It should be appreciated that the motor 1115 may also remain outside the chamber of the disposable portion such that only the horn 1116 or another portion of the durable portion 1033 is inserted within the disposable portion chamber. The durable portion 1033 may insert into the disposable portion until a forward end of the rotor 1164 engages with the proximal end of the roller housing 1146 of the aspiration pump 1014. The two portions can be turned relative to one another (e.g. clockwise or counterclockwise) to fix the engagement and lock the two portions together. The coupling mechanism can include a release button configured to uncouple the two housing portions. In some implementations, the coupling can incorporate one or more markings on the respective housings to guide a user's alignment of the respective portions for insertion prior to locking. The locking mechanism between the portions can be mechanical such as a spring-loaded pin that must be retracted prior to detaching. The coupling between the disposable and durable portions creates a smooth continuous housing for the hand piece 1030.

The coupling between the disposable and durable portions 1031, 1033 of the hand piece 1030 can incorporate one or more sealing elements to ensure the hand piece 1030 does not leak during use. For example, the one or more sealing elements may be O-ring type seals 1152 positioned to prevent leaks where the horn 1116 of the durable portion inserts within the disposable portion. For example, a first O-ring 1152 can be positioned distal to the opening from the recess 1170 in the horn 1116 and a second O-ring 1152 can be positioned around the horn 1116 on a proximal end of the recess opening (see FIGS. 5A-5C). Additionally, a compliant seal can be positioned around a proximal end region of the horn 1116 near where it extends outside the piezoelectric stack housing 1114. In another implementation, the cutting tip 1112 can include one or more seals within the disposable portion 1031. In this configuration, no fluid from the surgical site comes into contact with the disposable internally. This has the benefit of eliminating the potential for cross-contamination that exists with conventional phaco hand pieces.

As discussed above, some implementations of the cutter tube drive mechanism 119 can be part of the disposable portion 1031 of the hand piece (e.g., FIGS. 16A-16D) whereas other implementations of the cutter tube drive mechanism 119 can be part of the reusable durable portion 1033 of the hand piece 1030 (see FIGS. 5A-5C). It should be appreciated that any of a variety of configurations are considered herein and the location of one or more components of the hand piece 1030 whether in the disposable or reusable portions can vary.

Other Pump Configurations

Figure 22B:
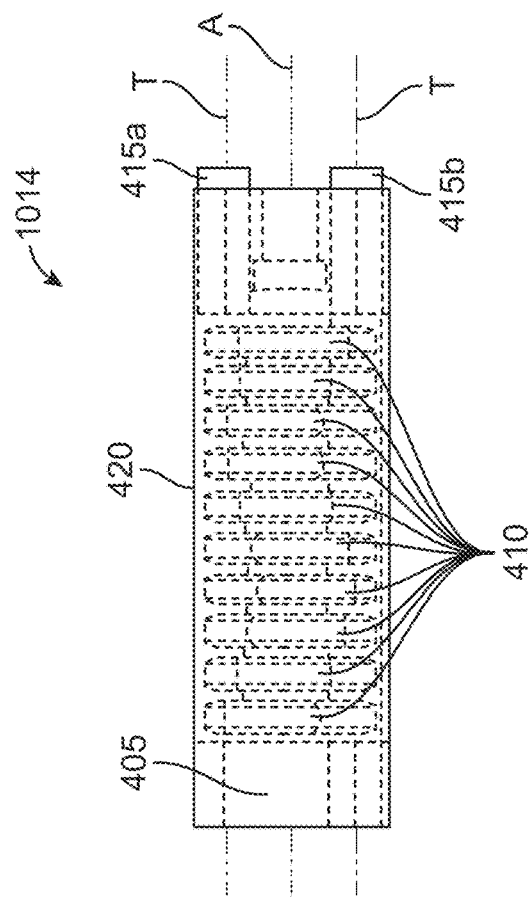
FIG. 22B shows a top view of the aspiration pump of FIG. 22A.
Figure 22A:
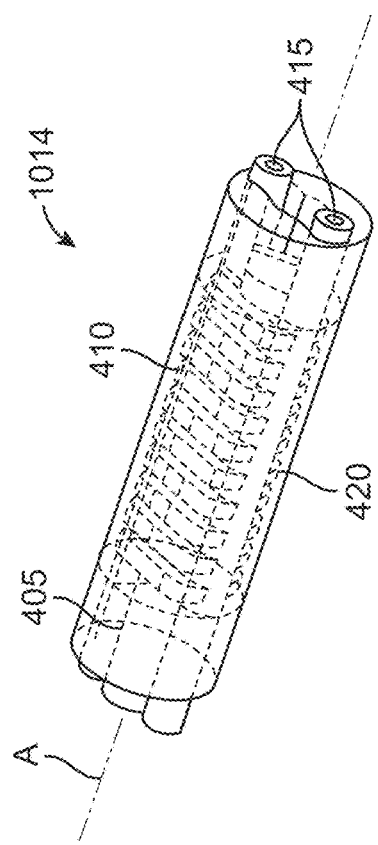
FIG. 22A shows a perspective view of an implementation of an aspiration pump configured to be integrated within a working portion of a microsurgical instrument.

As mentioned above, the aspiration pump 1014 within the hand piece can be any of a variety of low profile aspiration pumps including a peristaltic pump, linear peristaltic, piston pump, scroll-type pump, and the like. FIG. 5A-5C illustrate an implementation of a hand piece 1030 having an aspiration pump 1014 that is a peristaltic pump. FIGS. 22A-22B illustrate an implementation of a hand piece having an aspiration pump 1014 that is a linear peristaltic pump. FIGS. 13A-13L illustrate various views of an implementation of a hand piece 1030 of a phacoemulsification system having an aspiration pump 1014 that is a piston pump. The aspiration pump can include one or more pistons 2799 movable within respective pumping chambers 2705 of a piston manifold 2798. The pistons 2799 are powered by a drive mechanism such as a motor (not shown) that may be located within the durable portion 1033 of the hand piece 1030. FIGS. 13F-13H shows a vacuum manifold 2774 coupled to the piston manifold 2798 such that a vacuum chamber 2703 of the vacuum manifold 2774 is in fluid communication with the one or more pumping chambers 2705 in the piston manifold 2798. The one or more pistons 2799 powered by the motor generate a vacuum within the pumping chambers 2705 as well as the vacuum chamber 2703 for aspiration of material through the lumen 1110 of the cutting tube 1112.

It should be appreciated that any number of pistons 2799 can be positioned within respective pumping chambers 2705. Multiple pistons 2799 bouncing back and forth within their pumping chambers 2705 may create a pulsatile vacuum or full vacuum delivered to a distal portion of the lumen of the cutting tube 1112 in pulses of negative pressure. The pulsatile vacuum allows for application of full vacuum through the cutting tube 1112 without risk for collapse of the anterior chamber. While at the peak of the pulse, the system can generate a high vacuum. However, since it is pulsed, the average aspiration flow rate can be low enough for the irrigation inflow to maintain proper anterior chamber support even under these high vacuums at the pulse peak.

Figure 14A:
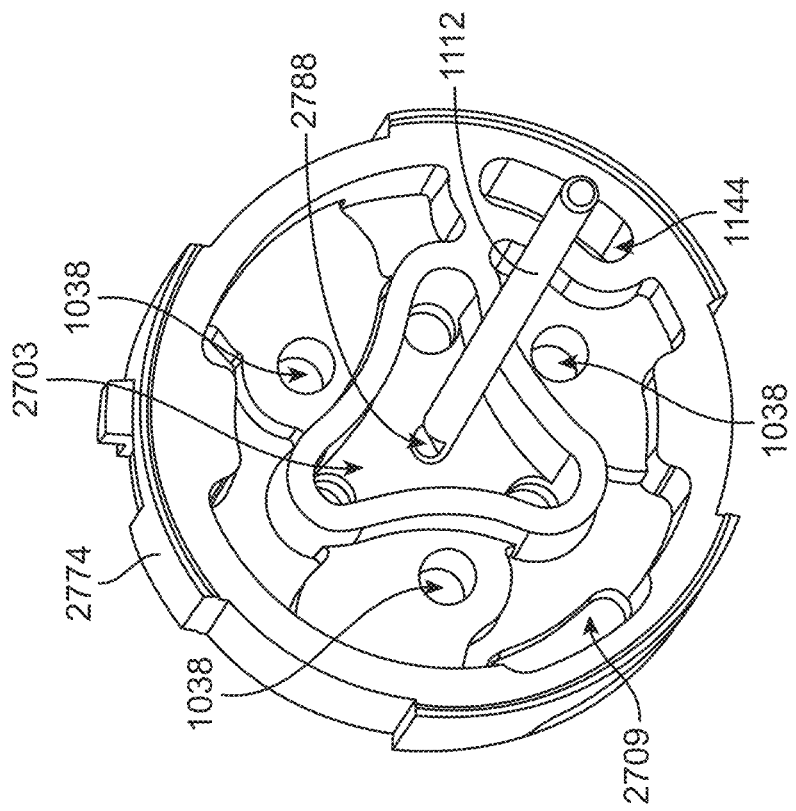
FIGS. 14A-14B illustrate views of a hand piece for cutting and aspirating material from an eye.
Figure 14A:
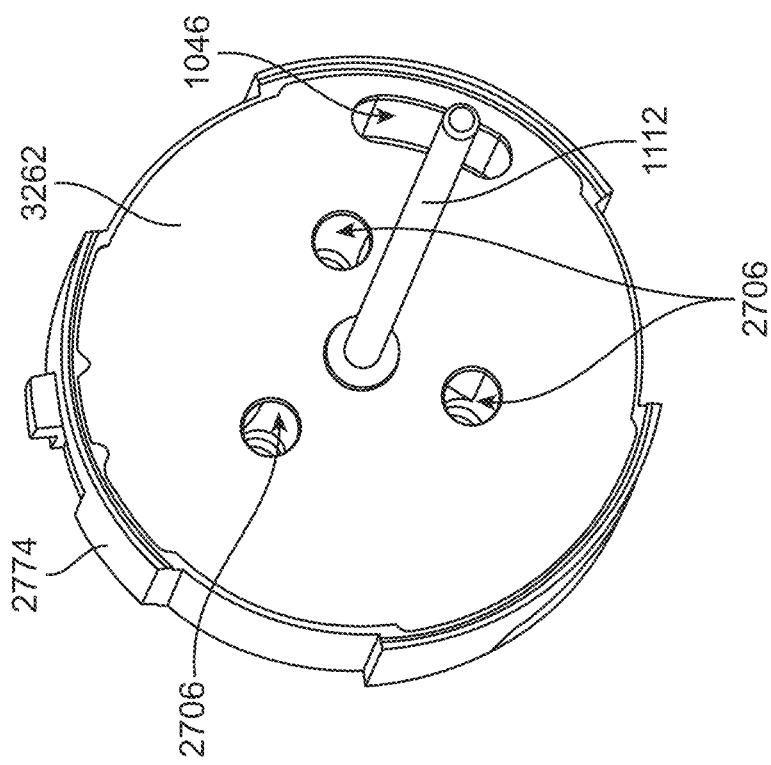

FIG. 14A shows a notch or proximal opening 2788 in the cutting tube 1112 positioned within the vacuum chamber 2703. Vacuum can pull lens material through the cutting tube 1112. The lens material may exit the lumen 1110 of the cutting tube 1112 through the proximal opening 2788 and enter into the vacuum chamber 2703 of the vacuum manifold 2774. Lens material is not intended to travel proximal of the proximal opening 2788 in the cutting tube 1112. The vacuum chamber 2703 is configured to be in fluid communication with the one or more pumping chambers 2705 via a respective opening 2706 regulated by a one-way valve 2707 (see FIG. 13I). The configuration of the one-way valve 2707 can vary including a duckbill valve, ball check valve, lift-check valve, stop-check valve and other types of valves that allow flow of fluid in a single direction and cut-off flow of fluid in the opposite direction. Movement of the pistons 2799 in a first direction within the pumping chambers 2705 (i.e. proximally or towards the rear of the hand piece) creates a vacuum that can be supplied to the lumen of the cutting tube 1112 through the openings 2706 on the vacuum manifold 2774 that surround the cutting tube 1112. A gasket 3262 separates the vacuum chamber 2703, which can be defined by the cavity in the center, and the evacuation chamber 2709 (see FIG. 14A). Upon supplying vacuum to the lumen of the cutting tube 1112, material from the eye is drawn into the lumen 1110 of the cutting tube 1112, emptied into the vacuum chamber 2703, and pulled through the one-way valve 2707 into the pumping chamber 2705. Movement of the pistons 2799 in a second, opposite direction within the pumping chambers 2705 (i.e. distally or towards the front of the hand piece) causes pressure to build within the piston manifold 2798 and expels material from the pumping chamber 2705 and out of the system. The material can be expelled from the system into a disposal enclosure coupled to an exit port as described elsewhere herein.

Again with respect to FIG. 13I, the vacuum manifold 2774 can additionally include an evacuation chamber 2709. The evacuation chamber 2709 is sealed off from the vacuum chamber 2703 such that material drawn into the system can be purged from the system without being pushed back out through the cutting tube 1112. The seal between the chambers 2703 and 2709 can be provided by one or more O-rings 2786. The vacuum chamber 2703 is configured to be in fluid communication with the one or more pumping chambers 2705 through respective one-way valves 2707 positioned within openings 2706. The evacuation chamber 2709 is in fluid communication with each of the one or more pumping chambers 2705 through other openings 1038 regulated by respective valves 2713. The configuration of the valves 2713 can vary including a ball type check valve. Movement of the pistons 2799 in a first direction within their respective pumping chambers 2705 (e.g. towards a proximal end of the hand piece 1030) draws material from the vacuum chamber 2703 into the pumping chamber 2705 through the valves 2707. Movement of the pistons 2799 in a second, opposite direction within their respective pumping chambers 2705 (e.g. towards the distal end of the hand piece 1030) pressure builds within the piston manifold 2798. The pressure opens the valves 2713 in the piston manifold 2798. The waste material may enter the vacuum manifold 2774 through the waste channels 1038 (e.g. three openings shown in FIG. 14A). The waste may combine in the vacuum manifold 2774 and exit the device through the evacuation chamber 2709. The evacuation chamber 2709 is shown in FIG. 14A as an oval-shaped channel that runs through the vacuum and piston manifolds 2774, 2798 although it should be appreciated that other shapes are considered herein. During this purge of material, the one-way valves 2707 between the one or more pumping chambers 2705 and the vacuum chamber 2703 prevents the backflow of material into the vacuum chamber 2703, the lumen 1110, and out the cutting tube 1112. However, the openings 1038 between the one or more pumping chambers 2705 and the evacuation chamber 2709 allows for the material to freely enter the evacuation chamber 2709 and ultimately out an exit or aspiration port 1154 of the evacuation chamber 2709 at least until flow is cut off by the valves 2713.

Again with respect to FIG. 13J, movement of the pistons 2799 in a proximal direction creates a vacuum within the pumping chamber 2705. The ball 2717 of the valve 2713 is pushed proximally by the spring 2719 away from opening 1038 between the pumping chamber 2705 and the evacuation chamber 2709 thereby opening the valve 2713. Upon movement of the pistons 2799 in a distal direction, fluid pressure builds within the pumping chamber 2705 increasing fluid pressure within the chamber and urging the material towards the opening 1038 of the valve 2713. The ball 2717 of the valve 2713 is pushed distally against the spring 2719 such that the spring 2719 compresses and the ball 2717 is urged against the valve opening 1038 thereby closing the valve. The pumping chambers 2705 are substantially devoid of material upon closure of the valve 2713. In some implementations, valves 2707 may be slightly compliant such as a silicone valve like a duckbill valve. The ball 2717 can be rigid and substantially non-compliant such as a hard plastic or metal material. The compliant valves may deform as a reverse positive pressure is imparted on them whereas the non-compliant valves do not deform. If the valve between the vacuum chamber 2703 and the pumping chamber 2705 is a compliant valve and the ball 2717 is substantially non-compliant, then as the piston is travelling distally and generating positive pressure to evacuate the material from the pumping chamber 2705, the positive pressure can cause a deformation of the compliant valve and a small purge or regurgitation of an amount of fluid out the cutting tube 1112. This regurgitation may occur on every back and forth cycle of the piston 2799. In some embodiments, the regurgitation may be optimized further by the design of the pumping chamber 2705. In the pumping chamber 2705, the outlet opening connecting the pumping chamber 2705 to the evacuation chamber 2709 may be located, for example, on the side of the chamber and configured such that the piston 2799 may travel beyond the outlet opening. In this embodiment, after the piston 2799 has moved distally beyond the outlet opening there is no other route for fluid evacuation. Therefore, as the pistons 2799 continue to travel distally creating a moment of positive pressure within the pumping chamber 2705 after closure of the valves 2713 that causes a short regurgitation of material at the distal end of the cutting tube 1112.

Figure 13C:
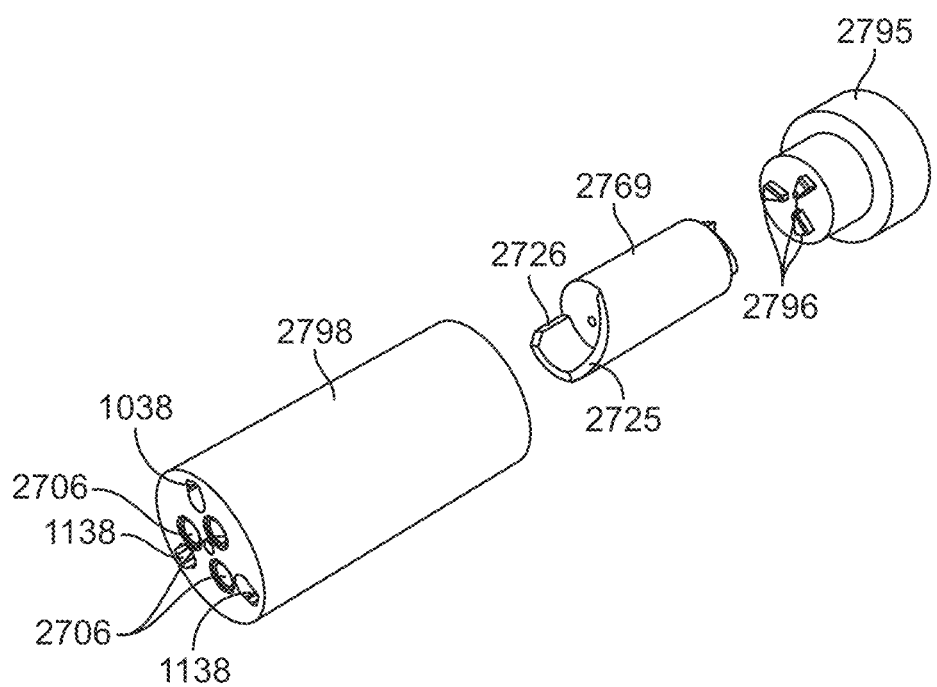
Figure 13D:
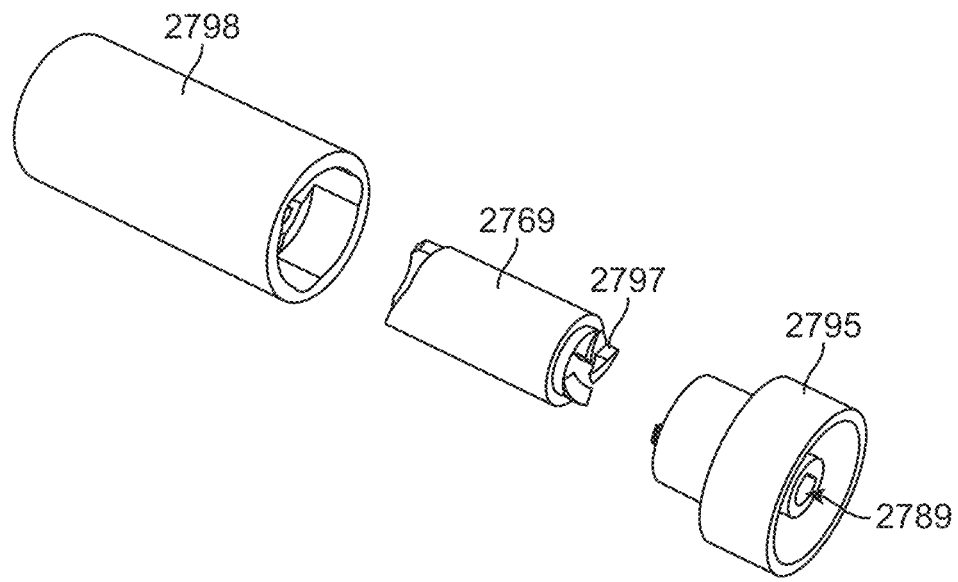
Figure 13F:
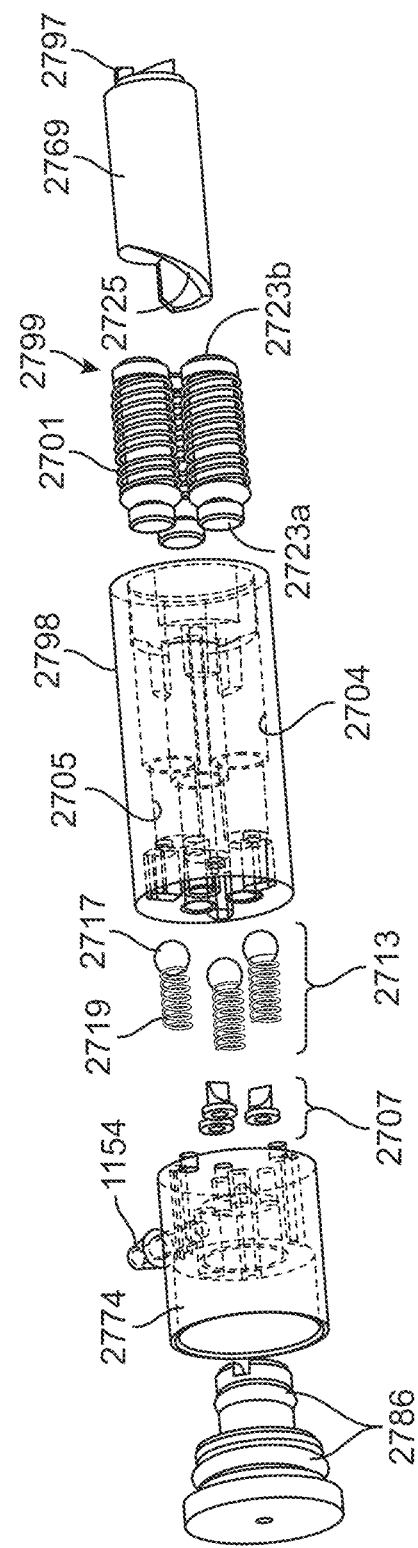
FIGS. 13F-13L are additional views of various components of the device of FIGS. 13A-13B.
Figure 13G:
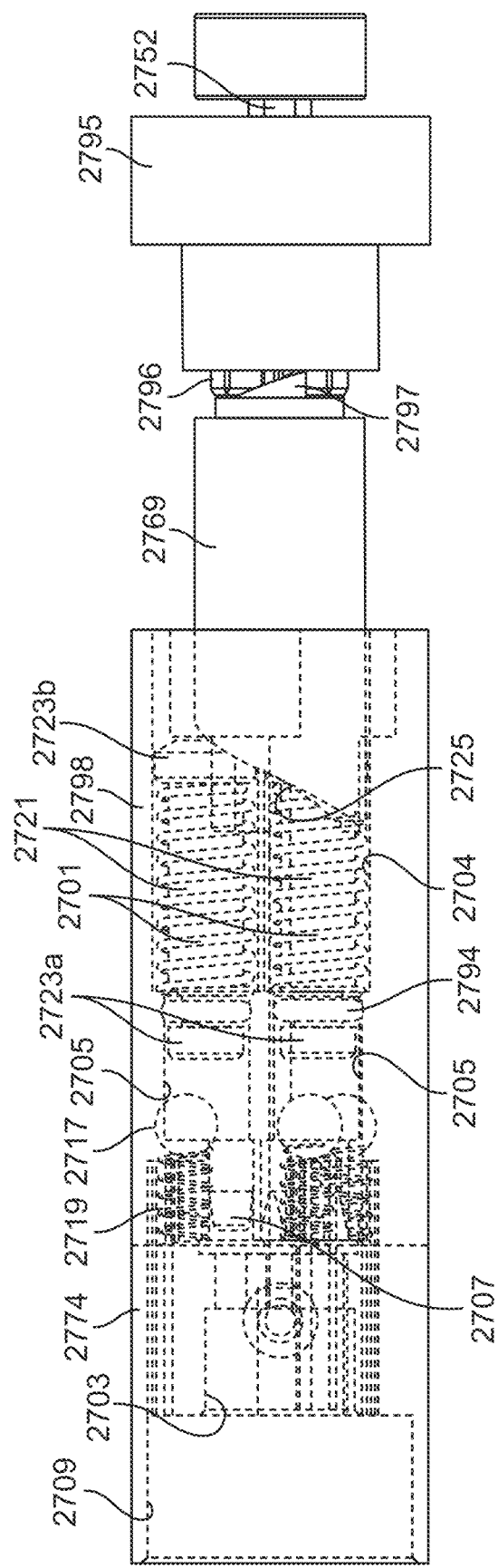
Figure 13H:
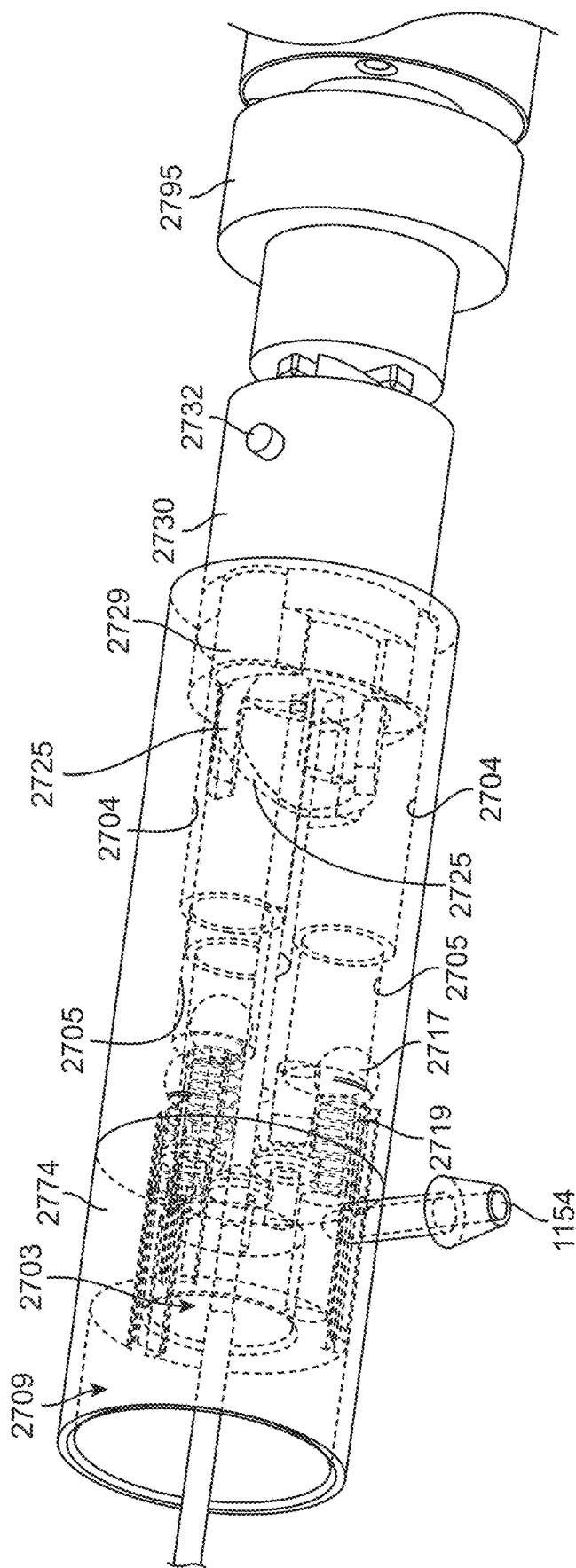
Figure 13I:
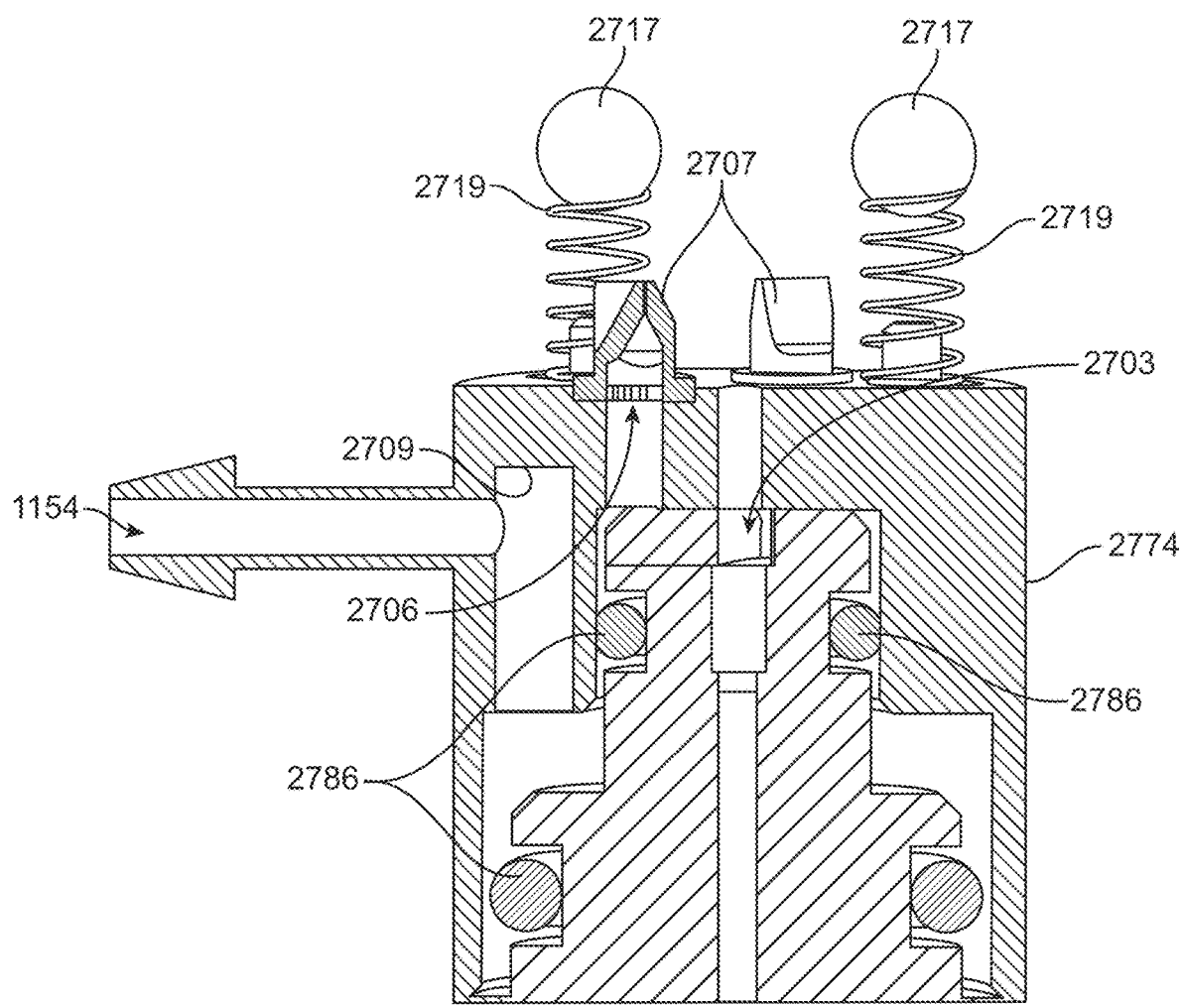
Figure 13J:
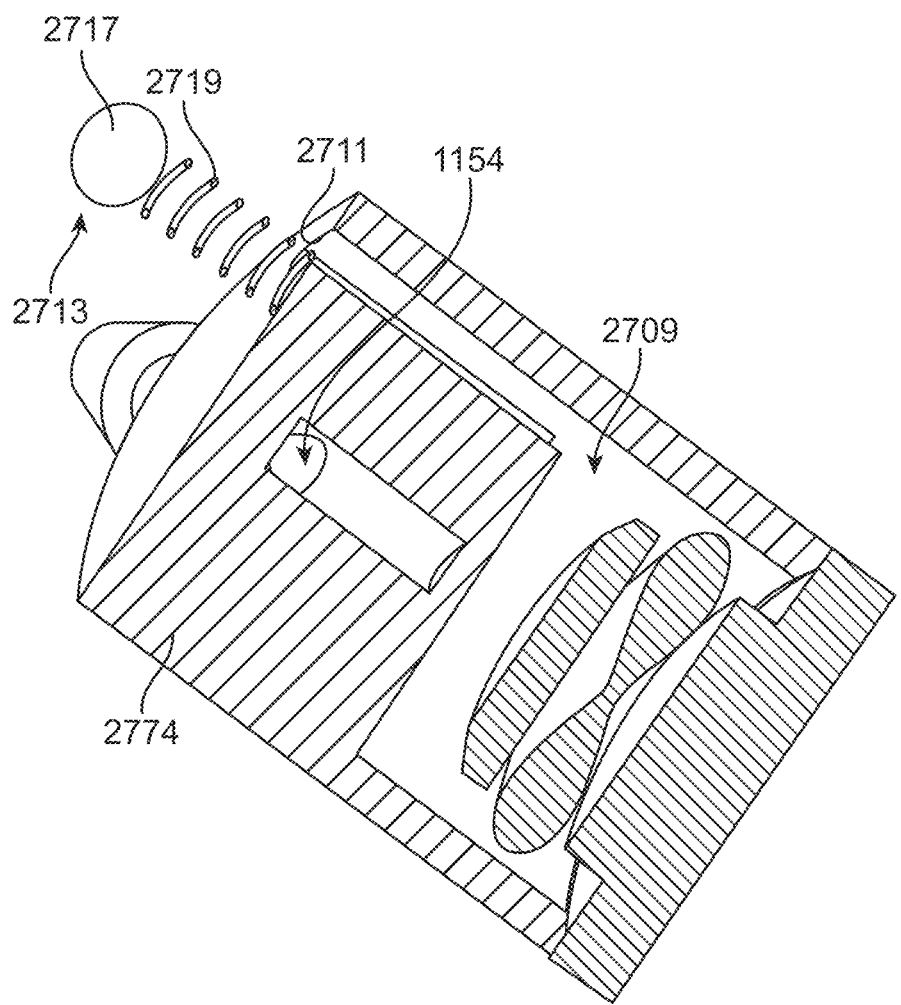
Figure 13K:
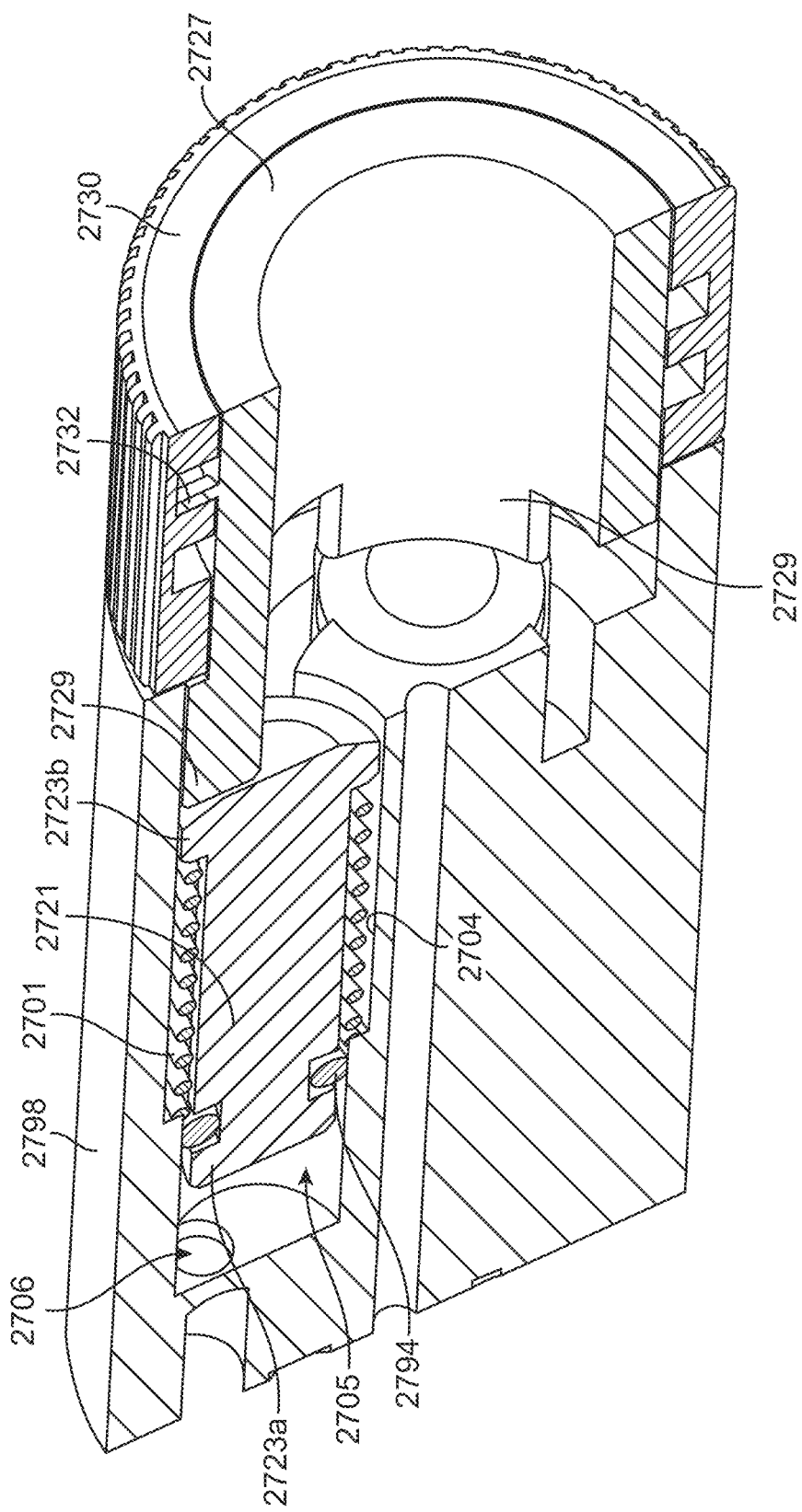
Figure 13L:
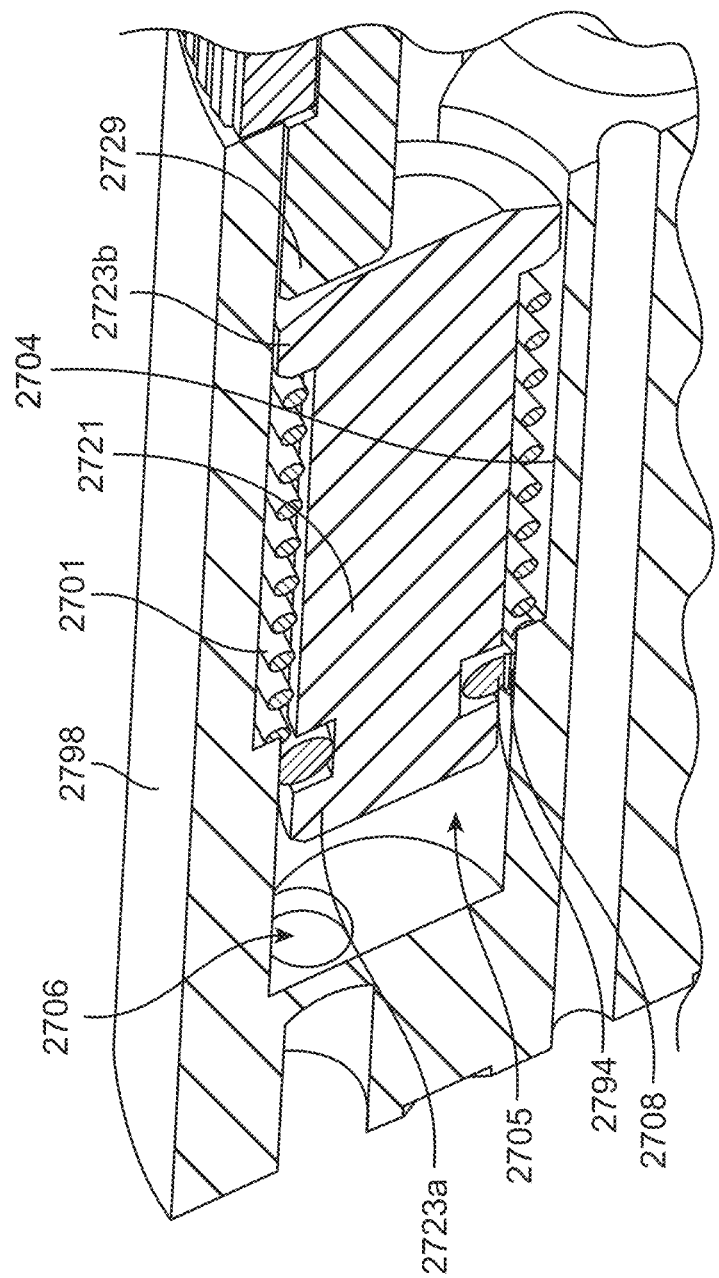
Figure 14B:
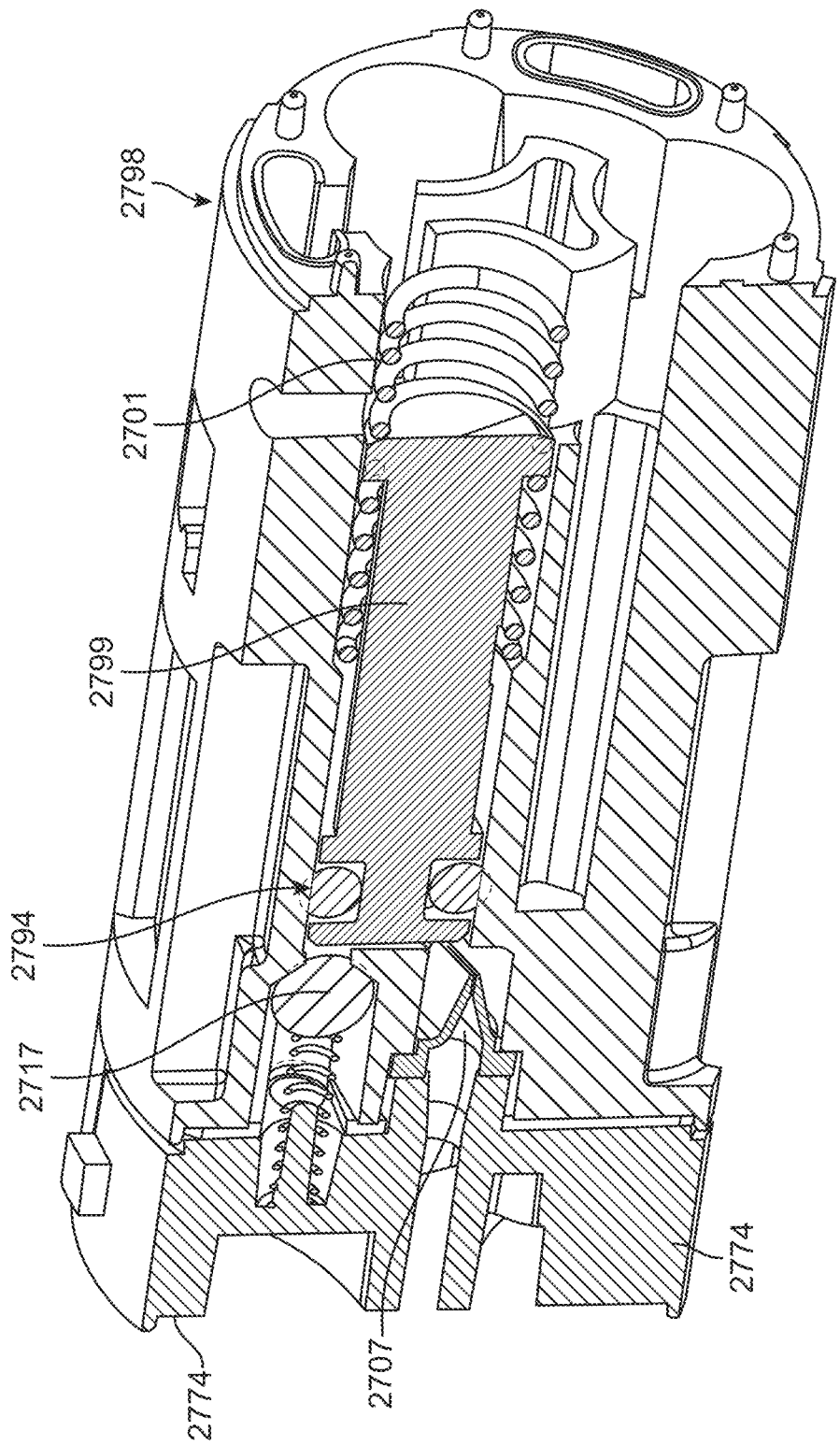

As best shown in FIGS. 13F-13G and also FIG. 13K-13L, and FIG. 14B, each of the pistons 2799 can include an elongate central piston rod 2721 surrounded by a spring 2701 extending between piston heads 2723a, 2723b. A distal piston head 2723a and sliding O-ring seal 2794 are positioned within the pumping chamber 2705. The piston rod 2721, spring 2701, and proximal piston head 2723b are positioned within a piston chamber 2704 within the piston manifold 2798 located proximal to the pumping chamber 2705. The distal piston head 2723a, sliding seal 2794, and piston rod 2721 are capable of sliding within the pumping chamber 2705. The pumping chamber 2705 has an inner dimension that is smaller than the piston chamber 2704 and the outer dimension of the spring 2701. Thus, as the piston 2799 move towards the distal end region of the pumping chamber 2705, the spring 2701 gets compressed within the piston chamber 2704 between the proximal piston head 2723b and the lower end of the pumping chamber 2705. The spring 2701 is biased to urge the piston 2799 proximally towards a proximal end of the pumping chamber 2705.

The hand piece can include a rotating cam 2769 having a proximal end operatively coupled to a motor either directly or via a motor coupler. The rotating cam 2769 can convert rotary motion of the motor into linear motion of the pistons 2799. The spring 2701 is biased to urge the pistons 2799 proximally towards the proximal end of the pumping chamber 2705. The rotating cam 2769 positioned proximal to the pistons 2799 is configured to urge the pistons 2799 distally towards the distal end of their respective pumping chambers 2705. As the cam 2769 rotates, it applies a distally-directed force sequentially against the proximal pistons heads 2723b of the pistons 2799. The springs 2701 of the pistons 2799 are, in turn, sequentially compressed. Upon further rotation of the cam 2769, the distally-directed force against the proximal piston heads 2723 is sequentially removed and the springs 2701 sequentially urge the pistons 2799 backwards creating a vacuum within the respective pumping chambers 2705 through the one-way valves 2707.

As best shown in FIGS. 13C-13E, the rotating cam 2769 can couple with a motor coupler 2795. The motor coupler 2795 can have a bore 2789 in a proximal end configured to receive the gear head 2752 and one or more projections 2796 on a distal end. The projections 2796 are configured to abut and engage with corresponding wedged-shaped projections 2797 on the proximal end of the cam 2769. The cam 2769 rotates as the gear head 2752 rotates. A distal end of cam 2769 has a cam surface 2725 configured to provide reciprocal linear motion of the pistons 2799. The geometry of the cam surface 2725 can be designed to provide different motion profiles of the pistons 2799 in their respective bores and thereby create different vacuum profiles (i.e. smooth continuous, continuous with spikes in negative pressure, or discontinuous pulsed negative pressure). The cam surface 2725 can be elliptical, eccentric, egg, or snail-shaped. During a first fraction of rotation of the cam 2769, the proximal piston heads 2723b slide along the ramped portion of the cam surface 2725 and the piston 2799 is moved distally along the longitudinal axis of the device. During a second fraction of rotation of the cam 2769, the proximal piston heads 2723b slide past the cam surface 2725 that terminates at ledge 2726. When the piston heads 2723b drop off ledge 2726 the distally-directed force against the pistons 2799 by the cam 2769 is released. The spring 2701 surrounding the piston rod 2721 urges the proximal piston head 2723b in a proximal direction towards the proximal end region of the piston chamber 2704. A complete revolution of the cam 2769 therefore allows for axial movement of each piston 2799 in succession. The piston heads 2723b slide along the cam surface 2725 and extend in the distal direction at a first rate and the piston heads 2723b drop off the cam surface 2725 and retract in the proximal direction at a second rate that is much faster than the first rate. The timing of this piston movement can vary based on the geometry of the cam surface 2725 and the location of the ledge 2726 relative to the cam surface 2725. For example, the timing of when one piston retracts to create a negative pressure within the chamber relative to when the next piston retracts to create a negative pressure can be a function of the cam surface 2725 geometry. The cam surface 2725 can incorporate a ledge 2726 such that each piston retracts quickly upon reaching the ledge 2726 as shown in FIG. 13C. The piston extends at a first rate in a distal direction as it moves along the cam surface 2725 and then at a second, faster rate in the proximal direction as it drops off the ledge 2726. In other implementations, the cam surface 2725 has a first ramp connected to the ledge 2726 by a second ramp. The first ramp of the cam surface 2725 allows for gradual extension of each piston and the second ramp allows for gradual retraction of each piston. Thus, each piston will gradually retract a distance before the piston drops off the ledge 2726 to quickly retract the rest of the rearward travel. Movement of the pistons involved in creating aspiration forces and movement of the cutting tube can be linked due to the rotating cam mechanism, as described in U.S. Patent Publication No. 2018/0318133, published Nov. 8, 2018, which is incorporated by reference herein.

The vacuum pulses can be designed to occur suddenly, for example, by a piston 2799 falling off the ledge 2726 of the cam surface 2725 and being pushed proximally towards the proximal end of the pumping chamber 2705 by the piston spring 2701. The timing of this retraction due to the ledge 2726 can be leveraged to achieve a more pulsatile vacuum profile. Pulsatile vacuum can be beneficial for breaking up the lens and removing the lens material from the eye in that the peak vacuum level can be higher for these short bursts of time than can be achieved if steady vacuum is applied because the flow rate is kept below a nominal amount (e.g. 50 cc/minute). High peaks of vacuum are created, but a low overall flow rate can be maintained.

Figure 15A:
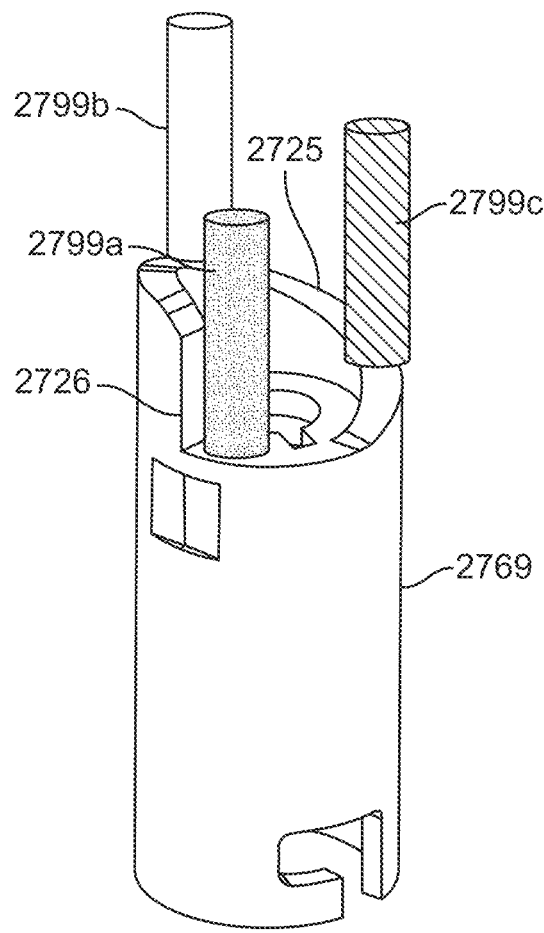
FIG. 15A schematically illustrates piston movements on a cam surface.

The timing of when a first piston is retracting and the next piston retracts can be a function of the geometry of the cam surface 2725 and the relative movements of the pistons within the piston chamber. The vacuum pulses can be designed to occur more smoothly such that the vacuum provided is substantially continuous, rather than discontinuous with momentary pauses between vacuum pulses. In some implementations, a first piston may retract and the second piston not start retracting until after a dwell period of the first piston retraction (see FIG. 15A) thereby creating a pulsatile vacuum profile. As described above, the device can include a cam 2769 having a cam surface 2725 configured to provide reciprocal linear motion of the pistons 2799. FIG. 15A illustrates in schematic movement of the pistons 2799a, 2799b, 2799c along the cam surface 2725 of the cam 2769. The cam surface 2725 terminates at a sharp drop-off or ledge 2726. During rotation of the cam 2769, the pistons 2799a, 2799b, 2799c slide along the cam surface 2725 and thereby extend in a distal direction. Upon reaching the ledge 2726, a first piston 2799a drops off the ledge 2726 retracting quickly in a proximal direction creating a spike in negative pressure. The geometry of the cam surface 2725 creates a dwell time of no negative pressure before the next piston 2799b reaches the ledge 2726 and retracts creating a second spike in negative pressure. The result is a series of discontinuous pulses of negative pressure.

Figure 15D:
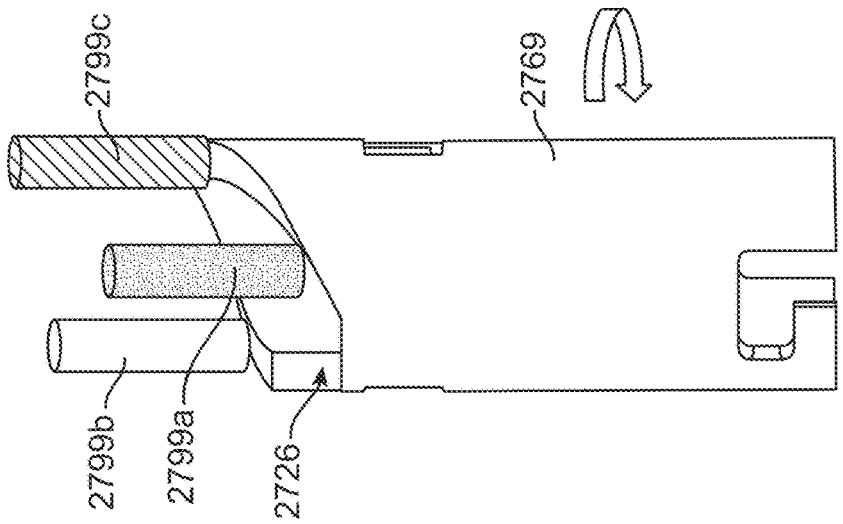
FIGS. 15B-15D schematically illustrate piston movements on another cam surface.
Figure 15C:
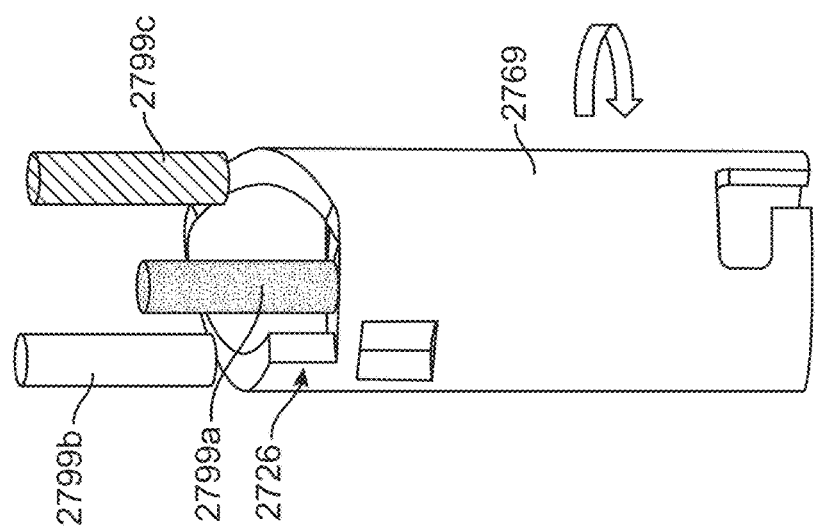
Figure 15B:
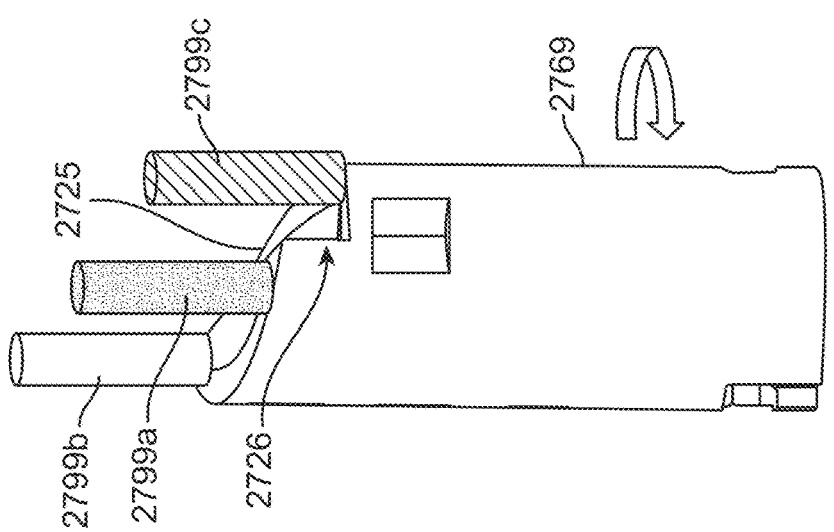
Figure 16D:
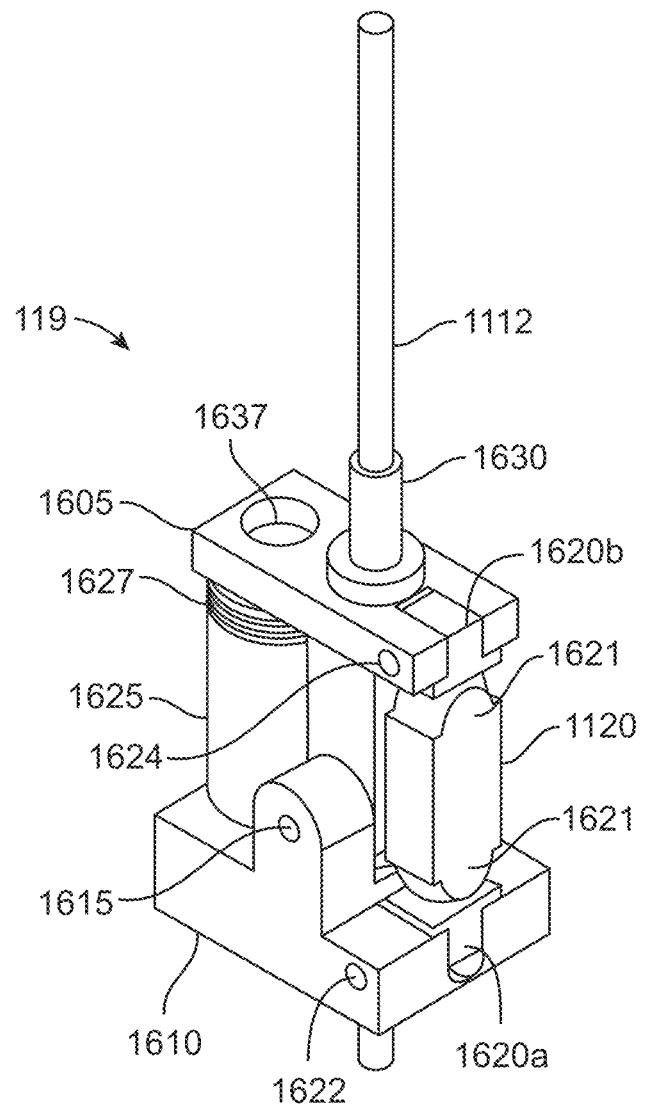
FIG. 16D illustrates the implementation of FIG. 16A having a dome-shaped interface between the piezoelectric stack and the off-set rocker.

In other implementations, the second piston may start retracting during a phase of the first piston retraction such that the vacuum profile is smoother and more continuous. FIGS. 15B-15D illustrate in schematic an implementation of the cam 2769 where the geometry of the cam surface 2725 is designed to having a more gradual slope for piston retraction prior to terminating at the ledge 2726. The geometry of the cam surface 2725 can be designed such that one of the plurality of pistons 2799 is retracting (i.e. creating a negative pressure within the pumping chamber 2705) at a constant rate. FIG. 15B shows the first piston 2799a near the end of its proximal travel within the piston chamber just prior to the ledge 2726. The second piston 2799b is poised to begun its retraction along the gradual slope prior to the first piston 2799a dropping off the ledge 2726. FIG. 15C and FIG. 15D illustrate further rotation of the cam 2769 and movement of the pistons along the cam surface 2725. Before the second piston 2799b drops off ledge 2726, the third piston 2799c will begin its retraction along the gradual slope of the cam surface 2725. This timing of piston retractions creates a flow rate of fluid out of the eye that is substantially continuous compared to the geometry of the cam surface 2725 shown in FIG. 15A that is discontinuous with moments of no vacuum being drawn. However, the presence of the ledge 2726 can create small spikes in negative pressure on top of the continuous negative pressure being applied by the retracting pistons. The first piston 2799a retract a first distance along the cam surface 2725 at a first rate thereby creating a first negative pressure. The second piston 2799b can start retracting at the first rate along the cam surface 2725 prior to the first piston 2799a dropping off the ledge 2726 maintaining that negative pressure. The first piston 2799a then drops off the ledge 2726 retracting the remaining distance at a second, faster rate thereby creating a spike in negative pressure.

As best shown in FIGS. 13K-13L, a piston stop 2727 can be coupled to a proximal end region of the piston manifold 2798. The piston stop 2727 can be a generally cylindrical element surrounding the rotating cam 2769. A distal end region of the piston stop 2727 can define one or more projections 2729 configured to project into a proximal end region of each of the piston chambers 2704 in the piston manifold 2798. The projections 2729 abut against the proximal piston heads 2723b of respective pistons 2799 when positioned at a proximal-most end region of their respective piston chambers 2704. For example, if the hand piece 1030 includes three pistons 2799 positioned in three piston chambers 2704, the piston stop 2727 includes three projections 2729 configured to abut against the proximal piston head 2723b of each of the three pistons 2799. The piston stop 2727 provides a hard stop to the linear travel of the pistons 2799 in a proximal direction upon expansion of the springs 2701 and thus, the overall volume of the pumping chamber 2705 that can be achieved. The relative position of the projections 2729 within the piston chambers 2704 can be adjustable. In some implementations, an adjustment ring 2730 can be positioned around an outer surface of the piston stop 2727 and available to a user through one or more windows 2731 in the housing of the hand-held portion 1030 (see FIGS. 13A-13B). The adjustment ring 2730 can have a threaded inner surface configured to engage with a corresponding pin 2732 on an outer surface of the piston stop 2727. The pin 2732 is configured to slide within the threads of the adjustment ring 2730 such that the piston stop 2727 travels axially along the longitudinal axis of the device. As the piston stop 2727 is adjusted to be positioned further distal relative to the piston manifold 2798, the projections 2729 extend further into the piston chambers 2704 and limit the linear travel of the pistons 2799 in the proximal direction upon expansion of the springs 2701. This, in turn, limits the size of the pumping chamber 2705. As the piston stop 2727 is adjusted to be positioned more proximally relative to the piston manifold 2798, the projections 2729 are withdrawn from the piston chambers 2704 and do not limit (or limit to a lesser degree) the linear travel of the pistons 2799 in a proximal direction upon expansion of the springs 2701. This, in turn, maximizes the size of the pumping chamber 2705. The piston stop 2727 also can be adjusted to determine the type of vacuum applied by the pistons within their respective chambers 2704 (e.g. smooth continuous vacuum or smooth continuous with spikes in pulsatile vacuum), as will be described in more detail below.

In some implementations, the vacuum source can create a sudden rise in vacuum forming a vacuum profile that causes the cornea and the eye to effectively "bounce" up and down during application of pulsed vacuum. For example, when the pistons 2799 are sprung backwards they can create the sudden rise in vacuum forming a vacuum profile that resembles a "saw tooth" (i.e. suction-pause-suction). Limiting the backwards travel of the pistons 2799 inside their respective pumping chambers 2705 can reduce the amount of suction impact or shock that is created each time the pistons are sprung backwards. The piston limit thereby limits the maximum suction created with each piston travel reducing the impact this abrupt suction can have on the eye. The vacuum created with each backwards travel of the piston 2799 can be greater than 500 mmHg up to about 700 mmHg.

In some implementations, the device can be switched between two vacuum modes. The first mode can be a substantially continuous vacuum mode without the spike in negative pressure due to the pistons 2799 dropping off the ledge 2726. The second mode can be a substantially continuous vacuum mode with the spikes in negative pressure. When in the first mode, the piston retraction can be limited to a fraction of the maximum piston travel within the chamber. For example, the piston stop 2727 can be selectively used to limit the piston travel within its chamber to a distance less than the maximum distance. As described elsewhere herein, the device can include a piston stop 2727 coupled to a proximal end region of the piston manifold 2798. The piston stop 2727 can be a generally cylindrical element surrounding the cam 2769 such that the cam 2769 extends through the cylindrical piston stop 2727 to contact the proximal ends of the pistons 2799. The piston stop 2727 can include a projection 2729 configured to project into a proximal end region of its respective piston chamber 2704 to make contact with the proximal ends of the pistons 2799. Thus, both the cam 2769 and the projections 2729 of the piston stop 2727 are configured to contact the proximal ends of the pistons 2799, the cam 2769 on an inner region and the projections 2729 on an outer region. The projections 2729 of the piston stop 2727 can provide a hard stop to the linear travel of the pistons 2799 in a proximal direction. For example, maximum piston travel within its piston chamber can be a distance of 5 mm. The projection 2729 of the piston stop 2727 can be advanced into the piston chamber by 2 mm to thereby limit proximal retraction of the piston 2799 to a distance of 3 mm rather than the maximum 5 mm. As the cam 2769 turns and the pistons 2799 extend and retract along the cam surface 2725, the projections 2729 of the piston stop 2727 can effectively prevent the pistons 2799 from dropping off the ledge 2726 creating a smooth, continuous negative pressure without the spike in negative pressure. When the projections 2729 of the piston stop 2727 are withdrawn from the piston chamber, the pistons 2799 can once again travel the maximum distance and can drop off the ledge 2726 creating a spike in negative pressure.

In some implementations, the hand piece is limited from achieving maximum vacuum by incorporating a feature that automatically bypasses the cutting tube 1112 depending on whether a threshold vacuum is reached. For example, a bleed valve or other bypass mechanism can be incorporated to prevent a threshold amount of vacuum from being applied at a distal opening of the cutting tube 1112 and into the eye. A bypass to turn on or off the suction can limit the maximum amount of vacuum that can be generated within the eye even if the opening into the cutting tube 1112 is clogged. This bypass can prevent the vacuum from building in the event of a blockage to create less surge upon removal of that blockage. The bypass mechanism can be adjustable or selective such that a user can choose whether or not they want the potential for maximum vacuum or something less than maximum vacuum applied.

It can be desirable to limit the maximum vacuum pressure that can be achieved with each proximal travel of each piston. Limiting the maximum vacuum can provide additional safety with regard to the capsular bag and the eye as a whole. For example, the impact the system has on the integrity of the capsular bag and the anterior chamber can be directly related to the degree of suction applied at the distal tip. Limiting the overall vacuum pressure (e.g. by at least about 2%, 3%, 4%, 5%, 10%, 15%, 20%, 25%, up to about 50% of maximum vacuum otherwise achievable) can prevent issues such as tearing of the capsular bag or "trampolining" of the anterior chamber.

FIG. 13L illustrates an implementation of a vacuum bypass feature 2708 configured to limit the maximum vacuum pressure in each pumping chamber 2705. The bypass feature 2708 can have any of a variety of configurations. In an implementation, the bypass feature 2708 can be a small longitudinal indentation, divot or groove in the cylindrical wall of each pumping chamber 2705 (see FIG. 13L). As described above, the piston 2799 can include an elongate central piston rod 2721 surrounded by a spring 2701 extending between piston heads 2723*a*, 2723*b*. A sliding O-ring seal 2794 can be positioned around the distal piston head 2723*a* that maintains a vacuum within the pumping chamber 2705. The piston 2799 shown in FIG. 13L is positioned in the cylindrical pumping chamber 2705 near the end of its proximal travel path such that proximal piston head 2723*b* abuts against the piston stop 2727. When the piston head 2723*b* abuts against the piston stop 2727, the seal 2794 can be aligned with the bypass feature 2708 near the proximal end of piston travel. The bypass feature 2708 can have a length along the longitudinal axis of the cylindrical chamber such that at least a portion of the feature 2708 is located distal to the seal 2794 and at least a portion of the feature 2708 is located proximal to the seal 2794. The presence of the bypass feature 2708 on both distal and proximal sides of the seal 2794 (i.e. the higher and lower pressure sides of the chamber 2705) means an amount of ambient air can bleed momentarily from the higher pressure side into the lower pressure side of the chamber 2705 (i.e. distal to the seal 2794) at the proximal end of piston travel. The leak or bleed of ambient air can limit the extent of the vacuum pressure that would otherwise be achieved upon retraction of the piston 2799 in the proximal direction. The venting of the aspiration cavity can be to the atmospheric air or to the irrigation fluid pathway, to the waste fluid pathway, or any other cavity allowing for fluid or air to enter the aspiration cavity and the vacuum level achieved within the aspiration cavity is decreased. The venting can release the vacuum level within the aspiration cavity as well as reduce the maximum achievable vacuum level during operation. The bypass feature 2708 can be designed to achieve a desired maximum pressure value depending on a length, width, and/or depth of the groove as well as the number of grooves incorporated. The geometry of the bypass feature 2708 can also control the speed at which this vacuum pressure is created with each sequential piston retraction.

The bypass feature 2708 can vent the vacuum to atmosphere passively, as described above, or actively. For example, the bypass feature 2708 can be user-actuated as will be described in more detail below. The bypass feature 2708 can have an adjustable and/or user-selectable geometry to provide additional user control over the desired maximum pressure value that can be achieved. In an implementation, the bypass feature 2708 can be a small hole extending through the wall of the pumping chamber 2705. The diameter, length, and/or location of the hole can be variable and selectable by a user so as to achieve the desirable control of the maximum suction pressure achieved.

In some implementations, the device can incorporate a venting mechanism that can be useful in certain situations, for example, when the capsular bag is inadvertently captured in or lens material occludes the distal end of the cutting tube 1112. Similar to the bypass feature 2708 described above, the venting mechanism can include a small hole through the wall of the pumping chamber 2705 that can be selectively exposed or covered. The hole can be covered and/or exposed by a movable element actuatable by a button or other input on the user interface of the device allowing for a user to vent any accumulated vacuum in the pumping chambers 2705 to the atmosphere. Venting the vacuum allows, for example, material such as the capsular bag to be released from the tip of the cutting tube 1112. Selective activation of the venting mechanism can include pressing a button that moves a movable element normally covering the hole exposing it to atmosphere. Alternatively, selective activation of the venting mechanism can include pressing a button that moves a movable element causing it to cover a normally open hole thereby preventing venting to the atmosphere. In an implementation, the button can be coupled to the multi-stage trigger 1180 of the device described elsewhere herein. As an example, when the trigger 1180 is at its neutral state and the device is at rest, the vacuum can be vented and the suction within the system dissipates. When the trigger 1180 is depressed to activate suction, the venting can be shut off. In this example, a user having the capsular bag sucked into the tip of the device (or a piece of lens occluding the lumen) can simply let go of the trigger 1180 to vent and release the tissue.

The venting purge mechanism can additionally create a small volume of retrograde flow of fluid out the distal tip of the device in addition to venting the tip of the cutting tube 1112. The small fluid flow at the tip can aid in fully releasing the bag or any other materials causing a clog. In this implementation, the button to actuate the purge mechanism can be a depressible button that when depressed can force a small volume of fluid out the irrigation outlet. As such, releasing the trigger 1180 can cause venting of accumulated vacuum in the pumping chambers 2705 and pressing the purge button can urge fluid out the distal tip to further push the capsular bag away.

Figure 22C:
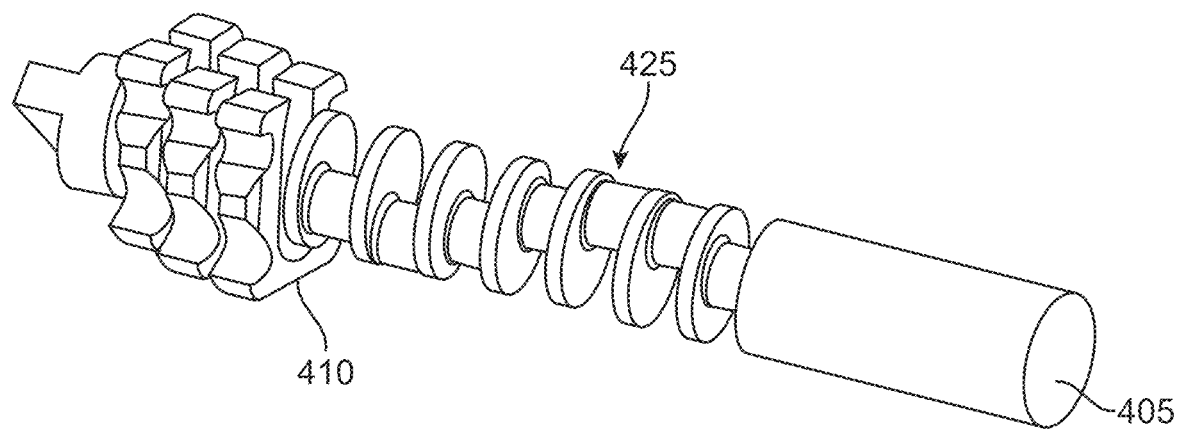
FIGS. 22C-22D show a camshaft of the aspiration pump of FIG. 22A.
Figure 22D:
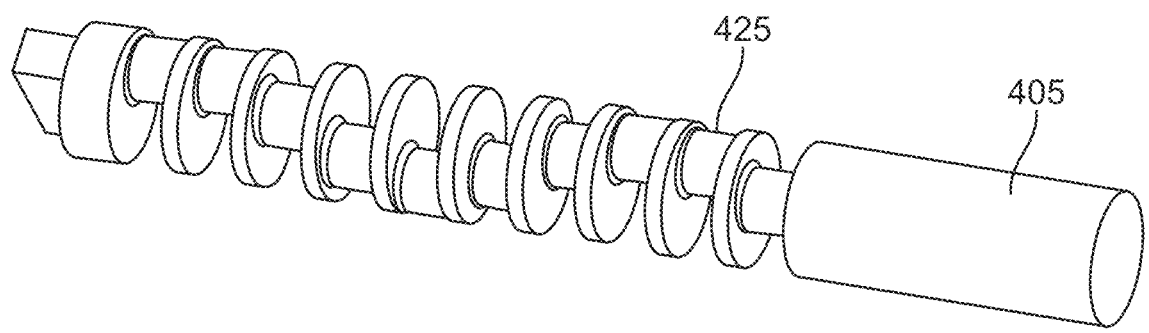

FIGS. 22A-22B show perspective and top views of an implementation of an aspiration pump 1014 for incorporation within a disposable, working portion 1031 configured to provide smooth, continuous aspiration through the cutting tube 1112. The working portion 1031 can be used for procedures in which smooth flow aspiration through an oscillating cutting tube 1112 is desired. FIGS. 22C-22D show a camshaft 405 of the aspiration pump 1014 of FIG. 22A.

The aspiration pump 1014 can be a linear peristaltic pump having a symmetrical double chamber pumping manifold 420, a central camshaft 405 extending longitudinally through the manifold 420 along longitudinal axis A, a plurality of cam followers 410, and a pair of peripheral tubes 415. The pumping manifold 420 can be disposed within the working portion 1031 between a proximal manifold and a distal manifold. The camshaft 405 can couple on a proximal end region of the camshaft 405 to a drive shaft such as via the rotating camshaft coupler 2795 in the disposable portion 1031. As the pump motor 1115 spins the drive shaft drives rotation of the camshaft 405 thereby powering the aspiration pump 1014. The camshaft 405 can also couple on a distal end region of the camshaft 405 to the cutting tube 1112 such as via rotating cam follower.

Figures 23A, 23B:
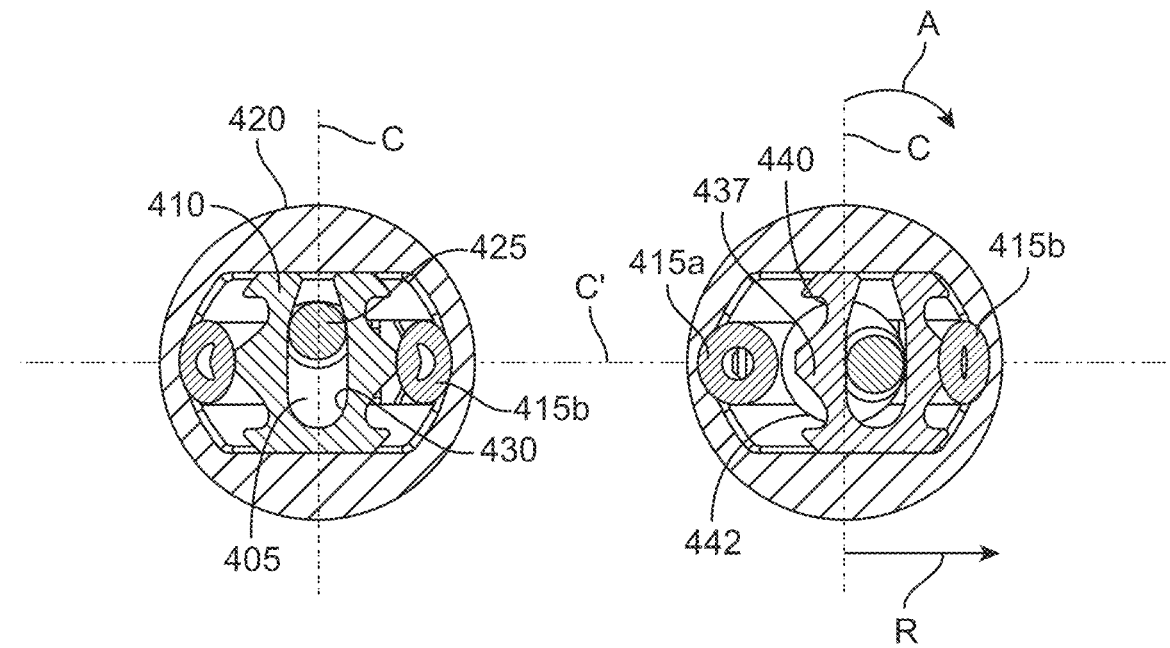
FIGS. 23A-23D show end views of the aspiration pump of FIG. 22A illustrating side-to-side motion of a cam follower as the camshaft rotates.

The two tubes 415 can be positioned on either side of a centerline C of the pumping manifold 420 (see FIG. 23A). The two tubes 415 can extend through the pumping manifold 420 in a substantially straight manner such that each forms a longitudinal axis T (see FIG. 22B) through the pumping manifold 420 that are positioned parallel with the longitudinal axis A of the camshaft 405 extending through the pumping manifold 420. A first tube 415a of the two tubes 415 can be positioned on one side of the camshaft 405 and a second tube 415b of the two tubes 415 can be positioned on a second, opposite side of the camshaft 405. A proximal flow path splits into two flow paths connected on a proximal end with the pair of tubes 415 within the proximal manifold (not shown). The two tubes 415 can combine distal to the pumping manifold 420 into the distal manifold (not shown). The distal flow path can be in fluid communication with the lumen of the distal cutting tube 1112.

FIGS. 22C-22D show the camshaft 405 of the aspiration pump 1014 in FIGS. 22A-22B. The camshaft 405 can incorporate a plurality of lobed cams 425 that work in time to drive the plurality of cam followers 410 side-to-side or towards and away from the pair of tubes 415 such that the tube experiences sequential, progressive compression, thereby pushing its fluid volume along its flow path. The pair of tubes 415 can be aligned with the longitudinal axis A (rotational axis) of the camshaft 405. The side-to-side motion of the cam followers 410 can be in a plane perpendicular to the longitudinal axis A of the camshaft 405 and the longitudinal axis T (see FIG. 22B) of each of the tubes 415. As an example, the tubing 415 can extend spatially parallel to or along the rotational axis of camshaft 405 through the pumping manifold. The tubing 415 can be compressed by the cam followers 410 along an axis that is substantially 90 degrees relative to the rotational axis of the camshaft 405. For example, the cam followers 410 can be driven side-to-side along the horizontal position or along the vertical position relative to the camshaft 405. Although the relative angle of the cam followers 410 and the tubing 415 can be more than or less than a 90 degree angle, the cam followers 405 do not translate axially along the side wall of the tubing 415 as occurs in conventional peristaltic pumps that use rollers, which compress and roll along the length of the tubing moving its fluid volume along its flow path.

Each of the tubes 415 can be sequentially compressed by the cam followers 410 in a wave-like fashion. The maximum extent of the compression closes off the tube, capturing a discrete volume of fluid that is urged along the tube's length resulting in aspiration fluid flow moving through the tubes 415. Conventional peristaltic pumps can involve the translation of a roller or other component along the longitudinal axis of the tubing thereby urging fluid through the tube. This sort of linear translation along a tube can lead to the creation of holes or tears in the side wall of the tubing as it wears over time. The aspiration pump 1014 described herein need not involve translation of a compression element along the longitudinal axis of the tubing 415 (i.e., axis T shown in FIG. 22B). Rather, the compression of each tube 415 is in a plane perpendicular to the longitudinal axis T of the tube 415. This arrangement avoids pulling or stretching of the tube and generates little to no friction on its side wall. In other words, the plurality of cam followers apply no force in a direction of the longitudinal axis T of the two tubes 415a, 415b. The chamber volume is maintained consistent and the pump 1014 has a lower risk of tube failure or loss of pump performance that can result from compression that translates along the tube length.

Figures 23C, 23D:
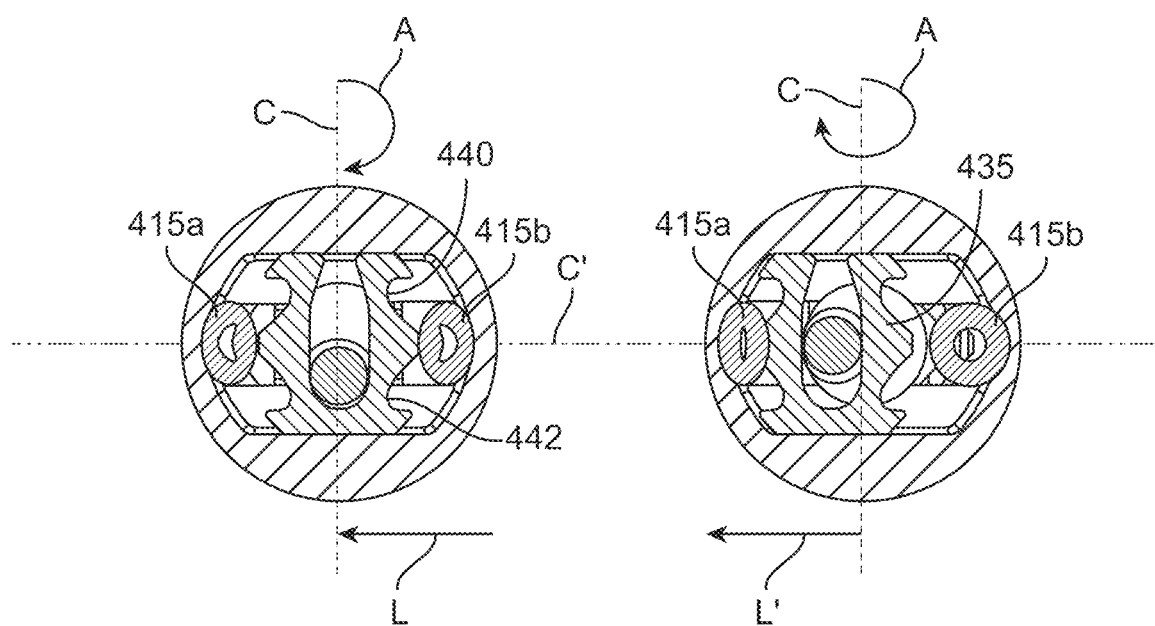

As best shown in FIGS. 23A-23D, each of the plurality of cam followers 410 can include an inner slot 430 configured to receive their respective cam lobes 425. The cam lobes 425 can travel up and down relative to and within the inner slot 430 as the camshaft 405 rotates about its longitudinal axis A. The cam followers 410 in turn are urged side-to-side by the cam lobes 425 relative to a centerline C of the pumping manifold 420. FIG. 23A shows one cam follower 410 aligned with the centerline C. The cam lobe 425 is shown substantially aligned with the centerline C and positioned in an upper end region of the slot 430 of the cam follower 410. As the camshaft 405 turns a first degree around its axis A along arrow A, the cam follower 410 is urged away from the centerline C along axis C' in the direction of arrow R and the cam lobe 425 travels downward through the slot 430 of the cam follower 410 (FIG. 23B). As the camshaft 405 turns a second further degree around its axis A along arrow A, the cam follower 410 is urged back towards the centerline C along axis C' in the direction of arrow L and cam lobe 425 travels further downward through the slot 430 of the cam follower 410 (FIG. 23C). As the camshaft 405 turns a third further degree around its axis A along arrow A, the cam follower 410 is urged away from the centerline C along axis C' in the direction of L' as cam lobe 425 travels back up through slot 430 of the cam follower 410 towards the upper end region of the slot 430 (FIG. 23D).

The side-to-side motion of the cam followers 410 can create incremental, sequential compressions of each tube 415 such that the aspiration created in the distal flow path that is in communication with the cutting tube is smooth or substantially non-pulsatile aspiration. The geometry of the camshaft 405 (e.g. pitch, length) as well as the number of cam lobes 425 and cam followers 410 can vary to achieve a particular timing along the longitudinal axis T of the tubes 415. The number of cam followers 410 in the pump 1014 can vary, for example, at least 2, 3, 4, 5, 6, 7, 8, 9, 10, up to about 20 cam followers 410. The number of cam lobes 425 and cam followers 410 can more closely approximate perfect smooth flow as the number of lobes and followers increases. For example, the implementation of the aspiration pump 1014 shown in FIG. 22B includes 10 cam lobes 425 and 10 cam followers 410. The aspiration pump 1014 can thereby create a smooth, sine wave sort of curve as each cam follower 410 is urged side-to-side to compress the opposing tubes 415.

Figure 24A:
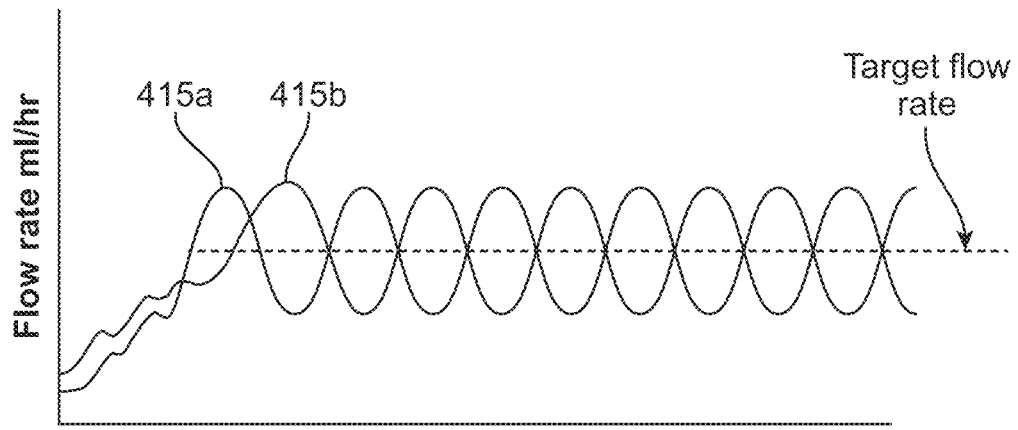
FIG. 24A shows an example of aspiration flow rate provided by an aspiration pump.
Figure 24B:
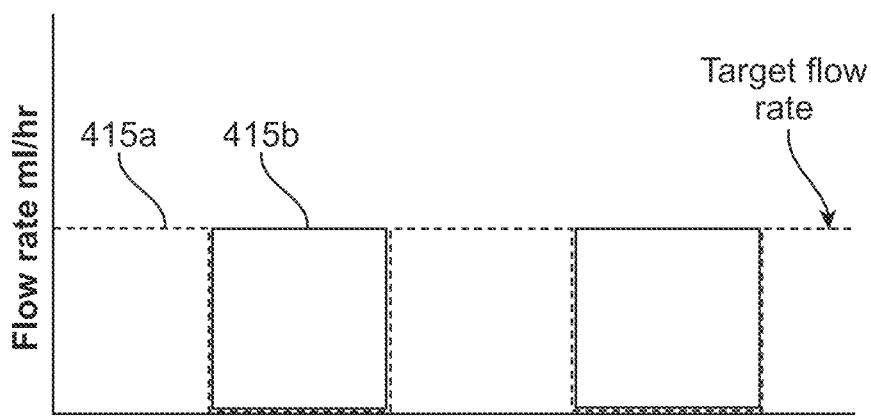
FIG. 24B shows another example of aspiration flow rate provided by an aspiration pump.

FIG. 24A shows how initially, the pump 1014 can undergo a warm-up period upon activation as the camshaft 405 starts rotating. The cam followers 410 are urged side-to-side within the pumping manifold 420 to sequentially compress the pair of tubes 415 and the negative pressure within the flow line of tube 415a and tube 415b builds. The flow rate through tube 415a can be offset from the flow rate through tube 415b such that the target flow rate achieved is substantially constant with minimal pulsatile flow through the distal flow path.

The pump 1014 can include fewer cam followers 410 than is shown in the embodiment of FIGS. 22A-22B. In such an implementation, the timing of the camshaft 405 can create a curve that is more like an off-on type of square curve (see FIG. 24B). The on-off square curve can provide a more consistent chamber length (i.e., the sealed volume within the tubing between the locations where it is closed off by the cam followers) compared to, for example, a helical driven peristaltic pump where the tube is squeezed shut using a more gradual motion. The cam lobes of the implementation of the pump shown in FIGS. 22A-22B follow a circular path relative to the device at large and a linear path relative to the cam follower. The cam followers compress the tubes on both sides. As it moves one direction, it compresses one tube and as it moves in the opposite direction, it compressed the opposite tube. However, the cam lobes need not be driven by a helical path with such gradual compression. Rather, the layout of the cam lobes can be positioned radially or lengthwise along axis T relative to one another such that the spacing between each cam lobe can create compression on the tube 415 to achieve the desired timing.

Again with respect to FIGS. 23A-23D, the shape of the cam followers 410 not only provides for the travel of the cam followers 410 in a side-to-side motion as the camshaft 405 spins. The shape of the cam followers 410 provides efficient compression of the pair of tubes 415. Each cam follower 410 can incorporate a first compression zone 435 on an outer surface of the cam follower 410 on a first side of centerline C and a second compression zone 437 on an outer surface of the cam follower 410 on a second, opposite side of centerline C. Each of the first and second compression zones 435, 437 can be arranged substantially aligned with the centerline C'. As the cam follower 410 moves along arrow R, the first compression zone 435 compresses tube 415b (FIG. 23B). As the cam follower 410 moves along arrow L', the second compression zone 437 compresses tube 415a (FIG. 23D). Each cam follower 410 can also include two displacement zones 440, 442 for each compression zone 435, 437. As the tubes 415 are compressed by the compression zones 435, 437, the corresponding two displacement zones 440, 442 can receive the material of the tubes 415 that are being compressed by the compression zones 435, 437 of the cam follower 410.

The pair of tubes 415 can extend in a straight line along longitudinal axis T and parallel with the longitudinal axis A of the camshaft 405. The pair of tubes 415 extend generally parallel to the rotational axis of the camshaft 405 through the pumping manifold. As such, the compression on the tubes 415 occurs in a side-to-side motion along a horizontal plane relative to the rotational plane of the camshaft, which can be in a plane perpendicular to the longitudinal axis A (and also axis T). This compression does not therefore translate axially along the sidewall of the tubing thereby providing the advantage of less wear on the tubing material. Additionally, the configuration of the pair of straight tubes 415 can provide additional side-to-side force on the cam follower 410. For example, as one tube 415a is being compressed by the cam follower 410, the opposing tube 415b that just got compressed by a cam follower 410 can spring back to its original shape. The spring force can help to compress the opposing tube 415. Each tube 415 can aid in causing compression of its partner by urging the cam follower 410 in the opposite direction of the compression.

As mentioned above, the proximal end region of the camshaft 405 can couple to the drive shaft such as via the coupler in the disposable portion 1031 and the distal end of the camshaft 405 can couple to the cutting tube 1112. Thus, the drive mechanism that drives the aspiration pump 1014 can also drive oscillation of the cutting tube 1112. Despite being physically coupled, the pump and the oscillation can be functionally decoupled. The pump 1014 can be configured to turn on at maximum flow levels and full aspiration potential by the drive mechanism. The aspiration delivered through the cutting tube 1112 can be controlled by a bleed valve. The bleed valve can be open to the atmosphere so that no aspiration is drawn through the cutting tube 1112 upon initiation of the pump 1014 despite the drive motor turning at full speed. The bleed valve can start to close upon actuation of a trigger 1180 such that aspiration through the cutting tube 1112 will slowly increase. The greater the trigger 1180 is actuated the greater the aspiration until the bleed valve achieves the fully closed position and full aspiration is directed through the lumen. The valve can be positioned distal to the aspiration pump 1014 and proximal to the cutter assembly.

The aspiration pump 1014 generally requires a slower turning speed for driving aspiration compared to the turning speed needed for oscillation of the cutting tube 1112. For example, in vitrectomy it can be desirable to achieve up to 5000 cuts per minute and to achieve a vacuum capability of 650 mmHg or 25 cc/minute volume. The instrument can incorporate a small transmission or gear train to effect a desired oscillation speed. The gear train can be positioned between the camshaft 405 and the cutting tube 1112 and can be configured to engage and disengage the cutting tube 1112 acting as a clutch mechanism in the oscillation of the tube 1112. A gear train can effect a fixed ratio between the cutting tube oscillation speed and the aspiration pump rotational speed. In some implementations, the aspiration pump 1014 can be activated and running at maximum speed. The valve can control delivery of aspiration through the lumen of the cutting tube 1112. The input 1180 can be actuated to engage or disengage the cutting of the cutting tube 1112.

The lobed cams 425 of the camshaft 405 can drive and cause motion of a plurality of cam followers 410 configured to sequentially compress tubing 415 and translate that generated aspiration pressure to the cutting tube 1112 positioned within an eye. The plurality of cam followers 410 can be driven by the cams of the camshaft 405 to move in a plane that is substantially perpendicular to the longitudinal axis to sequentially compress the tubing 415. As an example, the tubing 415 can extend spatially parallel to or along the z-axis, or the center of rotation of the camshaft 405. The tubing 415 can be compressed by the cam followers 410 along an axis that is aligned substantially 90 degrees relative to the z-axis. For example, the cam followers 410 can be driven side-to-side along the horizontal position or x-axis relative to the z-axis of the camshaft 405. The cam followers 410 can also be driven along the vertical position or along the y-axis relative to the z-axis of the camshaft 405. The relative angle of the cam followers 410 and the tubing 415 can be more than or less than a 90 degree angle as well. However, the cam followers 405 do not translate axially along the side wall of the tubing 415 (i.e. along the z-axis). The camshaft 405 can also drive oscillation of the cutting tube 1112, which can be a lens fragmentation working tip or a vitrectomy probe.

The configuration of the peristaltic pump within the disposable portion 1031 can vary and need not be a linear peristaltic pump. For example, the peristaltic pump can be a helical design or a horseshoe peristaltic pump.

Asymmetric Cutting Motion and Aspiration Profiles

As mentioned above, the hand pieces described herein can include a cutting tube 1112 or other elongate shaft configured to be inserted into the eye in a minimally-invasive manner to cut, aspirate, and/or inject material in the eye. The elongate shaft can be configured as a vitrectomy-style cutting element having a hollow, elongate member extending through an outer member with a side opening configured to capture and cut pieces of tissue. The elongate shaft can be configured as a phacoemulsification ("phaco") style tip, which also includes a movable cutting tube with or without an outer member. Oscillating movements of the elongate shaft can occur using any of a variety of mechanisms, such as a piezoelectric drive system described elsewhere herein. Certain oscillating movements can be created in a manner that avoids the deleterious effects that conventional phacoemulsification has on the delicate eye tissues such as corneal endothelial cells.

Conventional phacoemulsification can incorporate two main methods of action: 1) mechanical jack hammering, and 2) cavitation. In the case of jackhammering, the oscillating movements of the tip mechanically impacts the tissue at a high speed to break up the tissue into ever smaller fragments. Cavitation involves the creation of gas bubbles as a consequence of high velocity oscillation of the tip. Retraction speeds of the tip in conventional phacoemulsification are sufficient to create zones of pressure low enough to cause the formation of gas bubbles as dissolved gases are drawn out of the fluid. As the tip transitions from retraction to forward motion, these bubbles then collapse and implode, which results in very high temperatures (e.g. 3000° C.) and pressures (e.g. 10,000 atm). It is generally thought that the combination of high temperatures and high pressures helps to emulsify the tissue fragments. While the role cavitation plays in breaking up eye tissue is debatable, the role cavitation plays as the primary driver behind the deleterious effects of conventional phacoemulsification on the surrounding eye tissue during cataract surgery is not. High temperatures, shock waves, and the creation of free-radicals in the eye during conventional phacoemulsification are of concern to the health of the corneal endothelial cells.

The hand pieces described herein can include a drive mechanism that oscillates the cutting tube longitudinally in a manner that reduces, attenuates, or prevents problems of cavitation during conventional phacoemulsification. When in use, the drive mechanism retracts the cutting tube in a proximal direction with a retraction speed profile and advances the cutting tube in a distal direction with an extension speed profile. The retraction speed profile can be different from the extension speed profile. Additionally, the movement profile of the cutting tube can be coordinated with a vacuum profile. For example, while a pulse of vacuum is being applied through the cutting tube (i.e. through the distal opening), the cutting tube can be simultaneously fired in the distal direction. The pulsed vacuum can be internally generated within the hand held portion 1030 and/or externally generated and valved within the handle, as described elsewhere herein. Where the cutting tube is described as moving in forward and distal directions relative to the treatment site vibrations of the cutting tube are considered as well. The cutting tube can be vibrated in a similar fashion to conventional phacoemulsification machines. Thus, the cutting tube can be vibrated while a pulse of vacuum is applied and at some phase in the vacuum pulse or thereafter, the vibration and the vacuum can be turned off such that the system comes to rest before initiating a vibration-vacuum sequence again. The coordination between the movement and/or vibration of the cutting tube and the vacuum applied through the cutting tube is described in more detail below.

The maximum tip retraction speed can remain below the critical 'cavitation threshold speed' that would otherwise result in cavitation in the eye. The average retraction speed can be slow, i.e. below the cavitation threshold speed, but the average extension speed can be fast, i.e. close to or higher than the average retraction speed of a typical phacoemulsification tip. Thus, the benefits of mechanical jackhammering can be achieved while the deleterious effects of cavitation are entirely avoided.

Figure 10A:
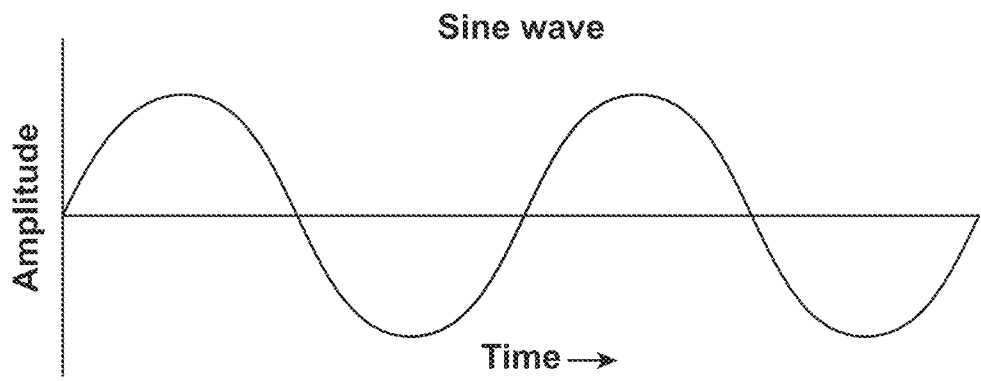
FIG. 10A shows a symmetric, sinusoidal motion profile of a cutting tube.
Figure 10B:
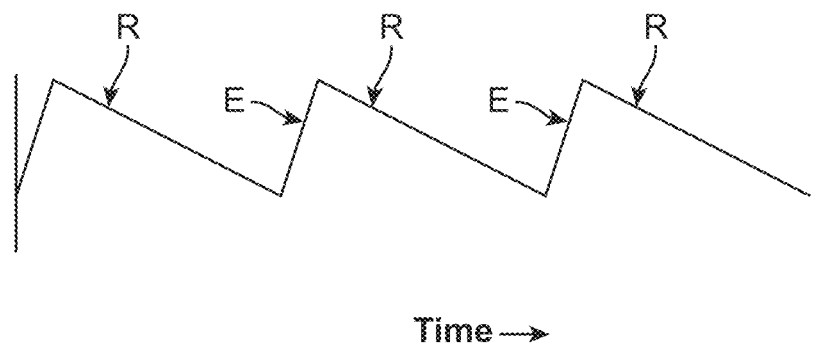
FIG. 10B shows an asymmetric, non-sinusoidal motion profile of a cutting tube.
Figure 10C:
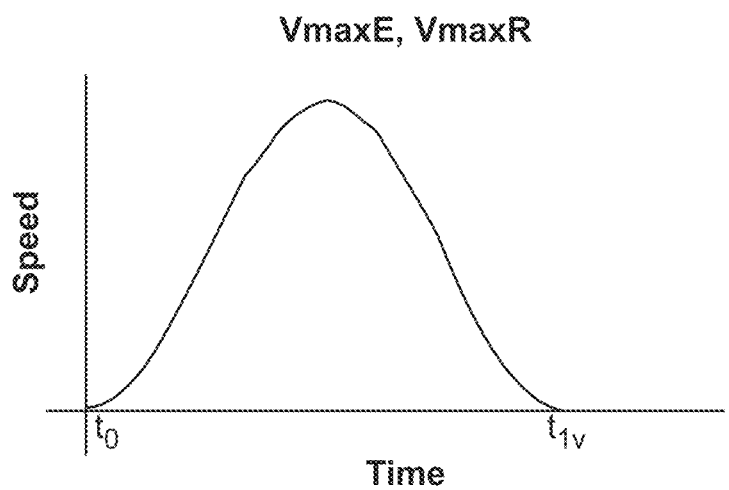
FIG. 10C shows a symmetric motion profile for a cutting tube where an extension speed profile is the same as a retraction speed profile of the elongate member.
Figure 10D:
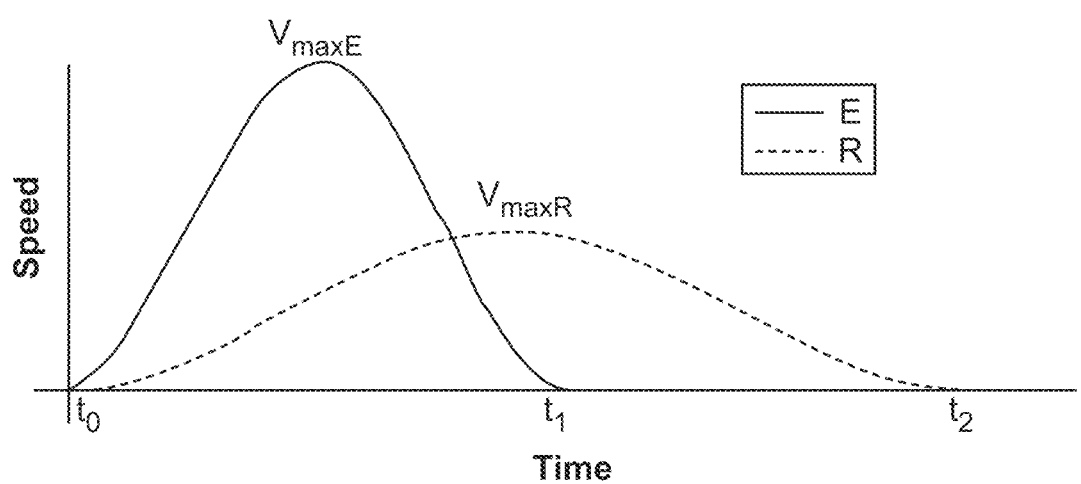
FIG. 10D shows an asymmetric motion profile for a cutting tube where an extension speed profile differs from a retraction speed profile of the cutting tube.

FIGS. 10A and 10C illustrate typical sinusoidal motion profile of a phacoemulsification tip in which the average speed of the tip is substantially the same during proximal retraction as during distal extension (see FIG. 10A). The maximum tip speed of the retraction speed profile R is substantially the same as the maximum tip speed of the extension speed profile E and thus, the motion profiles substantially overlap (see $V_{maxR,E}$ of FIG. 10C). FIG. 10C illustrates a motion profile in which the extension and retraction speed profiles are substantially the same. For example, a 40,000 Hz phaco machine having a 0.1 mm amplitude may have a $V_{max}$ of approximately 12.6 meters/second where the time $T_1$ is approximately 0.0125 ms. FIG. 10B shows the oscillating cutting tube 1112 having a generally non-sinusoidal motion profile in which the average tip speed of the retraction speed profile and the average tip speed of the extension speed profile can be substantially different providing an overall asymmetric movement profile for the oscillating cutting tube. The oscillating cutting tip 1112 has maximum tip speed ($V_{maxR}$) of the retraction speed profile R that is substantially lower than the maximum tip speed ($V_{maxE}$) of the extension speed profile E and thus, the motion profiles do not substantially overlap (see FIG. 10D). FIG. 10D illustrates a motion profile provided where $V_{maxR}$ may be substantially lower such that full retraction is complete at time $T_2$. Thus, the device may have a lower $V_{avg}$.

Figure 10E:
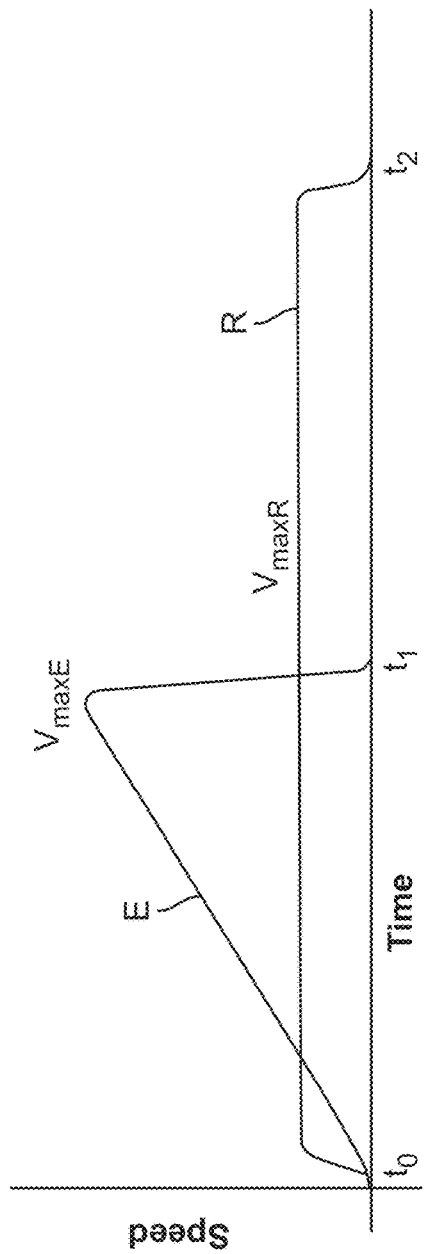
FIGS. 10E-10F show additional examples of extension speed profiles and retraction speed profiles of a cutting tube where the profiles are different.
Figure 10F:
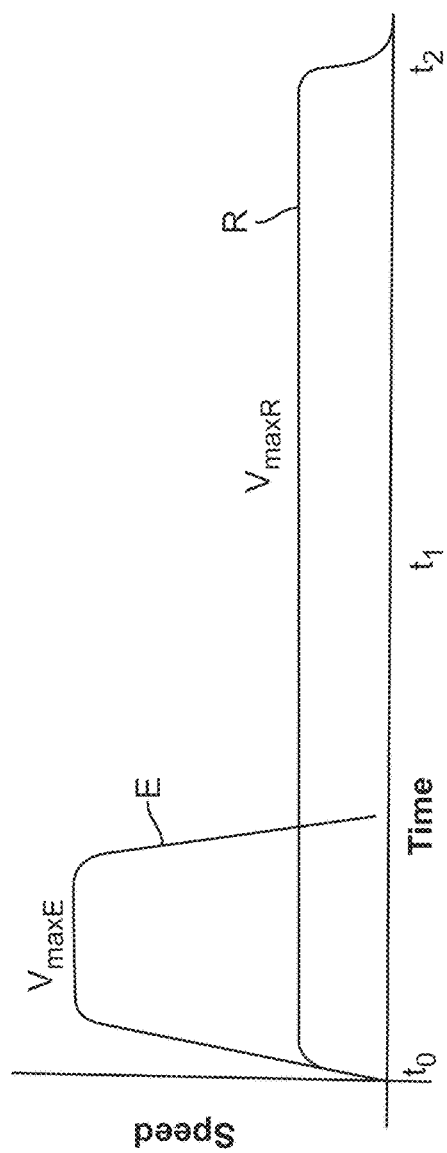

FIGS. 10E-10F illustrate additional asymmetric motion profiles considered herein. The extension speed E can increase linearly to $V_{maxE}$ as the piezoelectric drive compels the cutting tube 1112 forward until it reaches its stroke limit and drops to zero before being retracted. As the cutting tube 1112 is retracted, the retraction speed R increases to $V_{maxR}$ where the speed profile R can form a plateau during which time the retraction speed is roughly constant. Retraction phase is complete at time $T_2$, which is longer than the time $T_1$ it took to complete the extension phase. A dwell or pause period can exist between the extension and retraction phases. The $V_{maxE}$ can be roughly the same as conventional phaco machines (e.g. between about 8 to 12 meters/second). The $V_{maxR}$ can be much lower than conventional phaco machines (e.g. less than about 0.02 meters/second). It should be appreciated that speeds of extension and retraction can vary and that any of a number of non-sinusoidal tip motion profiles are considered herein. In some implementations the $V_{maxE}$ can be between about 2 meters/second and 50 meters/second and the $V_{maxR}$ can be between about 0.001 meters/second and 2 meters/second. In some implementations, the tip speed can be at least 3 meters/second with frequencies less than ultrasonic as described elsewhere herein.

Figure 10G:
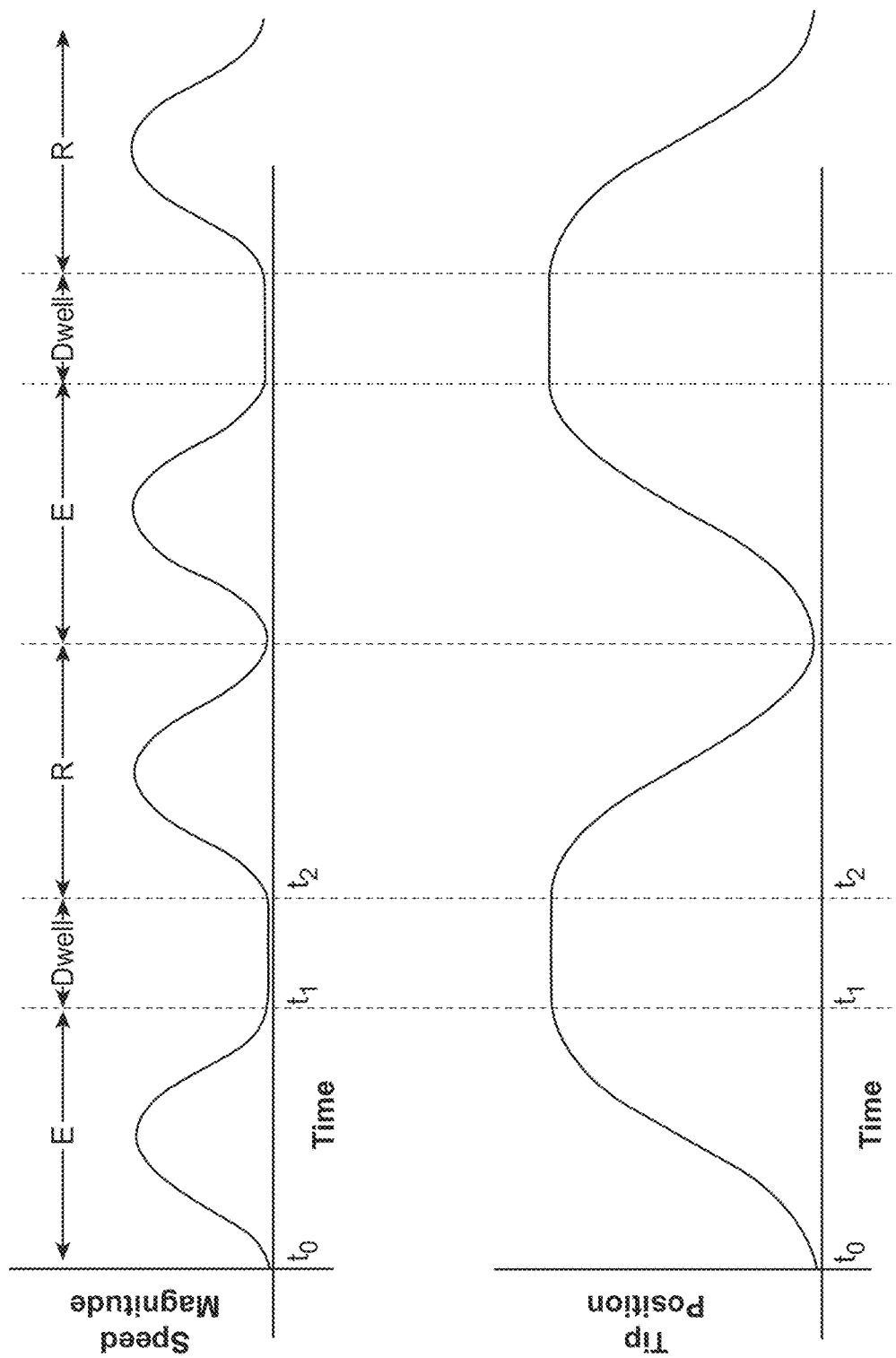
FIG. 10G shows a non-sinusoidal movement of the distal tip of a cutting tube (bottom panel) relative to its extension speed profile (top panel)

The speed profile and movement profile of the movable cutting tube can be generally sinusoidal such that the movement of the distal tip of the cutting tube oscillates in a sinusoidal pattern, corresponding to the frequency of a supplied voltage to the piezoelectric crystal and the resonance of the system it excites. The speed of the distal tip therefore also oscillates in a sinusoidal manner as the derivative of the movement profile. FIG. 10G shows an implementation of non-sinusoidal movement of the distal tip of a cutting tube 1112 (bottom panel) relative to its extension and retraction speed profiles (top panel). Both the speed profiles and the corresponding movement profiles are shown as being non-sinusoidal. The distal tip can have a dwell time between the extension and retraction cycles. Between to and $t_1$, the distal tip can extend forward with a speed profile that may be a sine wave or any other profile. At $t_1$, the distal tip can pause for a dwell period between $t_1$ and $t_2$. The dwell period can be about 0.050 milliseconds, or between about 0.001 and 0.025 milliseconds. At $t_2$, the distal tip can retract with a speed profile that may also follow a sine curve. The movement of the distal tip resembles a sine wave having a dwell at its most extended position.

The non-sinusoidal patterns, for example as shown in FIG. 10G, can reduce the likelihood of cavitation because the dwell time allows for the fluid in the eye that is displaced by movement of the cutting tube 1112 during extension to return to a zero momentum state before retraction of the cutting tube 1112 begins. Sinusoidal patterns of cutting tube motion pushes the fluid away from the distal tip and then retracts immediately while the fluid may still be traveling away from the distal tip thereby increasing the likelihood of cavitation due to the relative velocity of the fluid to the distal tip. The relative velocity of the fluid to the distal tip is higher if the fluid of the eye is being carried away from the tip by momentum while the distal tip itself begins retracting. The dwell period can allow the fluid being displaced to return towards a zero momentum or zero velocity state before the distal tip begins to retract. In this implementation, the extension speed profile and the retraction speed profile may be similar or identical, but the overall speed profile and movement of the distal tip is non-sinusoidal. Other implementations are contemplated herein. For example, the cutting tube 1112 can slow down more gradually as it approaches its fully extended position than a typically sine wave pattern would. As the cutting tube 1112 retracts, the profile would follow a more symmetric path. Any number of other non-sinusoidal patterns are considered.

It should be appreciated that the term "non-sinusoidal" as used herein can be defined as a movement or speed profile that does not follow a simple sine wave pattern of oscillating movement. A simple sine wave may be defined by a single frequency, a single phase shift, and a single amplitude. Certain complex profiles may be generated by adding or subtracting sine waves. However, these complex profiles may also be considered non-sinusoidal because their addition or subtraction does not follow a simple, single sine wave pattern. Where the non-sinusoidal cutting tube motion is referred to herein as retracting and extending, side-to-side, torsional motion is considered as well.

The drive mechanism is capable of retracting the cutting tube 1112 in a proximal direction with a retraction speed profile and advancing the cutting tube 1112 in a distal direction with an extension speed profile such that the retraction speed profile is different from the extension speed profile. The average retraction speed of the cutting tube from the retraction speed profile can be lower than the average extension speed of the cutting tube from the extension speed profile. Thus, the drive mechanism operatively coupled to the cutting tube 1112 is configured to asymmetrically oscillate the cutting tube 1112. The extension speed profile E can include a $V_{maxE}$ and the retraction speed profile R can include a $V_{maxR}$ where the $V_{maxR}$ is less than the $V_{maxE}$. The $V_{maxR}$ of the cutting tube 1112 is generally kept below a threshold speed at which cavitation bubbles would be generated in the eye. Without limiting this disclosure to any particular threshold speed, one of skill in the art would understand the theoretical speed of retraction at which cavitation occurs is generally about 5 meters/second. As such, the $V_{maxR}$ of the cutting tube 1112 may be maintained below about 5 meters/second.

It should be appreciated that preventing cavitation can be achieved even in instances of purely sinusoidal/resonant oscillation motion of the cutting tube 1112. The sinusoidal resonant oscillation can be sufficient velocity to disrupt lens tissue, but is slow enough to avoid cavitation as it retracts. For example, the frequency of oscillation can be reduced or the stroke distance can be reduced. In an implementation, the amplitude of the cutting tube 1112 is 0.016 inch or about 0.4 mm and the frequency is 3,900 Hz in a sinusoidal/resonant oscillation motion. The $V_{maxR/E}$ in this configuration may be kept below 5 m/s, which is fast enough to disrupt the lens tissue and slow enough to avoid cavitation. The $V_{maxR/E}$ can be at least about 3 m/s, but remain within the sub-ultrasonic frequency range.

The oscillating movements of cutting tube driven by conventional phacoemulsification systems may have a degree of variability due to normal losses during movement (e.g. due to friction or variability in material compression under load or other environmental factors). This variability may impact the maximum and average speeds achieved during retraction and extension such that the retraction speed profile and extension speed profile are not identical or perfectly sinusoidal. However, this normal variability during movements of component parts is not intentionally engineered or designed to occur (i.e. a control processor operating according to program instructions stored in a memory; or hardware in operable communication with the control processor designed to achieve different speeds depending on phase of cycling). Thus, normal variability in speed during movement is not considered to be contributing to or resulting in an asymmetric motion profile. The asymmetric motion profiles described herein are consciously engineered or designed motion profiles intended to be substantially reproducible during each cycling and not merely due to chance variability.

As described elsewhere herein, the aspiration pump 1014 of the hand piece 1030 can be configured to provide pulses of discontinuous negative pressure. Movement of the rollers or the pistons creates vacuum pulses that can be coordinated or linked to phases of movement of the elongate cutting tube 1112.

Figure 11B:
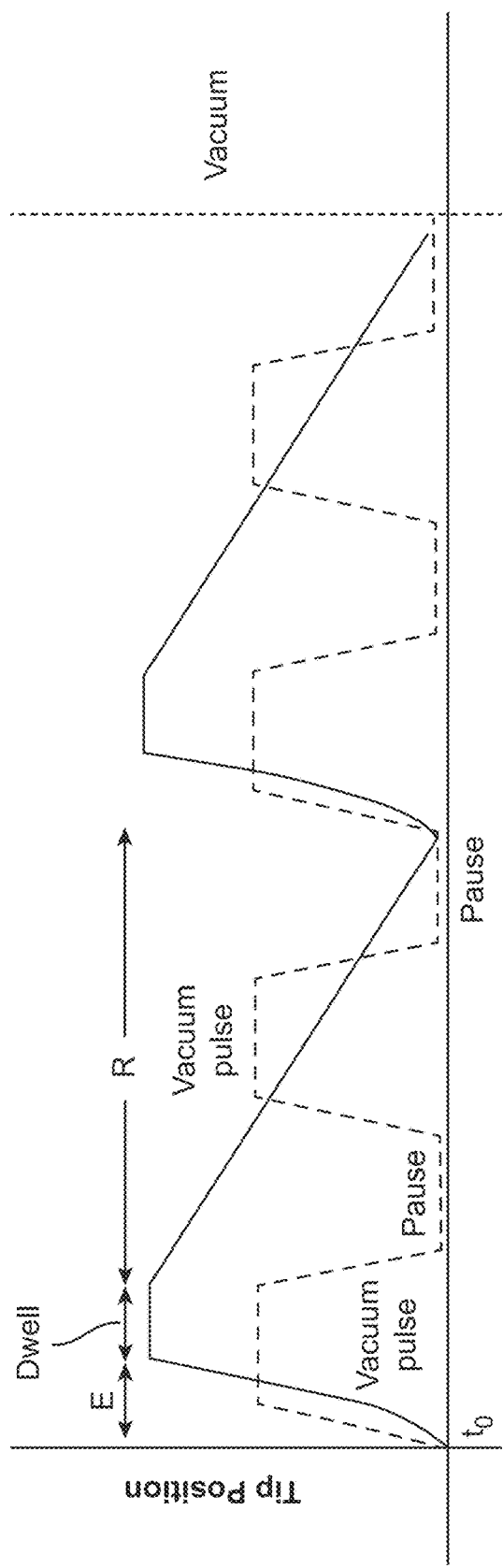
FIGS. 11B-11D show overlap between an asymmetric, non-sinusoidal motion profile for a cutting tube (solid line) and a vacuum profile for aspiration through the cutting tube (hatched line) with the piston pump.
Figure 11C:
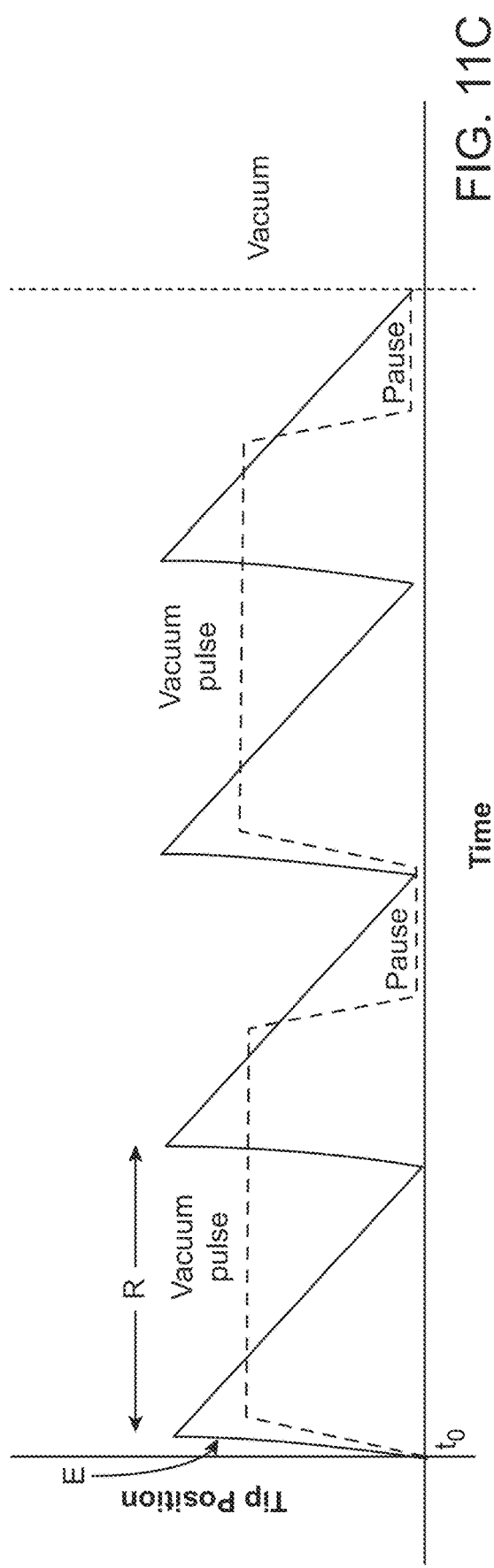
Figure 11D:
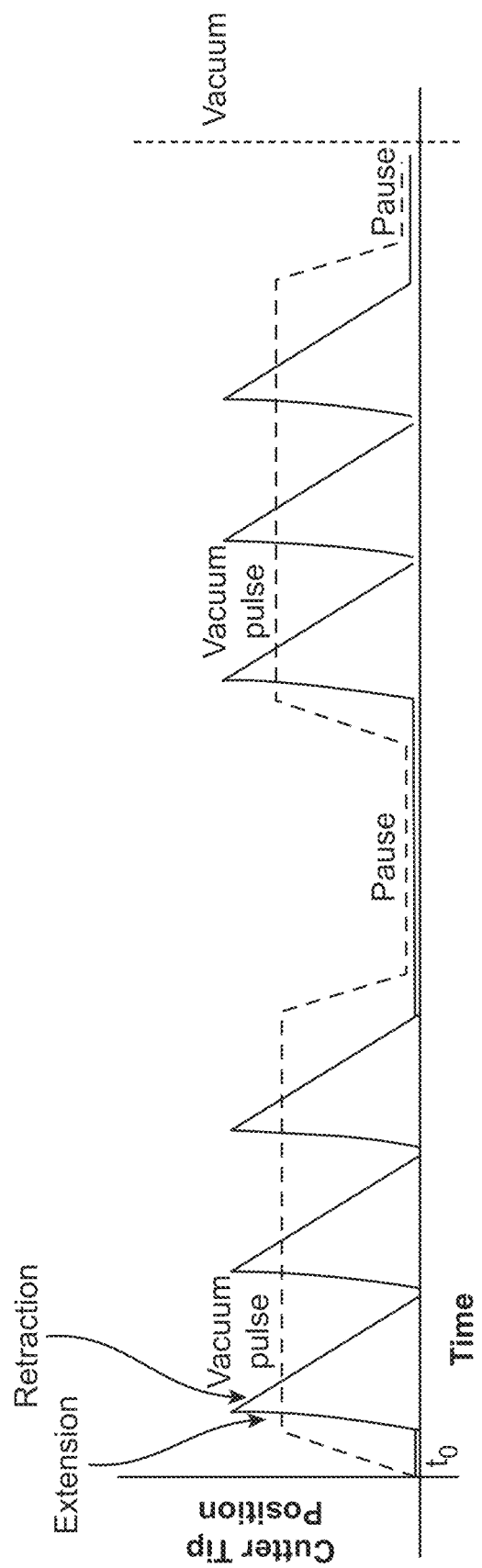
Figure 11E:
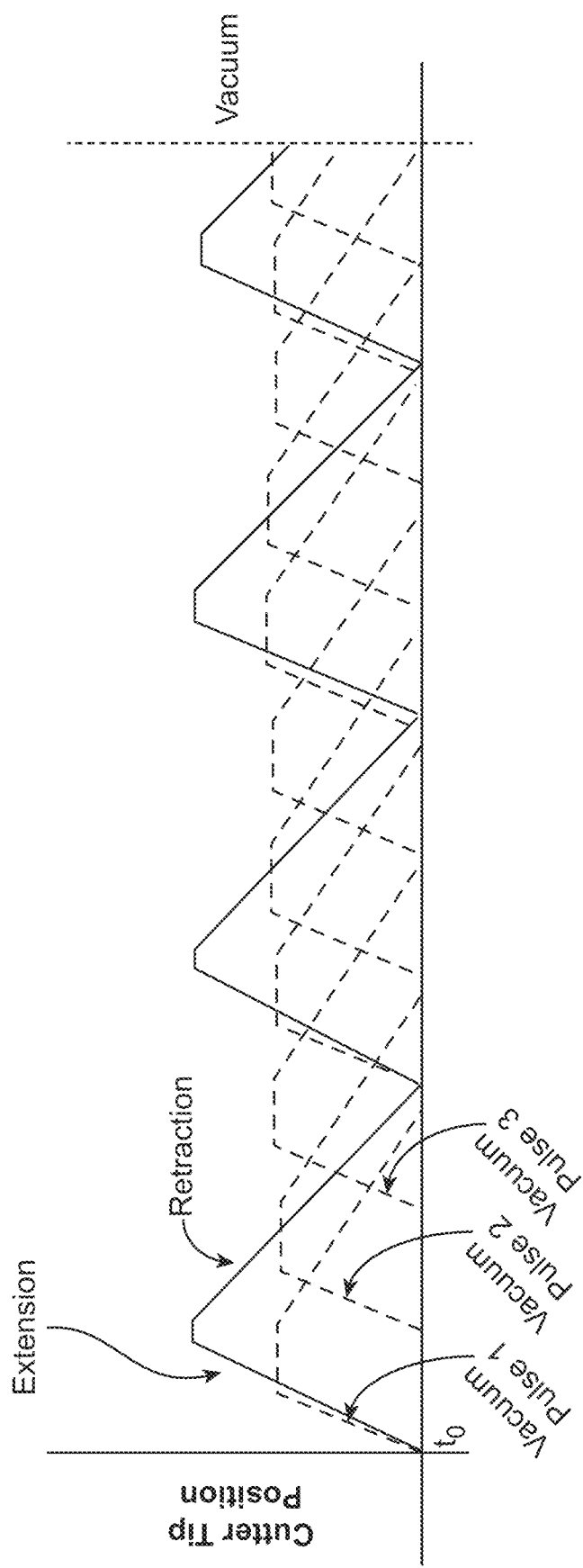
FIG. 11E shows overlap between an asymmetric, non-sinusoidal motion profile for a cutting tube (solid line) and a vacuum profile for aspiration through the cutting tube (hatched line) with the piston pump.
Figure 11F:
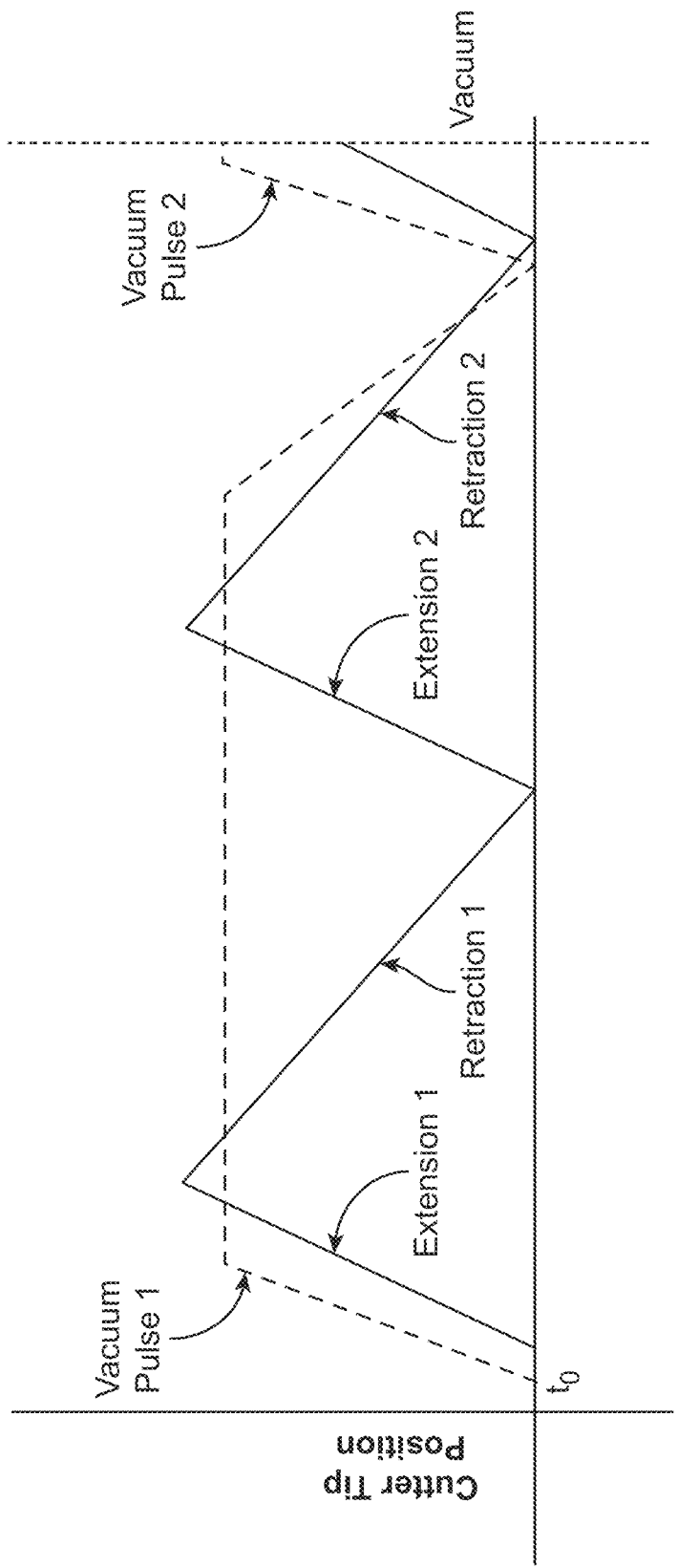
FIG. 11F shows overlap between an asymmetric, non-sinusoidal motion profile for a cutting tube (solid line) and a vacuum profile for aspiration through the cutting tube (hatched line)

For example, a pulse of aspiration can be drawn through the lumen 1110 of the cutting tube 1112 during at least a portion of the extension as the cutting tube 1112 moves in a distal direction and/or during at least a portion of the retraction as the cutting tube 1112 moves in a proximal direction. FIG. 11A illustrates an implementation of a vacuum profile over time for the pulsatile vacuum applied through the distal end region of the lumen 1110 of the cutting tube 1112 where the pump 1014 is a piston pump having a plurality of pistons. The plurality of pistons may be configured to move sequentially within their respective pumping chambers creating periods of increasing vacuum interspersed by periods of decreasing vacuum. It should be appreciated that a pulsatile aspiration can be achieved with other pump configurations such as a peristaltic pump or other pump configuration. In some implementations, the increase in vacuum can occur faster than the decrease in the vacuum providing a vacuum profile. The pulsatile vacuum profile applied through the lumen 1110 of the cutting tube 1112 can be synchronized with the motion profile of the cutting tube 1112 performing the cutting such that at least a part of the period of negative pressure is applied during a certain phase of movement. FIGS. 11B-11D show the movement of the cutting tube 1112 (solid lines) relative to the periods of negative pressure (hatched lines) applied through the cutting tube 1112. The period of negative pressure (i.e. vacuum pulse) can occur before forward stroke or distal extension E of the cutting tube 1112, during at least part of the forward stroke or distal extension E of the cutting tube 1112, dwell time after distal extension E and before proximal retraction R, and/or during at least part of the proximal retraction R of the cutting tube 1112. For example, FIG. 11B shows a first pulse of vacuum pressure occurs during the extension E of the cutting tube 1112 as well as the dwell time after extension E and before retraction R. The first pulse of vacuum pressure ends during the retraction R phase and a second pulse of vacuum begins and ends before the same retraction phase ends. FIG. 11C shows another implementation where a first pulse of vacuum pressure begins during extension E of the cutting tube 1112 and is maintained during retraction R phase of the cutting tube 1112 as well as during a second extension E of the cutting tube. FIG. 11B shows the vacuum pulse having about 2× the frequency of tip movement and FIG. 11C and also FIG. 11F shows the tip movement having about 2× the frequency of the vacuum pulse. Both FIG. 11B and FIG. 11C show vacuum pulse occurring during a portion of the extension E and retraction R. FIG. 11D shows another implementation of the coordination between cutting tube movement and application of negative pressure. The motion profile of the cutting tube (solid lines) need not correspond with a single trapezoidal vacuum pulse (hatched lines). Rather, the motion of the cutting tube can allow for multiple extensions E and retractions R (or oscillations) during a single pulse of vacuum. FIGS. 11D and 11F illustrate the movement of the cutting tube or tip oscillation can begin after the vacuum pulse is initiated. The cutting tube can undergo multiple extensions and retractions for each pulse of vacuum. FIG. 11F shows two cycles of cutting tube extension and retraction for each pulse of vacuum. The cutting tube can extend and retract a number of times (1, 2, 3, 4, 5, 10, 15, 20, 25, 30, 35, 40, 45, or 50 times) for each pulse of vacuum such that the ratio of hits per vacuum pulse is 1:1, 2:1, 3:1, 4:1, 5:1, 10:1, 20:1, 25:1, 30:1, 35:1, 40:1, 45:1, 50:1 and so on. The cutting tube or tip oscillation can also begin before the vacuum pulse is initiated (see FIG. 11C). It should be appreciated that the hand piece can apply vacuum pulses without any cutting tube motion at all such that vacuum pulses alone are used to break up the lens. The vacuum pulses can vary in frequency from about 1 vacuum cycles/second to about 100, or from about 5 to about 50, or from about 10 to about 25 vacuum cycles/second, and any range or vacuum cycles/second amount in between.

Once the pulse of vacuum returns back to zero, the movement of the cutting tube or tip oscillation can cease.

The system can then enter a rest period for both motion and vacuum for a period of time before the next sequence begins. The frequency of extensions and retractions of the cutting tube 1112 within a single pulse of vacuum can vary. For example, the cutting tube 1112 can undergo 1, 2, 3, 4, 5, or more extension/retraction movements for each pulse of vacuum up to about 10, 15, 20, 25, 30, 35, 40, 45, 50, 55, or more extension/retraction movements for each pulse of vacuum. In an implementation, the speed of the retraction is half the speed of extension. In other words, the retraction time takes twice as long as the extension time to travel the same distance. The frequency for this configuration is $\frac{1}{3}^{rd}$ less than the frequency for a configuration where the retraction speed is identical to the extension speed. For example, a 40 kHz, 0.1 mm phaco system would have a frequency of 27 kHz.

The frequency of cutting tube 1112 oscillations can change with different amplitudes and velocity thresholds. The amplitude can be between 0.005 mm to about 1.0 mm, or more preferably between 0.05 mm to about 0.1 mm. The frequency of oscillation can be less than 30,000 Hz, less than 25,000 Hz, less than 20,000 Hz, less than 15,000 Hz, or less than 10,000 Hz and down to about 0.5 Hz, or down to about 1 Hz, or down to about 2 Hz, or down to about 5 Hz, or down to about 10 Hz, or down to about 25 Hz, or down to about 50 Hz, or down to about 100 Hz, or down to about 250 Hz, or down to about 500 Hz. The frequency of cutting tube oscillation can be between about 0.5 Hz to about 30,000 Hz, or between 1 Hz to about 5000 Hz, or between about 2 Hz to about 2000 Hz.

As mentioned elsewhere herein, a vacuum pulse may be applied through the cutting tube 1112. The relative coordination of the vacuum pulse and the motion of the cutting tube 1112 can vary. A pulse of vacuum may be applied during at least a portion of the extension of the cutting tube 1112. A pulse of vacuum may be applied during at least a portion of the retraction of the cutting tube 1112. A pulse of vacuum may be applied during at least a portion of both extension and retraction of the cutting tube 1112. In some implementations, the pulse of vacuum may begin before and be maintained during extension of the cutting tube 1112. The pulse of vacuum may begin after extension of the cutting tube 1112 begins. A single pulse of vacuum may be applied during multiple extensions and retractions. For example, the vacuum may be applied continuously through the cutting tube 1112 during at least about 1 oscillation, at least about 2 oscillations, at least about 5 oscillations, at least about 10 oscillations, at least about 20 oscillations, at least about 30 oscillations, at least about 40 oscillations, at least about 50 oscillations, at least about 100 oscillations of the cutting tube 1112, up to about 500 oscillations of the cutting tube 1112. The length of the vacuum pulse for an oscillation frequency of about 25 kHz can be at least about 2 ms up to about 25 ms. As an example, the cutting tube 1112 may oscillate 50 times during a single vacuum pulse that lasts 25 ms such that the frequency of oscillation of the cutting tube 1112 is about 2000 Hz.

In some implementations, the aspiration pump 1014 is a piston pump having multiple pistons. The motions of the plurality of pistons can provide pulsatile, discontinuous aspiration. The retraction periods of the plurality of pistons may overlap in a manner that provides smooth continuous aspiration (with or without a spike in negative pressure in between movements). FIG. 11E shows the movement of the cutting tube 1112 (solid lines) relative to the periods of negative pressure (hatched lines) applied through the cutting tube 1112 where the aspiration pump 1014 is a piston pump having a plurality of pistons. Retraction of a first piston can create a first pulse of vacuum and retraction of a second piston can create a second pulse of vacuum that overlaps with the first pulse. Retraction of a third piston can create a third pulse of vacuum that overlaps with the second pulse of vacuum and so on. The result is a substantially continuous vacuum pressure that occurs during both extension and retraction of the cutting tube. The vacuum applied during the period of overlapping pulses can, but need not, have a reduced maximum vacuum compared to the implementation of pulsed vacuum where the pulses do not significantly overlap.

Figure 11G:
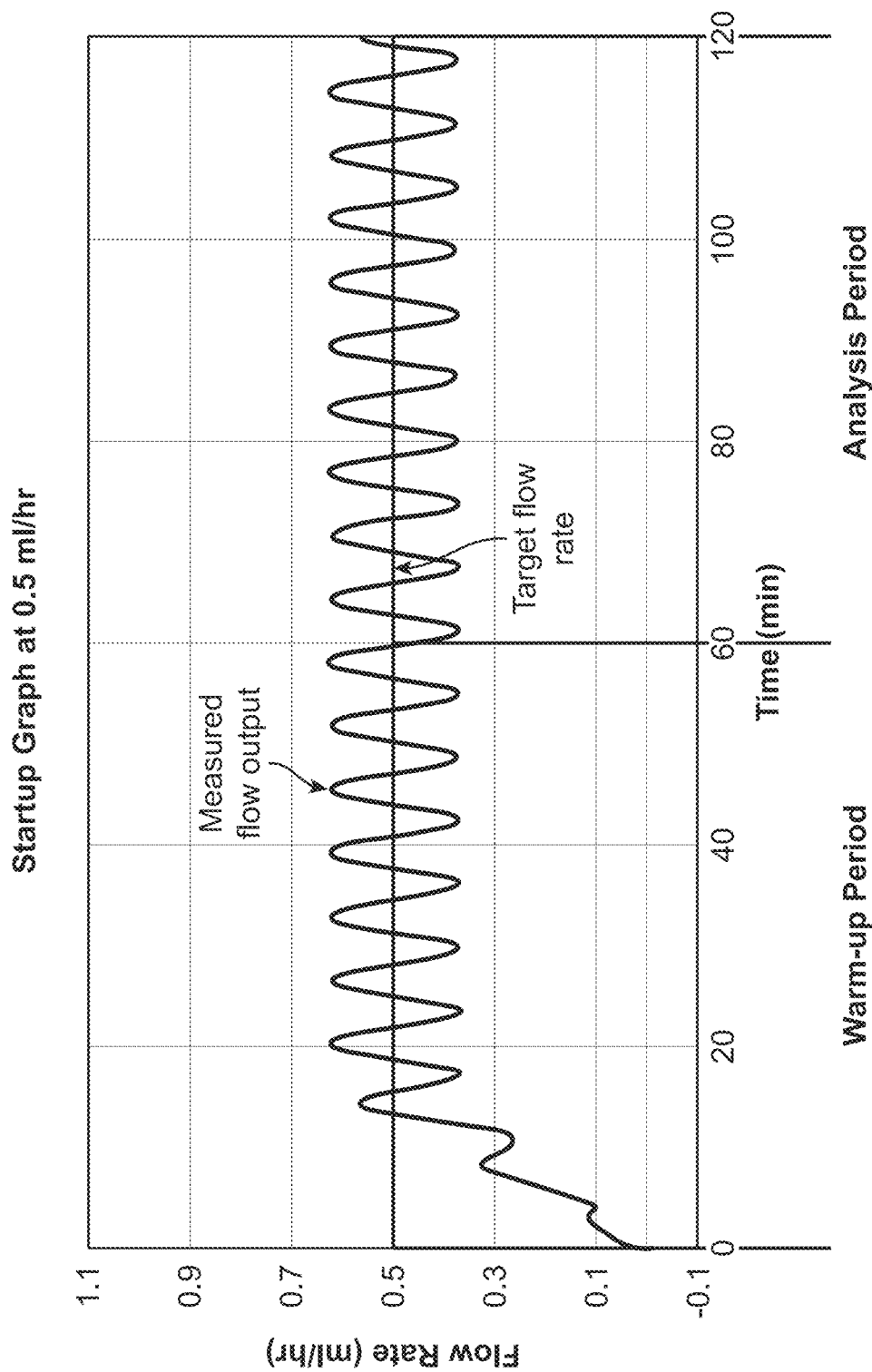
FIG. 11G shows an implementation of a vacuum profile for a peristaltic pump in the hand piece.

In some implementations, the aspiration pump 1014 is a peristaltic pump having one or more rollers. FIG. 11G shows an implementation of a vacuum profile over time for the pulsatile vacuum applied through the distal end region of the lumen 1110 of the cutting tube 1112 where the pump 1014 is a peristaltic pump having one or more rollers.

It should be appreciated that any number of various relative frequencies are considered herein and that these are illustrations of some examples of the relative speed profiles and vacuum profiles.

Control Unit

Again with respect to FIGS. 3-4, the hand piece 1030 may be part of or coupled to the phacoemulsification system 1010 to provide irrigation and aspiration support as well as power for the cutting tube drive mechanism and the aspiration pump 1014 in the hand piece 1030. It should be appreciated, however, that the hand piece 1030 can be used independently of the phacoemulsification system 1010. As described above, the system 1010 can include the control unit 1012, which can include the ultrasonic power source 1016 and the microprocessor 1018 that provides control outputs to the pump controller 1020 and the ultrasonic power level controller 1022.

The hand piece 1030 can be plugged into a socket coupled to the ultrasonic power source 1016 of the system 1010. A proximal end of the reusable portion 1033 of the hand piece 1030 can include power cords 1160 configured for providing power to the piezoelectric stack 1120 as well as the pump motor 1115. Power for the pump motor 1115 can be DC power whereas the power for the piezoelectric stack 1120 can be ultrasonic power similar to conventional phacoemulsification systems.

The control unit 1012 of the system 1010 can be controlled, adjusted, and/or programmed remotely such as via an external computing device and/or the hand piece 1030. The control unit 1012 of the system 1010 can also be controlled, adjusted, and/or programmed directly via one or more inputs. The inputs of the system 1010 can include one or more triggers, buttons, sliders, dials, keypads, switches, touchscreens, foot pedals, or other input that can be retracted, pressed, squeezed, slid, tapped, or otherwise actuated to activate, modify, or otherwise cause a response of the system 1010. In some implementations, the one or more inputs includes a microphone configured to receive voice commands to control, adjust, and/or program one or more components of the system 1010 as well as peripheral devices in operative communication with the system 1010, such as a smart phone or tablet application.

One or more aspects of the hand piece 1030 and the system 1010 can be programmed by a user. For example, one or more aspects of the drive mechanism can be programmed by a user to control the motion of the cutting tube 1112 including, but not limited to travel distance of the cutting tube 1112, frequency of oscillation of the cutting tube 1112, maximum extension speed ($V_{maxE}$), minimum extension speed ($V_{minE}$), maximum retraction speed ($V_{maxR}$), minimum retraction speed ($V_{minR}$), average extension speed ($V_{avgE}$), average retraction speed ($V_{avgR}$), or any other aspect of the motion profile. In some implementations, the distance the cutting tube 1112 moves with each cycle can be adjustably programmed such that the amplitude and/or frequency of its oscillation is selectable within a range. The range of amplitude can be 0.005 mm up to about 0.4 mm. The range of frequency can be between about 0.5 Hz to about 5000 Hz, or frequency in a range of about 2 Hz to about 2000 Hz. The oscillation frequency can be less than ultrasonic, for example, less than about 20,000 Hz or within the ultrasonic range (e.g. about 20,000 Hz, to about 120,000 Hz, up to the gigahertz range). The system 1010 (and/or the hand piece 1030) can be programmed to provide limits on a particular action upon actuation of the input. For example, the drive mechanism can be programmed to have a minimum and/or maximum upon actuation of the input or, in the case of fluid infusion and aspiration, the device can be programmed to have a minimum and/or maximum fluid pressure upon actuation of an input. Thus, the devices described herein can be programmed using inputs adjustable by a user as well as by pre-programmed instructions that impact the one or more aspects of the device upon actuation of the inputs.

As mentioned above, the system 1010 can additionally include a remote aspiration pump within the control unit 1012 in addition to the aspiration pump 1014 within the hand piece 1030. The aspiration pump 1014 integrated within the hand piece 1030 can be a relatively high pressure pump. The remote aspiration pump can be a lower pressure pump, such as a peristaltic pump within the control unit 1012 that can provide fluid movement within the aspiration line 1038 towards the waste container 1044. The remove aspiration pump can be configured to directly accept the aspiration line 1038 to direct fluid into the waste container 1044. For example, the remote aspiration pump can include rotating pump head having rollers around its perimeter. As the pump head rotates, the rollers press again the aspiration line 1038 causing fluid to flow within the aspiration line 1038 a certain direction (i.e. towards the waste container 1044). The remote aspiration pump can also accept a pump cartridge having an integrated waste container 1044. The aspiration pump 1014 in the hand piece 1030 can be used for certain parts of a procedure, for example, during cutting of the lens material, and the remote aspiration pump in the control unit 1012 can be used for cleanup of small particles remaining in the eye after the cutting is complete. The remote aspiration pump can be activated manually such as by an input on the system 1010 and/or upon actuation of the hand piece 1030.

One of more aspects of the internal aspiration pump 1014 (and any remote aspiration pump) can be programmed by a user to control the vacuum applied at the distal end region of the cutting tube 1112 including, but not limited to flow rate of aspiration, minimum vacuum pressure, maximum vacuum pressure, frequency of vacuum pulses, or any other aspect of the vacuum profile. In some implementations, the flow rate of aspiration can be adjustably programmed within a range of between about 5-100 ml/min.

The hand pieces described herein are configured to deliver irrigation to the work site from an irrigation fluid source 1032 fluidly coupled to the hand piece 1030 through an irrigation line 1034. Conventional irrigation containers for ophthalmic surgery can be between 250 mL to about 500 mL each resulting in a relatively large volume of irrigation fluid available for delivery to the eye. The volume of irrigation fluid needed and thus, the size of the irrigation fluid source 1032 used during a procedure using the hand piece 1030 described herein can be drastically reduced compared to conventional systems. As described above, the hand piece 1030 has an aspiration pump 1014 positioned near the distal cutting tip, e.g. a peristaltic or roller pump, a scroll pump, a piston pump, and the like, configured to create a pulsatile vacuum profile. The strength of the pulsatile vacuum to aspirate fluid may be much stronger than vacuum applied in conventional systems not incorporating pulse. The very strong and very short pulses are sufficient to remove the lenticular tissue and thus, require only relatively small amounts of fluid. The ratio of lenticular tissue to fluid being aspirated from the anterior chamber may be higher in the hand-held devices described herein than in other currently used devices and methods. Also, the fluid volumes delivered using the devices described herein can be significantly reduced compared to known systems because irrigation is delivered only upon activation of the device. The total volume of irrigation fluid needed for a procedure using the devices described herein is significantly less (e.g. as low as about 10 mL) compared to conventional systems. In some implementations, the aspiration is delivered by a vacuum source located within the hand-held instrument (i.e. pump 1014 integrated within the hand piece 1030). The aspiration can be activated with finer control than currently used devices and methods. For example, the hand piece 1030 can use a finger control that allows the surgeon to easily activate the device for short periods of time in a manner more convenient and easier than would a foot pedal used in most conventional phacoemulsification machines. Further, since the vacuum source can be located within the hand piece 1030 there may be a significantly faster response time for the surgeon to activate device on and off than in other devices where the vacuum source is located in a console that is several feet away and connected by tubing. The hand piece 1030 has a relatively low amount of surge volume, and therefore cycling the device on and off has minimal downside. These features can allow the hand piece 1030 to be activated for only brief periods when the surgeon is ready to remove lenticular tissue. This contributes to overall less irrigation fluid being removed and thus less irrigation fluid needed to be delivered.

The volume of a human lens is about 0.10 mL-0.15 mL. The total irrigation fluid volume needed for a procedure using the devices described herein is generally less than 250 mL, such as about 10 mL, 25 mL, 50 mL, 75 mL, 100 mL, 125 mL, 150 mL, 200 mL. Generally, for the devices described herein, the ratio of irrigation fluid volume needed for a procedure to lens fluid volume is kept very low, between about 50:1, 75:1, 100:1, 150:1, 200:1, up to about 2000:1. As an example, using 10 mL of BSS is a ratio of about 100:1. In contrast, using 250 mL of BSS is a ratio of about 2500:1 of irrigation fluid to lenticular tissue.

The irrigation source 1032 can be suspended from a pole assembly of the system 1010, including one or more features typical of an intravenous (IV) pole of more conventional systems. The pole assembly can include a telescoping pole configured to be movable relative to a base such that the height of one or more hangers suspending the irrigation source 1032 can be adjusted. The height of the irrigation source 1032 can be calculated to create the proper fluid pressure in the irrigation fluid line 1034. The pole assembly can incorporate one or more buttons, levers, or foot pedals configured to adjust the height of the irrigation source 1032 thereby altering the irrigation fluid pressure and, correspondingly, alter the flow rate of the fluid in the irrigation fluid line 1034. The height of the irrigation source 1032 can be adjusted manually and/or via a powered adjustment. For example, the pole assembly can include a motorized system configured to move the telescoping pole relative to the base. The adjustment of the telescoping pole can be a powered, automatic adjustment by the control unit 1012 depending on the fluid needs during a procedure. The irrigation fluid source 1032 can be suspended above the level of the patient by hangers on the pole assembly and one or more valves configured to control flow from the source 1032 through the irrigation fluid line 1034. The one or more valves can include pinch valves or pinch clamps configured to tightly pinch the irrigation line 1034 thereby preventing fluid flow towards the hand piece 1030 or allowing flow of fluid from the irrigation source 1032 upon opening the valve. The valves can be manual valves or can be actuated upon an input by the control unit 1012.

It should be appreciated that the irrigation fluid source 1032 need not hang from an IV pole. The volume of the irrigation fluid source 1032 can be sized small enough that it can be placed near the surgical site. For example, the irrigation fluid can be delivered from a small container, such as a syringe-type container or collapsible bag that can provide the irrigation flow without the need for gravity or for being suspended from an IV pole. The container can be fluidly coupled to the hand piece 1030 with a short irrigation line length. The container can be positioned on a user's wrist or arm (e.g. via a wristband or armband) or patient's sterile drape during use of the hand piece 1030. In an implementation, the irrigation fluid source 1032 can be limited to volumes that are less than 250 mL, for example, between about 25 mL to about 100 mL, or as little as 10 mL up to about 100 mL.

The relative amounts of fluids entering and exiting the surgical field of the eye are preferably balanced such that the anterior chamber of the eye does not collapse. The irrigation fluid source 1032 can provide a constant pressure of irrigating fluid that does not change with the vacuum level provided by the aspiration pump 1014 in the hand piece 1030. The suction flow rate out of the eye during the peak vacuum can be higher than the irrigation flow rate into the eye resulting in a momentarily lower pressure in the eye. The pressure source of the irrigating fluid can be raised so that its nominal flow rate is higher than the maximum suction flow rate at the peak vacuum pulse to avoid this low pressure situation. It is preferable, however, to keep the pressure of the irrigating fluid source lower so that the pressure within the eye remains lower than a set amount during a procedure when the vacuum is not being applied. Alternatively, the hand piece 1030 can incorporate a mechanism that is capable of delivering quick rushes or discontinuous pulses of irrigating fluid into the eye, such as from an irrigation fluid reservoir within the hand piece 1030 near the distal tip as described elsewhere herein. Each pulse of irrigation fluid can be timed to occur during each pulse of negative pressure when the suction flow rate is at its maximum. The balance of fluid within the eye can remain more consistent and the drop in pressure within the eye during the peak vacuum point is minimized.

Aspects of the subject matter described herein may be realized in digital electronic circuitry, integrated circuitry, specially designed ASICs (application specific integrated circuits), computer hardware, firmware, software, and/or combinations thereof. These various implementations may include an implementation in one or more computer programs that are executable and/or interpretable on a programmable system including at least one programmable processor, which may be special or general purpose, coupled to receive signals, data and instructions from, and to transmit signals, data, and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any computer program product, apparatus, and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation," "an implementation," or the like, means that a particular feature, structure, configuration, or characteristic described is included in at least one embodiment or implementation. Thus, the appearance of the phrase "one embodiment," "an embodiment," "one implementation," "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. However, such terms are provided to establish relative frames of reference, and are not intended to limit the use or orientation of an anchoring delivery system to a specific configuration described in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A device for extracting lens material from an eye, the device comprising:
a distal, disposable portion releasably coupleable to a proximal, reusable portion, the distal, disposable portion comprising:
a cutting tube comprising a distal cutting tip and an inner lumen, the cutting tube sized and configured to extend through an anterior chamber of the eye and to a capsular bag;
an aspiration pump housed within the disposable portion and fluidly coupled to the inner lumen of the cutting tube, wherein the aspiration pump is a linear peristaltic pump comprising a central camshaft extending longitudinally through a symmetrical double chamber pumping manifold, the central camshaft having a rotational axis that is coaxially aligned with a longitudinal axis of the distal, disposable portion; and
a cutting tube drive mechanism configured to oscillate the cutting tube,
wherein, in use, the device is configured to aspirate lens material from the capsular bag into the inner lumen; and
the proximal, reusable portion configured to remain outside of the eye, the proximal, reusable portion comprising:
an aspiration pump motor configured to drive the aspiration pump; and
a coupler for releasably operatively coupling the pump motor to the aspiration pump.

2. The device of claim 1, wherein the aspiration pump motor rotates the central camshaft.

3. The device of claim 1, wherein the linear peristaltic pump further comprises two tubes extending through the pumping manifold, each of the two tubes comprising a longitudinal axis that is positioned parallel with the rotational axis of the central camshaft.

4. The device of claim 3, a first tube of the two tubes is positioned on one side of the camshaft and a second tube of the two tubes is positioned on a second, opposite side of the camshaft.

5. The device of claim 4, wherein the linear peristaltic pump further comprises a proximal flow path and a distal flow path.

6. The device of claim 5, wherein the proximal flow path splits into two flow paths connected on a proximal end with the two tubes within the pumping manifold.

7. The device of claim 5, wherein the two tubes combine distal to the pumping manifold into the distal flow path.

8. The device of claim 5, wherein the camshaft further comprises a plurality of lobed cams that work in time to drive a plurality of cam followers towards and away from the two tubes to create sequential, progressive compression of the two tubes to push a fluid volume toward the distal flow path.

9. The device of claim 8, wherein motion of the plurality of cam followers is in a plane perpendicular to the rotational axis of the camshaft and to the longitudinal axis of the two tubes.

10. The device of claim 9, wherein the plurality of cam followers sequentially compress the two tubes in a wave-like fashion.

11. The device of claim 9, wherein the plurality of cam followers apply no force in a direction of the longitudinal axis of the two tube and generate little to no friction on the two tubes.

12. The device of claim 1, further comprising an external vacuum source operatively releasably coupleable to at least one of the proximal, reusable portion and the distal, disposable portion, wherein the external vacuum source is configured to provide continuous vacuum pressure within the inner lumen.

13. The device of claim 12, wherein the continuous vacuum pressure creates less suction force than the vacuum pressure generated by the aspiration pump of the distal, disposable portion.

14. The device of claim 1, wherein the cutting tube drive mechanism causes oscillatory motion of the cutting tube via a mechanical hinge.

15. The device of claim 1, wherein the cutting tube drive mechanism incorporates less than 2 nodal inflection points between a point of application of a drive force and the distal cutting tip of the cutting tube.

16. The device of claim 1, wherein the cutting tube drive mechanism comprises a base, a rocker, and a pivot pin, the rocker being movably coupled to the base by the pivot pin and configured to rotate relative to the base around a rotational axis of the pivot pin.

17. The device of claim 16, wherein the cutting tube extends through a center of the rocker and wherein the pivot pin is substantially aligned along the longitudinal axis of the cutting tube creating a fulcrum for the rocker.

18. The device of claim 16, wherein the drive mechanism further comprises a piezoelectric stack and a spring stack, the piezoelectric stack and the spring stack being positioned on opposite sides of the cutting tube.

19. The device of claim 18, wherein the spring stack creates an upward force against a first end of the rocker urging a second, opposite end of the rocker downward against the piezoelectric stack.

20. The device of claim 19, wherein the piezoelectric stack expands under varying voltage rotating the rocker about the rotational axis of the pivot pin causing the cutting tube to move in at least one direction.

21. The device of claim 20, wherein retraction of the piezoelectric stack allows the upward force of the spring stack against the first end of the rocker to urge the second, opposite end of the rocker downward maintaining contact with the retracting piezoelectric stack.

22. The device of claim 16, wherein the drive mechanism further comprises a motor-driven cam and a cam follower coupled to the rocker.

23. The device of claim 16, wherein the drive mechanism further comprises a motor and a motor shaft, the motor shaft having an offset weight configured to cause motion of the rocker as the motor shaft spins.

24. The device of claim 16, wherein the rocker is a straight rocker and the pivot axis of the pivot pin is aligned with a plane of the rocker, the plane extending perpendicular to the longitudinal axis of the cutting tube.

25. The device of claim 16, wherein the rocker is an offset rocker and the pivot axis of the pivot pin is positioned proximal to a plane of the rocker, the plane extending perpendicular to the longitudinal axis of the cutting tube.

26. The device of claim 1, wherein the cutting tube drive mechanism creates a drive force applied to generate longitudinal oscillatory motion and/or torsional oscillatory motion.

27. The device of claim 26, wherein the oscillatory motion is in an ultrasonic frequency range.

28. The device of claim 26, wherein the oscillatory motion is in a frequency range that is less than ultrasonic.

29. The device of claim 26, wherein a frequency of oscillation of the distal cutting tip is between about 0.5 Hz to 5000 Hz.

30. The device of claim 1, wherein the cutting tube incorporates a non-circular cross-sectional geometry along at least a portion of its length.

31. The device of claim 30, wherein the non-circular cross-sectional geometry comprises oval, elliptical, lentoid, tear-drop, or diamond.

32. The device of claim 1, wherein the cutting tube incorporates at least a first tapered profile extending laterally from a central axis of the cutting tube.

33. The device of claim 1, wherein the cutting tube has an asymmetric cross-section forming a single tapered profile extending from one side of the cutting tube and a circular profile on an opposite side of the cutting tube.

34. The device of claim 1, wherein the cutting tube has a cross-sectional shape that varies along its length.

35. The device of claim 1, wherein only a distal-most length of the cutting tube incorporates a non-circular geometry.

36. The device of claim 35, wherein the distal-most length is approximately 1 mm.

37. The device of claim 1, wherein the proximal, reusable portion further comprises a throttle mechanism for varying a speed of the aspiration pump motor, the throttle mechanism operatively coupled to an actuator.

38. The device of claim 1, further comprising an irrigation lumen coupleable to a source of irrigation fluid.

39. The device of claim 38, wherein the irrigation lumen comprises an annular space at least in part surrounding the cutting tube.

* * * * *